United States Patent
Segawa et al.

(10) Patent No.: US 8,419,620 B2
(45) Date of Patent: Apr. 16, 2013

(54) MAGNETICALLY GUIDING SYSTEM AND MAGNETICALLY GUIDING METHOD

(75) Inventors: Hidetake Segawa, Hachioji (JP); Atsushi Chiba, Hachioji (JP); Atsushi Kimura, Akiruno (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/617,839

(22) Filed: Sep. 14, 2012

(65) Prior Publication Data

US 2013/0018225 A1   Jan. 17, 2013

Related U.S. Application Data

(62) Division of application No. 12/486,399, filed on Jun. 17, 2009, now Pat. No. 8,303,485.

(30) Foreign Application Priority Data

Jun. 19, 2008  (JP) .................... 2008-160807
Oct. 17, 2008  (JP) .................... 2008-269048

(51) Int. Cl.
 *A61B 1/00* (2006.01)
 *A61B 19/00* (2006.01)
 *A61B 5/05* (2006.01)
 *H01F 1/00* (2006.01)

(52) U.S. Cl.
 USPC ........... 600/117; 600/114; 600/118; 600/407; 600/424; 128/899; 335/219

(58) Field of Classification Search .................. 600/101, 600/117–118, 407, 424; 128/899; 335/219
 See application file for complete search history.

(56) References Cited

U.S. PATENT DOCUMENTS

| 7,499,581 | B2* | 3/2009 | Tribble et al. ........ 382/141 |
| 7,507,940 | B2* | 3/2009 | Fournier et al. ........ 250/201.4 |
| 2003/0214580 | A1 | 11/2003 | Iddan |
| 2004/0138552 | A1 | 7/2004 | Harel et al. |
| 2005/0085696 | A1 | 4/2005 | Uchiyama et al. |
| 2005/0143648 | A1* | 6/2005 | Minai et al. ........ 600/410 |

(Continued)

FOREIGN PATENT DOCUMENTS

EP   1 723 898 A1   11/2006
EP   1 955 644 A1   8/2008

(Continued)

OTHER PUBLICATIONS

Partial European Search Report dated Oct. 15, 2009.

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

A magnetically guiding system includes: a capsule medical device that has a magnet provided therein; an information acquiring unit that acquires physical information about magnetic guiding of the capsule medical device; a magnetic field generating unit that generates a magnetic field for magnetically guiding the capsule medical device; and a control unit that sets a magnetic field condition based on the physical information acquired by the information acquiring unit and controls the magnetic field generating unit to generate a magnetic field corresponding to the magnetic field condition.

8 Claims, 27 Drawing Sheets

U.S. PATENT DOCUMENTS

| | | |
|---|---|---|
| 2006/0169293 A1 | 8/2006 | Yokoi et al. |
| 2006/0224063 A1* | 10/2006 | Segawa et al. ............... 600/424 |
| 2007/0021654 A1* | 1/2007 | Preidel et al. ............... 600/160 |
| 2007/0244388 A1 | 10/2007 | Sato et al. |
| 2007/0265496 A1 | 11/2007 | Kawano et al. |
| 2007/0299301 A1 | 12/2007 | Uchiyama et al. |
| 2008/0035521 A1 | 2/2008 | Takizawa et al. |
| 2008/0039688 A1* | 2/2008 | Minal et al. ............... 600/117 |
| 2008/0300453 A1* | 12/2008 | Aoki et al. ............... 600/103 |
| 2008/0306340 A1 | 12/2008 | Uchiyama et al. |
| 2009/0171190 A1* | 7/2009 | Uchiyama et al. ............ 600/424 |
| 2009/0326323 A1* | 12/2009 | Uchiyama et al. ............ 600/118 |
| 2010/0219825 A1* | 9/2010 | Sato et al. .................... 324/307 |

FOREIGN PATENT DOCUMENTS

| | | |
|---|---|---|
| EP | 1 967 137 A1 | 9/2008 |
| EP | 1 972 253 A1 | 9/2008 |
| EP | 2 033 569 A1 | 3/2009 |
| EP | 2 060 221 A1 | 5/2009 |
| EP | 2 090 215 A1 | 8/2009 |
| JP | 2004-255174 | 9/2004 |
| JP | 2005-081147 | 3/2005 |
| JP | 2008-6056 A | 1/2008 |
| JP | 2008-119253 A | 5/2008 |
| JP | 2008-178693 A | 8/2008 |
| WO | WO 99/18852 A1 | 4/1999 |
| WO | WO 2007/064013 A1 | 6/2007 |
| WO | WO 2007/074767 A1 | 7/2007 |
| WO | WO 2007/074888 A1 | 7/2007 |
| WO | WO 2007/077896 A1 | 7/2007 |
| WO | WO 2008/001810 A1 | 1/2008 |
| WO | WO 2008/029460 A1 | 3/2008 |
| WO | WO 2008/059773 A1 | 5/2008 |
| WO | WO 2009/001666 A1 | 12/2008 |

OTHER PUBLICATIONS

Non-Final Office Action of corresponding U.S. Appl. No. 12/486,399 dated Sep. 29, 2011.
Final Office Action of corresponding U.S. Appl. No. 12/486,399 dated Apr. 11, 2012.
Extended European Search Report dated Aug. 22, 2012 of corresponding Application No./Patent No. 11005099.4-2319 / 2392249.
Extended European Search Report dated Aug. 22, 2012 of corresponding Application No./Patent No. 11005100.0-2319 / 2392250.
Notice of Rejection dated Nov. 6, 2012 from corresponding Japanese Patent Application No. JP 2008-269048, together with an English language translation.
European Search Report dated Jan. 9, 2013 from corresponding European Patent Application No. EP 11 00 5205.7.

* cited by examiner

FIG.2

| DENSITY $\rho_{CP}$ OF CAPSULE MEDICAL DEVICE | MAGNETIC FIELD CONDITION |
|---|---|
| DENSITY RANGE R1 | OUTPUT PATTERN A1 |
| DENSITY RANGE R2 | OUTPUT PATTERN A2 |
| DENSITY RANGE R3 | OUTPUT PATTERN A3 |
| ⋮ | ⋮ |
| DENSITY RANGE Rn | OUTPUT PATTERN An |

FIG.11
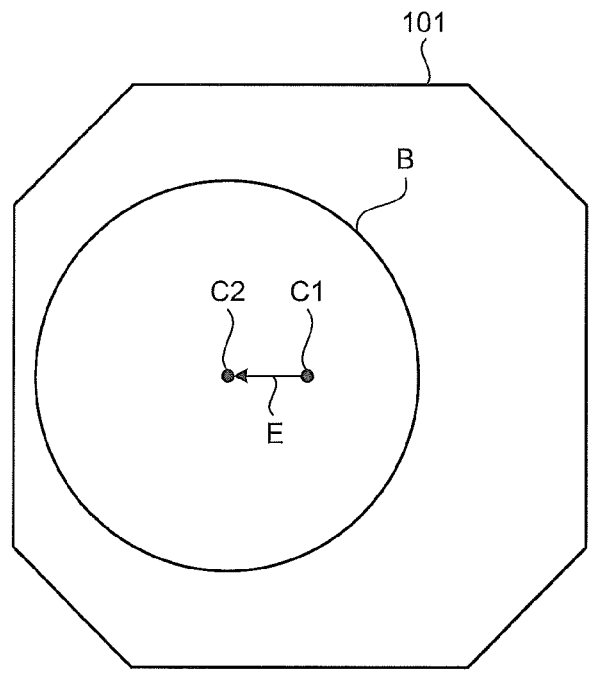
FIG.12
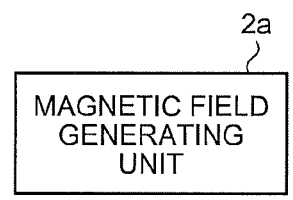
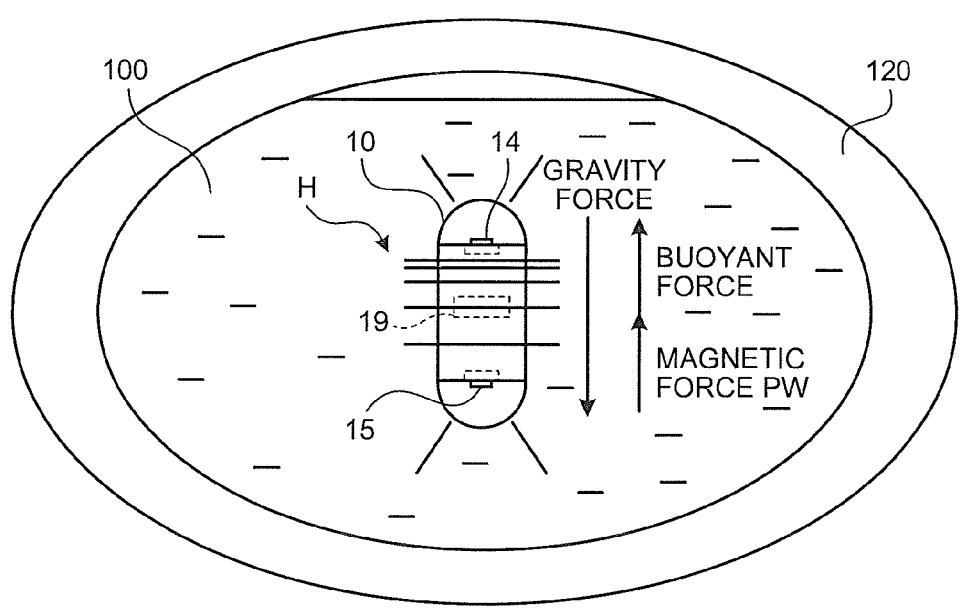

FIG.26
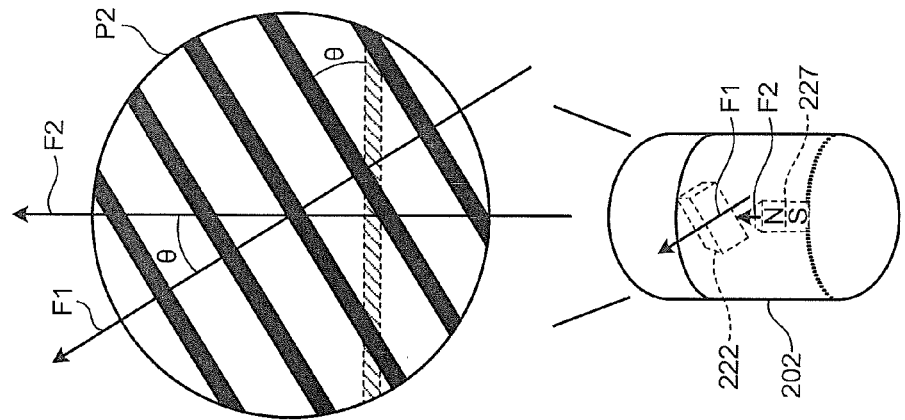
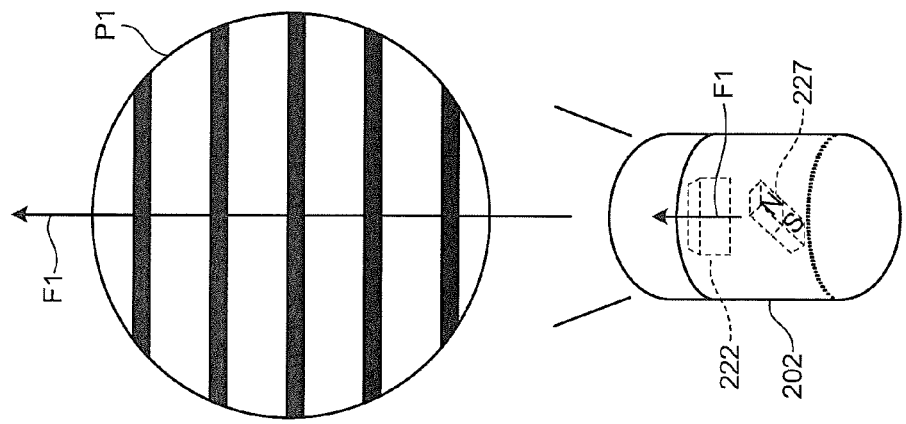

MAGNETICALLY GUIDING SYSTEM AND MAGNETICALLY GUIDING METHOD

CROSS-REFERENCE TO RELATED APPLICATIONS

This application is a Divisional Application of U.S. Ser. No. 12/486,399, filed on Jun. 17, 2009 now U.S. Pat. No. 8,303,485, which is based upon and claims the benefit of priority from Japanese Patent Applications No. 2008-160807, filed on Jun. 19, 2008, and No. 2008-269048, filed on Oct. 17, 2008, the entire contents of each of which are incorporated herein by reference.

BACKGROUND OF THE INVENTION

1. Field of the Invention

The present invention relates to a magnetically guiding system and a magnetically guiding method for magnetically guiding a medical device that is introduced into the body of a test subject.

2. Description of the Related Art

In the field of endoscopes, there have been capsule medical devices having image capturing functions and radio communication functions. A capsule medical device is introduced into the body of a test subject such as a patient via the oral route, to check the inside of an internal organ of the test subject. The capsule medical device inside the body of the test subject sequentially captures images of the inside of the internal organ (hereinafter also referred to as in-vivo images) at predetermined intervals, while moving in the internal organ through peristaltic movement. The capsule medical device then sequentially radio-transmits the in-vivo images to the outside. The capsule medical device inside the body of the test subject sequentially repeats the capture and radio transmission of the in-vivo images until it is excreted from the body of the test subject. In the end, the capsule medical device is excreted from the body of the test subject.

Each of the in-vivo images captured by the capsule medical device is received by a receiving device outside the body of the test subject, and is input to an image display device via the receiving device. The image display device displays each of the in-vivo images on its display screen. A user such as a medical doctor or a nurse observes the inside of the internal organ of the test subject through each of the in-vivo images displayed on the image display device. Based on the observation result, the user can make a diagnosis on the test subject.

In recent years, systems that magnetically guide a capsule medical device inside the body of a test subject have been proposed. As an example of such a magnetically guiding system, there is a system that magnetically guides a video capsule inside a human body located in an operating space surrounded by fourteen individual coils (see Japanese Patent Application Laid-open No. 2005-81147).

In a medical device guiding system disclosed in Japanese Patent Application Laid-open No. 2004-255174, a capsule medical device that has an image capturing function and a magnet enclosed inside a capsule-like casing is introduced into a digestive tract of a test subject, and a rotating magnetic field is applied to the capsule medical device inside the body of the test subject, so as to magnetically guide the capsule medical device to a desired position inside the body of the test subject. In this case, the capsule medical device inside the body of the test subject moves, as the magnet inside the capsule-like casing follows the rotating magnetic field applied from the outside.

SUMMARY OF THE INVENTION

A magnetically guiding system according to an aspect of the present invention includes a medical device that has a magnet; an information acquiring device that acquires physical information about magnetic guiding of the medical device; a magnetic field generating unit that generates a magnetic field for magnetically guiding the medical device; and a control unit that sets a magnetic field condition based on the physical information acquired by the information acquiring device and controls the magnetic field generating unit to generate the magnetic field corresponding to the magnetic field condition.

A magnetically guiding method according to another aspect of the present invention includes acquiring physical information about magnetic guiding of a medical device that includes a magnet; setting a magnetic field condition for a magnetic field to be applied to the medical device based on the acquired physical information; and applying the magnetic field corresponding to the set magnetic field condition to the medical device inside a test subject, so as to magnetically guide the medical device.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 schematically shows a specific example of a magnetic field condition table;

FIG. 11 is a schematic view showing an example of an image captured by the capsule medical device that is floating in the liquid while tilting;

FIG. 12 is a schematic view showing a situation where the capsule medical device introduced into the body of a test subject is magnetically guided;

FIG. 26 is a schematic view illustrating an operation by the checking device in accordance with the eighth embodiment of the present invention to measure the angle between the reference direction of a magnet provided in a capsule medical device and the reference direction of an image capturing unit;

DETAILED DESCRIPTION OF THE PREFERRED EMBODIMENTS

Figure 1:
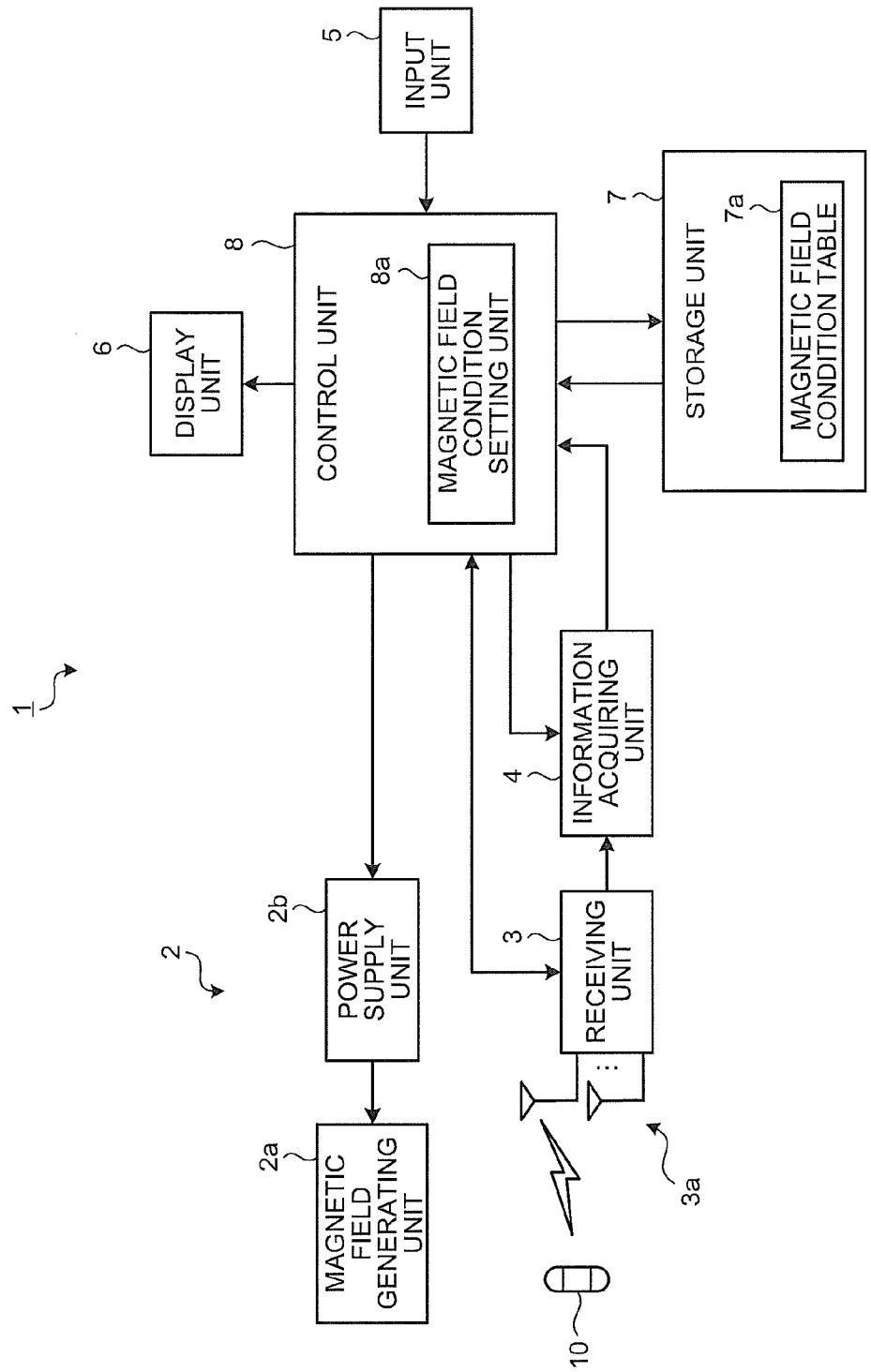
FIG. 1 is a block diagram schematically showing an example structure of a magnetically guiding system in accordance with a first embodiment of the present invention.

The following is a description of preferred embodiments of magnetically guided systems and magnetically guiding methods according to the present invention, with reference to the accompanying drawings. It should be noted that the present invention is not limited by the following embodiments. In the accompanying drawings, like components are denoted by like reference numerals.

FIG. 1 is a block diagram schematically showing an example structure of a magnetically guiding system in accordance with a first embodiment of the present invention. The magnetically guiding system in accordance with the first embodiment is a system that magnetically guides a capsule medical device 10 to be introduced into an internal organ of a test subject. As shown in FIG. 1, the magnetically guiding system includes a magnetically guiding unit 2, a receiving unit 3, an information acquiring unit 4, an input unit 5, a display unit 6, a storage unit 7, and a control unit 8.

The magnetically guiding unit 2 magnetically guides the capsule medical device 10 introduced into the internal organ of the test subject. The magnetically guiding unit 2 includes a magnetic field generating unit 2a that outputs a guiding magnetic field, and a power supply unit 2b that supplies electric power to the magnetic field generating unit 2a.

The magnetic field generating unit 2a may be embodied with the use of an electromagnet such as a Helmholtz coil. The magnetic field generating unit 2a outputs a guiding magnetic field based on the electric power supplied from the power supply unit 2b, and applies the guiding magnetic field to the capsule medical device 10. The magnetic field generating unit 2a magnetically guides the capsule medical device 10 by virtue of the action (such as magnetic attraction, magnetic repulsion, magnetic gradient, or magnetic torque) of the guiding magnetic field.

The power supply unit 2b supplies the electric power required for generating the guiding magnetic field to be applied to the capsule medical device 10, to the magnetic field generating unit 2a. More specifically, the power supply unit 2b includes one or more current signal generating unit(s) (not shown) corresponding to one or more electromagnet(s) (coil(s)) that configure the magnetic field generating unit 2a. Under the control of the control unit 8, the power supply unit 2b generates current signals of various patterns to apply the signals to the magnetic field generating unit 2a, and supplies alternating currents of various patterns to the magnetic field generating unit 2a. In accordance with the patterns of the current signals supplied from the power supply unit 2b, the magnetic field generating unit 2a applies guiding magnetic fields of various output patterns to the capsule medical device 10.

The receiving unit 3 receives an image that is captured by the capsule medical device 10. More specifically, the receiving unit 3 includes receiving antennas 3a, and receives a radio signal from the capsule medical device 10 via at least one of the receiving antennas 3a. The receiving unit 3 performs predetermined communication processing such as demodulation on the radio signal received from the capsule medical device 10, so as to demodulate the radio signal to an image signal. The image signal contains at least the data of the image captured by the capsule medical device 10. The receiving unit 3 then transmits the image signal from the capsule medical device 10 to the information acquiring unit 4 and the control unit 8.

Based on the image received by the receiving unit 3 from the capsule medical device 10, the information acquiring unit 4 acquires physical information about the magnetic guiding of the capsule medical device 10. More specifically, from the receiving unit 3, the information acquiring unit 4 obtains the image signal demodulated by the receiving unit 3 (that is, the image signal transmitted from the capsule medical device 10). The information acquiring unit 4 performs predetermined image processing on the image signal, so as to generate the image captured by the capsule medical device 10. Based on the generated image captured by the capsule medical device 10, the information acquiring unit 4 calculates the physical information about the magnetic guiding of the capsule medical device 10. In this manner, the information acquiring unit 4 acquires the physical information about the magnetic guiding of the capsule medical device 10. The information acquiring unit 4 then transmits the physical information to the control unit 8.

The physical information about the magnetic guiding of the capsule medical device 10 relates to the field conditions of the guiding magnetic field to be applied to the capsule medical device 10 when the capsule medical device 10 is magnetically guided. For example, the physical information contains the information indicating the density of the capsule medical device 10 or the position of the center of gravity of the capsule medical device 10.

The input unit 5 may be embodied with the use of input devices such as a mouse and a keyboard, and inputs various kinds of information into the control unit 8 in accordance with input operations by users. More specifically, the input unit 5 inputs instruction information directed to the control unit 8 and physical information and the likes required for calculating the physical information about the magnetic guiding of the capsule medical device 10. The physical information to be input by the input unit 5 includes the volume and mass of the capsule medical device 10, the curvature radius of the dome-like part of the capsule medical device 10, the density of the liquid to be introduced together with the capsule medical device 10 into the test subject, and the likes.

The display unit 6 may be embodied with the use of a display device such as a CRT display or a liquid crystal display. The display unit 6 displays various kinds of information instructed by the control unit 8. Under the control of the control unit 8, the display unit 6 displays the input information supplied from the input unit 5, the image that is captured by the capsule medical device 10 and is received by the receiving unit 3, the physical information acquired by the information acquiring unit 4 (that is, the physical information about the magnetic guiding of the capsule medical device 10), the information indicating the magnetically guided state of the capsule medical device 10, or the like.

The storage unit 7 may be embodied with the use of a storage medium that stores information in a rewritable fashion, such as a RAM, an EEPROM, a flash memory, or a hard disk. The storage unit 7 stores various kinds of information instructed to store by the control unit 8, and transmits information among the stored various kinds of information to the control unit 8 in accordance with a read instruction issued from the control unit 8. More specifically, under the control of the control unit 8, the storage unit 7 appropriately stores or updates the physical information that is input by the input unit 5, the image captured by the capsule medical device 10, the physical information about the magnetic guiding of the capsule medical device 10, or the like.

The storage unit 7 also stores beforehand a magnetic field condition table 7a designed for setting the magnetic field conditions for the guiding magnetic field. FIG. 2 is a schematic view showing a specific example of the magnetic field condition table. The magnetic field condition table 7a is a data table that associates the physical information about the magnetic guiding of the capsule medical device 10 with the magnetic field conditions for the guiding magnetic field. More specifically, the magnetic field condition table 7a stores the density ranges R1 through Rn of the density $\rho_{CP}$ of the capsule medical device 10, and the output patterns A1 through An as the magnetic field conditions for the guiding magnetic field, as shown in FIG. 2. In this case, the density ranges R1 through Rn of the density $\rho_{CP}$ are associated with the output patterns A1 through An of the guiding magnetic field, respectively. The density $\rho_{CP}$ is an example of the physical information about the magnetic guiding of the capsule medical device 10, and is calculated by the information acquiring unit 4. The output patterns A1 through An each associated with the density ranges R1 through Rn of the density $\rho_{CP}$ represent the optimum conditions (the optimum output patterns) for the guiding magnetic field that varies with the density range of the capsule medical device 10.

The control unit 8 controls the operations of the magnetically guiding unit 2, the receiving unit 3, the information acquiring unit 4, the input unit 5, the display unit 6, and the storage unit 7, which are components of the magnetically guiding system 1. The control unit 8 also controls signal inputs and outputs between those components. More specifically, in accordance with the instruction information that is input from the input unit 5, the control unit 8 controls the receiving operation of the receiving unit 3, the information acquiring operation of the information acquiring unit 4, the displaying operation of the display unit 6, the storing operation of the storage unit 7, and the likes. In this case, the control unit 8 stores various kinds of information such as the information acquired by the information acquiring unit 4 (that is, the physical information about the magnetic guiding of the capsule medical device 10) or the information input from the input unit 5, into the storage unit 7. The control unit 8 then causes the display unit 6 to display the various kinds of information, when appropriate. The control unit 8 also has an image processing function, and performs predetermined image processing on the image signal acquired from the receiving unit 3 so as to generate the image captured by the capsule medical device 10. The control unit 8 then causes the display unit 6 to display the generated image, and stores the generated image into the storage unit 7. The control unit 8 reads out the various kinds of information stored in the storage unit 7, when necessary.

The control unit 8 also includes a magnetic field condition setting unit 8a that sets the magnetic field conditions for the guiding magnetic field. The magnetic field condition setting unit 8a obtains the information acquired by the information acquiring unit 4, that is, the physical information about the magnetic guiding of the capsule medical device 10, from the information acquiring unit 4. Based on the physical information, the magnetic field condition setting unit 8a sets the magnetic field conditions for the guiding magnetic field. In this case, the magnetic field condition setting unit 8a selects the magnetic field condition corresponding to the obtained physical information from the magnetic field condition table 7a stored in the storage unit 7, and sets the selected magnetic field condition as the magnetic field condition for the guiding magnetic field. The control unit 8 controls the magnetically guiding unit 2 to apply the guiding magnetic field satisfying the set magnetic field condition to the capsule medical device 10. In this manner, the capsule medical device 10 is magnetically guided. In this case, the control unit 8 controls the power supply unit 2b to apply the current signal of the pattern satisfying the magnetic field condition to the magnetic field generating unit 2a, and controls the guiding magnetic field generating operation of the magnetic field generating unit 2a by controlling the power supply unit 2b. After that, the control unit 8 uses the set magnetic field condition as the initial condition for the guiding magnetic field. In accordance with the instruction information that is input from the input unit 5, the control unit 8 controls the current signal to be applied from the power supply unit 2b to the magnetic field generating unit 2a, and controls the guiding magnetic field generating operation of the magnetic field generating unit 2a by controlling the current signal. In this manner, the control unit 8 continuously controls the magnetic guiding of the capsule medical device 10, starting from controlling the magnetically guided state of the capsule medical device 10 following the guiding magnetic field satisfying the initial condition.

Figure 3:
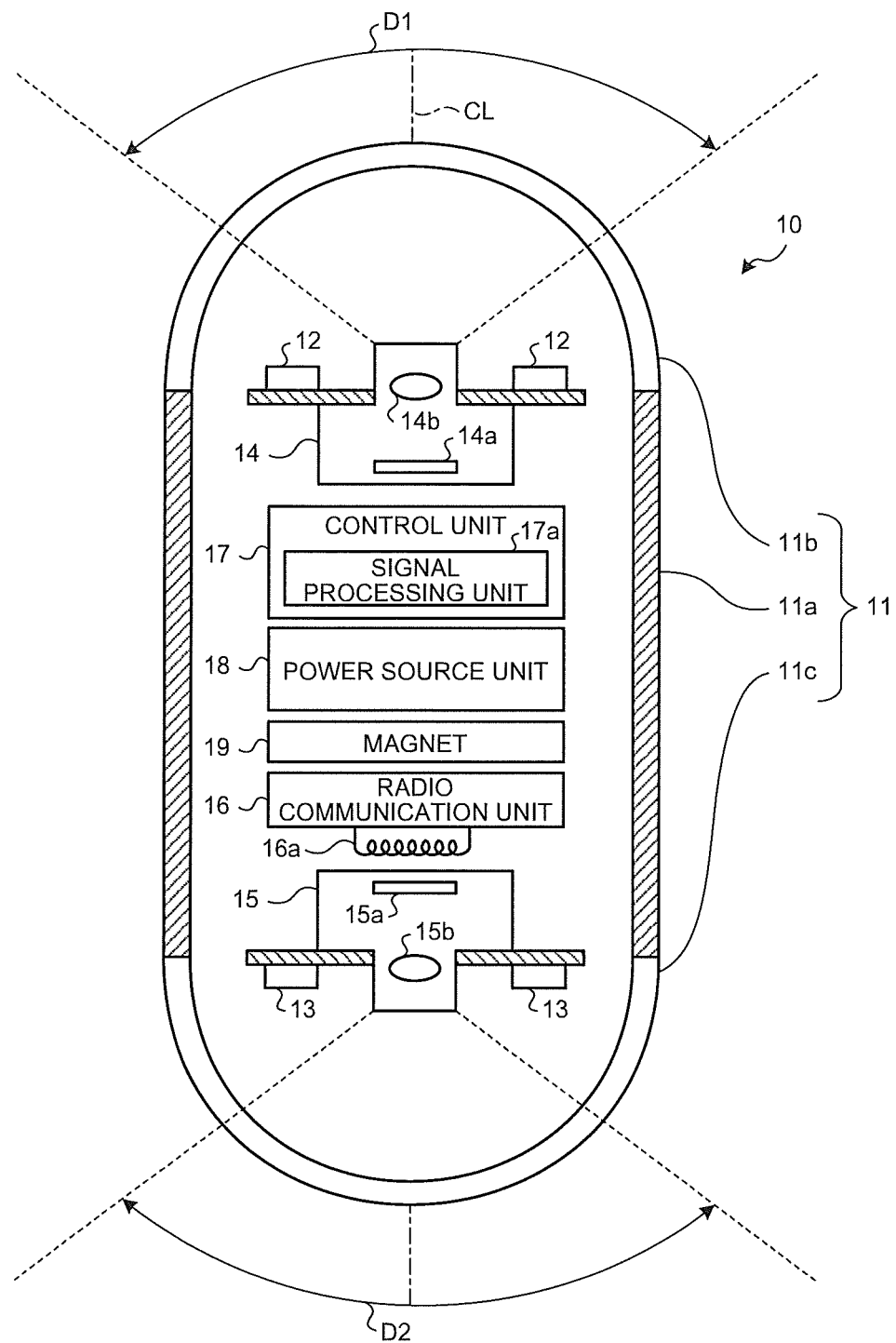
FIG. 3 is a schematic cross-sectional view showing an example structure of a capsule medical device to be magnetically guided.

Next, the structure of the capsule medical device 10 to be magnetically guided will be described. FIG. 3 is a schematic cross-sectional view showing an example structure of the capsule medical device to be magnetically guided. As shown in FIG. 3, the capsule medical device 10 includes a capsule-like casing 11 that is the exterior packaging designed in such a size as to be easily introduced into an internal organ of a test subject such as a patient, illuminating units 12 and 13 that illuminate different photographic subjects in different directions, and image capturing units 14 and 15 that capture images of the different photographic subjects. The capsule medical device 10 also includes a radio communication unit 16 that radio-transmits images captured by the image capturing units 14 and 15 to the outside, a control unit 17 that controls the components of the capsule medical device 10, and a power source unit 18 that supplies electric power to each of the components of the capsule medical device 10. The capsule medical device 10 further includes a magnet 19 for operating in accordance with the guiding magnetic field applied by the magnetic field generating unit 2a.

The capsule-like casing 11 is an exterior casing that is formed in such a size as to be easily introduced into an internal organ of a test subject such as a patient. The capsule-like casing 11 includes a cylindrical casing 11a having both opening ends closed by dome-like casings 11b and 11c. The dome-like casings 11b and 11c are dome-like optical members that are transparent to illuminating light such as visible light emitted from the illuminating units 12 and 13. The cylindrical casing 11a is a colored casing that is substantially not transparent to visible light. The capsule-like casing 11 formed with the cylindrical casing 11a and the dome-like casings 11b and 11c encloses the illuminating units 12 and 13, the image capturing units 14 and 15, the radio communication unit 16, the control unit 17, the power source unit 18, and the magnet 19 in a liquid-tight manner.

The illuminating units 12 and 13 may be embodied with the use of light emitting devices such as LEDs, and illuminate the respective image viewing fields D1 and D2 of the image capturing units 14 and 15 that capture images in different directions from each other. More specifically, the illuminating unit 12 emits illuminating light onto the image viewing field D1 of the image capturing unit 14, and illuminates the subject of the image capturing unit 14 through the dome-like casing 11b. The illuminating unit 13 emits illuminating light onto the image viewing field D2 of the image capturing unit 15, and illuminates the subject of the image capturing unit 15 through the dome-like casing 11c.

The image capturing units 14 and 15 capture images in different directions from each other. More specifically, the image capturing unit 14 includes a solid-state image sensor 14a such as a CMOS image sensor or a CCD, and an optical system 14b such as a lens that forms an image of the subject located in the image viewing field D1 on the light receiving face of the solid-state image sensor 14a. The image capturing unit 14 captures an image of the subject located in the image viewing field D1 illuminated by the illuminating unit 12. The image capturing unit 15 includes a solid-state image sensor 15a such as a CMOS image sensor or a CCD, and an optical system 15b such as a lens that forms an image of the subject located in the image viewing field D2 on the light receiving face of the solid-state image sensor 15a. The image capturing unit 15 captures an image of the subject located in the image viewing field D2 illuminated by the illuminating unit 13.

In a case where the capsule medical device 10 is a twin-lens capsule medical device that captures images from the front side and the rear side in the long axis direction, as shown in FIG. 3, the optic axes of the image capturing units 14 and 15 are substantially parallel to or identical to a long axis CL that is the central axis of the capsule-like casing 11 in the longitudinal direction. The image viewing fields D1 and D2 of the image capturing units 14 and 15 extend in the opposite directions from each other.

The radio communication unit 16 has an antenna 16a, and sequentially radio-transmits images captured by the image capturing units 14 and 15 through the antenna 16a. More specifically, the radio communication unit 16 obtains the image signal of an image captured by the image capturing unit 14 or 15 from the control unit 17. The radio communication unit 16 performs modulation or the like on the image signal, so as to generate a radio signal formed by modulating the image signal. The radio communication unit 16 then transmits the radio signal to the external receiving unit 3 (see FIG. 1) through the antenna 16a.

The control unit 17 controls the illuminating units 12 and 13, the image capturing units 14 and 15, and the radio communication unit 16, and also controls inputs and outputs of signals among those components. More specifically, the control unit 17 causes the image capturing unit 14 to capture an image of the subject located in the image viewing field D1 illuminated by the illuminating unit 12, and causes the image capturing unit 15 to capture an image of the subject located in the image viewing field D2 illuminated by the illuminating unit 13. The control unit 17 also causes the radio communication unit 16 to sequentially radio-transmit images captured by the image capturing units 14 and 15 in chronological order.

The control unit 17 also includes a signal processing unit 17a. The signal processing unit 17a obtains the image data about the image viewing field D1 from the image capturing unit 14. Every time the image data is obtained, the signal processing unit 17a performs predetermined signal processing on the image data, so as to generate an image signal containing the image data about the image viewing field D1. Likewise, the signal processing unit 17a obtains the image data about the image viewing field D2 from the image capturing unit 15. Every time the image data is obtained, the signal processing unit 17a performs predetermined signal processing on the image data, so as to generate an image signal containing the image data about the image viewing field D2. Each of the image signals generated by the signal processing unit 17a is sequentially transmitted to the radio communication unit 16.

The power source unit 18 includes a storage unit such as a button-type battery cell or a capacitor, and a switching unit such as a magnetic switch. The power source unit 18 switches the power source on and off in accordance with a magnetic field applied from the outside. When the power source is switched on, the power source unit 18 appropriately supplies the power from the storage unit to the components (the illuminating units 12 and 13, the image capturing units 14 and 15, the radio communication unit 16, and the control unit 17) of the capsule medical device 10. When the power source is switched off, the power source unit 18 stops the power supply to the components of the capsule medical device 10.

The magnet 19 is provided to enable the magnetic guiding of the capsule medical device 10 by a magnetic field applied from the outside. More specifically, the magnet 19 is placed in a predetermined position inside the capsule-like casing 11, and forms a magnetic field in a predetermined direction (such as the long axis direction or the radial direction of the capsule-like casing 11). This magnet 19 operates in accordance with a magnetic field induced from outside of the capsule-like casing 11, or the guiding magnetic field applied by the magnetic field generating unit 2a shown in FIG. 1. As a result, the capsule medical device 10 is magnetically guided. In this case, the capsule medical device 10 makes at least one of a posture changing action and a displacement action, by virtue of the effect of the magnet 19. Alternatively, the capsule medical device 10 is maintained in a stopped state at a predetermined position, by virtue of the effect of the magnet 19.

Figure 4:
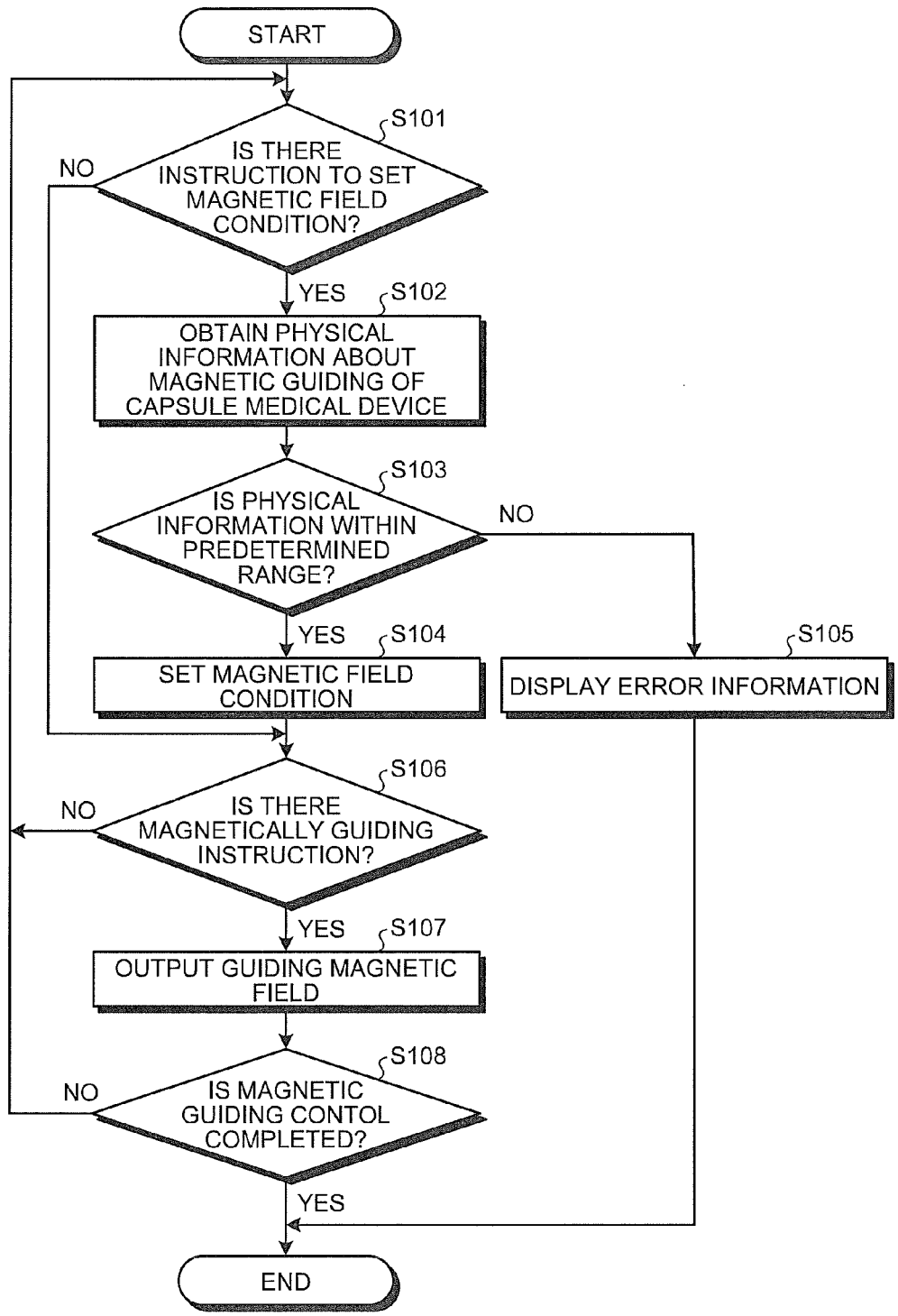
FIG. 4 is a flowchart illustrating an example of a magnetically guiding method in accordance with the first embodiment of the present invention.

Next, the operation of the magnetically guiding system 1 in accordance with the first embodiment of the present invention will be described. FIG. 4 is a flowchart showing an example of a magnetically guiding method in accordance with the first embodiment of the present invention. The magnetically guiding system 1 in accordance with the first embodiment magnetically guides the capsule medical device 10, according to the procedures shown in FIG. 4.

As shown in FIG. 4, the control unit 8 of the magnetically guiding system 1 determines whether there is an instruction to set a magnetic field condition for magnetically guiding the capsule medical device 10 (step S101). In a case where the input unit 5 has input instruction information to instruct the setting of a magnetic field condition, the control unit 8 determines from the instruction information that there is an instruction to set a magnetic field condition in step S101. In a case where such instruction information has not been input, the control unit 8 determines that there is not an instruction to set a magnetic field condition.

If the control unit 8 determines in step S101 that there is an instruction to set a magnetic field condition (step S101, Yes), the control unit 8 obtains the physical information about the magnetic guiding of the capsule medical device 10 to be magnetically guided (step S102). In step S102, the control unit 8 controls the receiving unit 3 to receive an image captured by the capsule medical device 10 in a floating or sunken state in a liquid. The control unit 8 also controls the information acquiring unit 4 to calculate the physical information about the magnetic guiding of the capsule medical device 10, based on the image that is captured by the capsule medical device 10 and is received by the receiving unit 3. Under the control of the control unit 8, the information acquiring unit 4 calculates the physical information about the magnetic guiding of the capsule medical device 10, and transmits the calculated physical information to the control unit 8. In this manner, the control unit 8 obtains the physical information about the magnetic guiding of the capsule medical device 10.

The control unit 8 then determines whether the physical information obtained in step S102 is within a predetermined range (step S103). In step S103, if the physical information is the density $\rho_{CP}$ of the capsule medical device 10, the magnetic field condition setting unit 8a reads the magnetic field condition table 7a from the storage unit 7, and determines whether the density $\rho_{CP}$ falls into one of the density ranges R1 through Rn.

If the physical information obtained in step S102 is within the predetermined range (step S103, Yes), the control unit 8 sets a magnetic field condition for magnetically guiding the capsule medical device 10 (step S104). In step S104, the magnetic field condition setting unit 8a sets the magnetic field condition for magnetically guiding the capsule medical device 10, based on the physical information about the magnetic guiding of the capsule medical device 10 obtained from the information acquiring unit 4.

More specifically, in a case where the physical information is the density $\rho_{CP}$ of the capsule medical device 10, the magnetic field condition setting unit 8a reads the magnetic field condition table 7a from the storage unit 7. While referring to the magnetic field condition table 7a, the magnetic field condition setting unit 8a sets the magnetic field condition suited for the capsule medical device 10 having the density $\rho_{CP}$. In this case, the magnetic field condition setting unit 8a determines whether the density $\rho_{CP}$ falls into one of the density ranges R1 through Rn in the magnetic field condition table 7a. The magnetic field condition setting unit 8a then selects the output pattern of the magnetic field (one of the output patterns A1 through An) associated with the determined density range as the magnetic field condition. For example, if the density $\rho_{CP}$ falls into the density range R1, the magnetic field condition setting unit 8a selects the output pattern A1 as the magnetic field condition. If the density $\rho_{CP}$ falls into the density range Rn, the magnetic field condition setting unit 8a selects the output pattern An as the magnetic field condition.

In a case where the physical information is the position of the center of gravity of the capsule medical device 10, the magnetic field condition setting unit 8a sets a magnetic field condition suited for the capsule medical device 10 having the position of the center of gravity. In this case, the magnetic field condition setting unit 8a sets the initial magnetic field direction and the initial field intensity of the magnetic field to be applied to the capsule medical device 10, based on the relative shift amount and direction of the position of the center of gravity with respect to the long axis CL of the capsule medical device 10 shown in FIG. 3. Although the position of the center of gravity is shifted from the long axis CL, the capsule medical device 10 subjected to the guiding magnetic field having the initial magnetic field direction and the initial field intensity floats upright in the liquid (or stands in such a manner that the long axis CL is substantially parallel to the vertical direction of the capsule medical device 10).

If the control unit 8 determines that the physical information obtained in step S102 is not within the predetermined range (step S103, No), the magnetic field condition setting unit 8a determines that the density $\rho_{CP}$ is outside the density ranges R1 through Rn defined in the magnetic field condition table 7a, for example. After that, the control unit 8 causes the display unit 6 to display error information (step S105), and ends this operation. In step S105, the control unit 8 causes the display unit 6 to display the error information indicating that the density $\rho_{CP}$ is outside the density ranges R1 through Rn defined in the magnetic field condition table 7a.

After setting the magnetic field condition for magnetically guiding the capsule medical device 10 in step S104 as described above, the control unit 8 determines whether there is an instruction to magnetically guide the capsule medical device 10 (step S106). In a case where instruction information to magnetically guide the capsule medical device 10 has been input by the input unit 5, the control unit 8 determines that there is an instruction to magnetically guide the capsule medical device 10, based on the instruction information in step S106. In a case where such instruction information has not been input, the control unit 8 determines that there is not an instruction to magnetically guide the capsule medical device 10.

If the control unit 8 determines that there is an instruction to magnetically guide the capsule medical device 10 in step S106 (step S106, Yes), the control unit 8 controls the magnetically guiding unit 2 to output a guiding magnetic field to the capsule medical device 10 to be magnetically guided (step S107). In step S107, the control unit 8 controls the magnetic field generating unit 2a and the current supply unit 2b to apply the guiding magnetic field satisfying the magnetic field condition (an output pattern, field intensity, a magnetic field direction, or the like) set in step S104 to the capsule medical device 10. As a result, the capsule medical device 10 in the liquid is magnetically guided in the initial state, according to the guiding magnetic field. The control unit 8 then controls the magnetic field generating unit 2a and the current supply unit 2b to further apply the guiding magnetic field based on the instruction information input from the input unit 5 to the capsule medical device 10 in the initial magnetically guided state. In this manner, the control unit 8 continuously controls the magnetic guiding of the capsule medical device 10, starting from the initial magnetically guided state of the capsule medical device 10.

After that, the control unit 8 determines whether to end the magnetically guiding control operation for the capsule medical device 10 (step S108). In a case where instruction information to end the operation has been input by the input unit 5, the control unit 8 determines to end the operation based on the instruction information (step S108, Yes), and then ends this operation. In a case where such instruction information to end the operation has not been input, the control unit 8 determines not to end the operation (step S108, No). The control unit 8 then returns to step S101, and repeats the procedures of step S101 and steps that follow.

If the control unit 8 determines that there is not an instruction to set a magnetic field condition in the above step S101 (step S101, No), the control unit 8 skips steps S102 through S105, and moves on to step S106. The control unit 8 then repeats the procedures of step S106 and steps that follow. If the control unit 8 determines that there is not an instruction to magnetically guide the capsule medical device 10 in step S106 (step S106, No), the control unit 8 returns to step S101, and repeats the procedures of step S101 and steps that follow.

Next, a specific operation of the magnetically guiding system 1 during the procedure of the above step S102 will be described by taking an example case where the physical information about the magnetic guiding of the capsule medical device 10 is at least one of the density $\rho_{CP}$ and the gravity center position GP of the capsule medical device 10.

Figure 5:
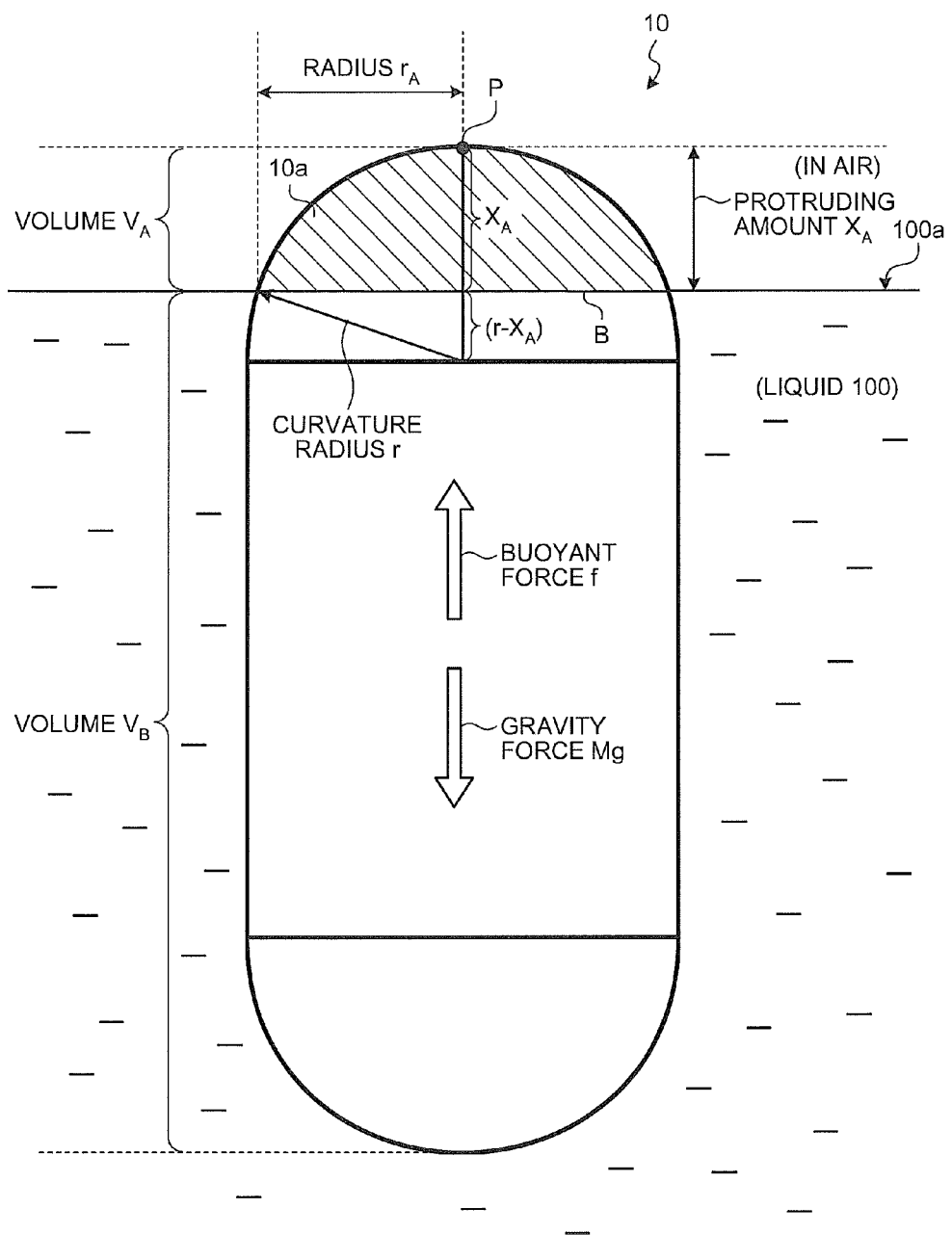
FIG. 5 is a schematic view showing an example of the capsule medical device that is floating in a liquid, with an image viewing field facing vertically upward.
Figure 6:
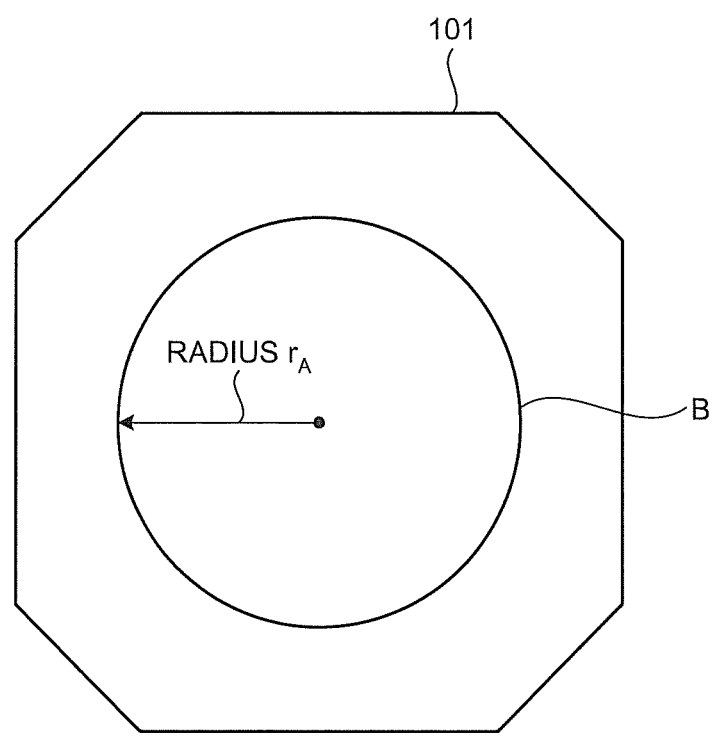
FIG. 6 is a schematic view showing an example of an image captured by the capsule medical device that is floating in the liquid, with an image viewing field facing vertically upward.

The following is a detailed description of the acquirement of the density $\rho_{CP}$ of the capsule medical device 10 observed in a case where the capsule medical device 10 can float on the liquid surface, with an image viewing field facing vertically upward. FIG. 5 is a schematic view showing the capsule medical device floating in a liquid, with an image viewing field facing vertically upward. FIG. 6 is a schematic view showing an image captured by the capsule medical device that is floating on the liquid, with an image viewing field facing vertically upward.

As shown in FIG. 5, where the capsule medical device 10 is floating on the liquid surface 100a of a liquid 100, the gravity force Mg acting on the capsule medical device 10 equals the buoyant force f acting on the capsule medical device 10 from the liquid 100. In short, the gravity force Mg is equal to the buoyant force f. Here, the gravity force Mg is the product of the density $\rho_{CP}$ and volume $V_{CP}$ the capsule medical device 10. The buoyant force f is the product of the density $\rho_{LIQ}$ of the liquid 100 and the volume $V_B$ of the portion of the capsule medical device 10 under the liquid surface 100a. Accordingly, the following equation (1) is established:

$$\rho_{CP} = (V_B/V_{CP}) \times \rho_{LIQ} \qquad (1)$$

The volume $V_B$ of the portion of the capsule medical device 10 under the liquid surface 100a is calculated by subtracting the volume $V_A$ of the protruding portion 10a (the shaded area in FIG. 5) protruding from the liquid surface 100a from the total volume $V_{CP}$ of the capsule medical device 10. Accordingly, the following equation (2) is established:

$$V_B = V_{CP} - V_A \qquad (2)$$

Also, the volume $V_A$ of the protruding portion 10a can be calculated by the formula expressed by the following equation (3):

$$V_A = 1/3 \times \pi \times X_A^2 \times (3 \times r - X_A) \qquad (3)$$

In the equation (3), $X_A$ represents the distance from the liquid surface 100a to the top P of the dome-like protruding portion 10a, and is equivalent to the protruding amount of the capsule medical device 10 above the liquid surface 100a, as shown in FIG. 5. Meanwhile, r represents the curvature radius of both dome-like end portions (the dome-like casings 11b and 11c shown in FIG. 3) of the exterior of the capsule medical device 100. The curvature radius r is input as one kind of physical information about the capsule medical device 10 by the input unit 5.

The capsule medical device 10 floating in the liquid 100 captures the image 101 shown in FIG. 6, with an image viewing field facing vertically upward. The image 101 captured by the capsule medical device 10 includes the boundary portion B between the liquid surface 100a of the liquid 100 and the exterior of the capsule medical device 10 as the subject. The boundary portion B has a circular shape as shown in FIG. 6, when the capsule medical device 10 floating in the liquid 100 floats upright as shown in FIG. 5. If the liquid 100 is a colored liquid, the boundary portion B is more clearly shown in the image 101.

The information acquiring unit 4 acquires the image signal of the image 101 captured by the capsule medical device 10 from the receiving unit 3. Based on the acquired image 101, the information acquiring unit 4 calculates the density $\rho_{CP}$ as an example of the physical information about the magnetic guiding of the capsule medical device 10. In this case, the information acquiring unit 4 first calculates a radius $r_A$ of the boundary portion B in the image 101, based on a preset scale equivalent to one pixel. The information acquiring unit 4 then calculates the protruding amount $X_A$ of the capsule medical device 10 above the liquid surface 100a, based on the calculated radius $r_A$ of the boundary portion B and the curvature radius r of the capsule medical device 10. More specifically, using the radius $r_A$ of the boundary portion B and the curvature radius r, the information acquiring unit 4 calculates the difference $(r - X_A)$ between the curvature radius r and the protruding amount $X_A$, according to the Pythagorean theorem. The information acquiring unit 4 then subtracts the difference $(r - X_A)$ from the curvature radius r, to calculate the protruding amount $X_A$ calculated in this manner. Using the protruding amount $X_A$, the volume $V_{CP}$ of the capsule medical device 100 input beforehand by the input unit 5, and the density $\rho_{LIQ}$ of the liquid 100, the information acquiring unit 4 calculates the density $\rho_{CP}$ of the capsule medical device 10, according to the equations (1) through (3). The information acquiring unit 4 acquires the density $\rho_{CP}$ of the capsule medical device 10 calculated in this manner as the physical information about the magnetic guiding of the capsule medical device 10.

By performing the above operation to calculate the density of the capsule medical device 10, the information acquiring unit 4 can acquire the density $\rho_{CP}$ as the physical information about the magnetic guiding of the capsule medical device 10 in both situations where the capsule medical device 10 has already been introduced into an internal organ of the test subject and where the capsule medical device 10 has not been introduced thereinto.

More specifically, in a case where the density $\rho_{CP}$ of the capsule medical device 10 is acquired before the capsule medical device 10 is introduced into an internal organ of the test subject, the capsule medical device 10 and an appropriate amount of liquid 100 are put into a predetermined container, so that the capsule medical device 10 floats on the liquid surface 100*a* of the liquid 100 in the container. In this situation, the receiving unit 3 receives the image 101 captured by the capsule medical device 10 floating in the liquid 100 in the container. Based on the image 101 received by the receiving unit 3, the information acquiring unit 4 calculates the density $\rho_{CP}$ of the capsule medical device 10. After that, the liquid 100 and the capsule medical device 10 are introduced into an internal organ of the test subject.

In this operation to calculate the density of the capsule medical device 10, this container is a hollow container that has an internal diameter that is greater than the external diameter of the capsule medical device 10, and has a depth that is greater than the length of the capsule medical device 10 in its long axis direction. The liquid 100 is a liquid that has higher density than the capsule medical device 10. For example, the liquid 100 is a liquid harmless to humans, such as water or isotonic sodium chloride solution in which the capsule medical device 10 can float within an internal organ of a test subject.

In a case where the density $\rho_{CP}$ of the capsule medical device 10 is acquired after the capsule medical device 10 is introduced into an internal organ of the test subject, the capsule medical device 10 and an appropriate amount of liquid 100 are introduced into an internal organ of the test subject via the oral route, so that the capsule medical device 10 floats on the liquid surface 100*a* of the liquid 100 in the internal organ of the test subject. In this situation, the receiving unit 3 receives the image 101 captured by the capsule medical device 10 floating in the liquid 100 in the internal organ. Based on the image 101 received by the receiving unit 3, the information acquiring unit 4 calculates the density $\rho_{CP}$ of the capsule medical device 10 in the above described manner.

Figure 7:
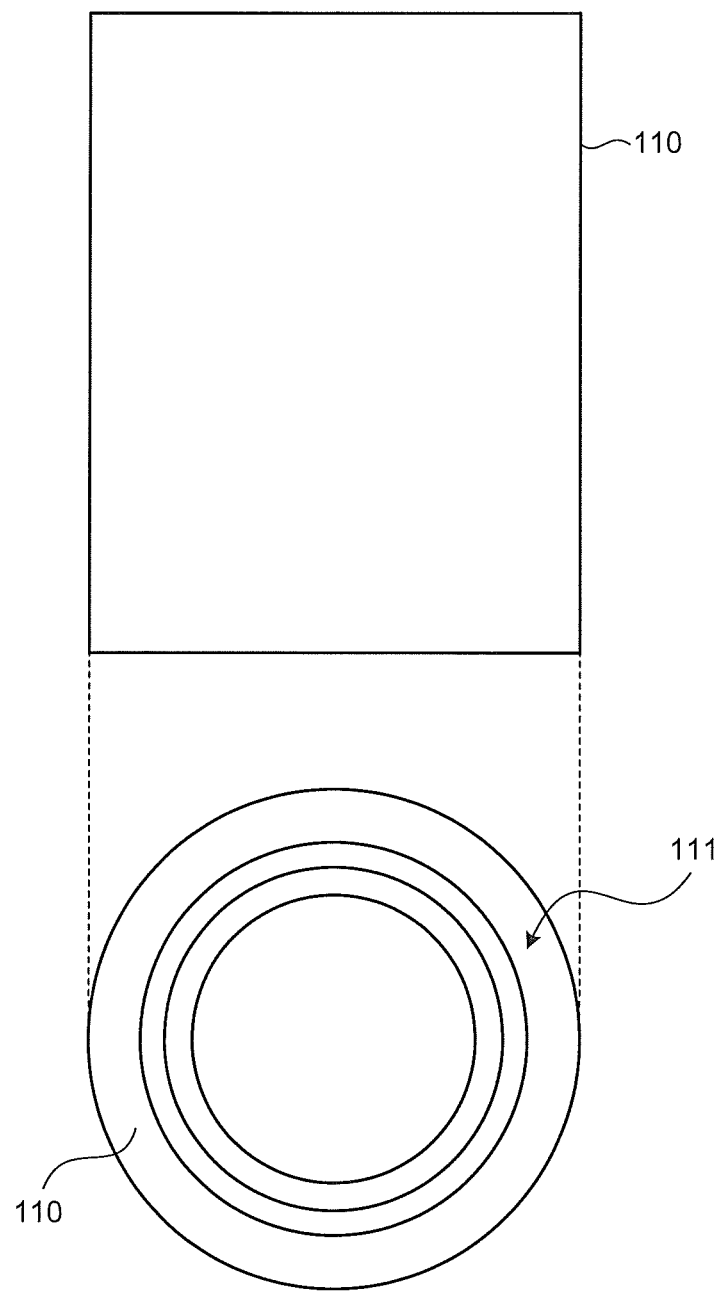
FIG. 7 is a schematic view showing an example of a container in which the capsule medical device floats on the liquid surface.
Figure 8:
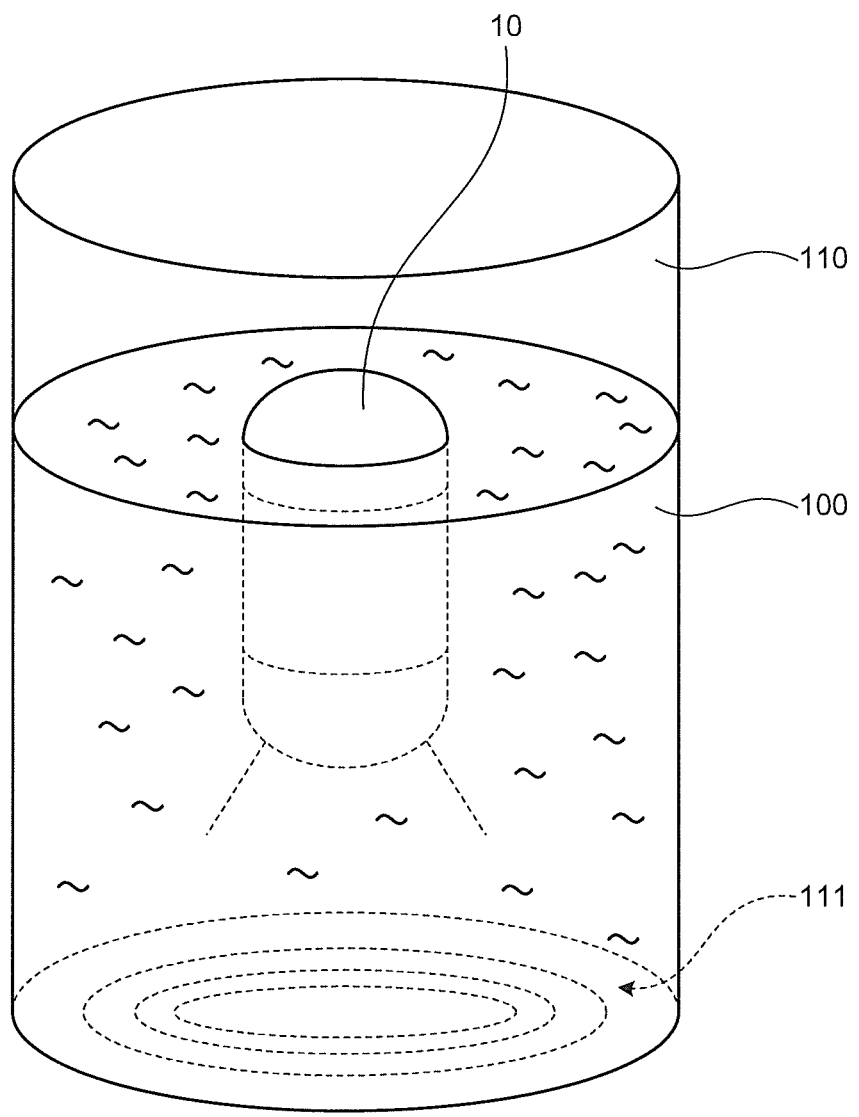
FIG. 8 is a schematic view showing a situation where the capsule medical device is floating in the liquid in the container, with an image viewing field facing vertically downward.
Figure 9:
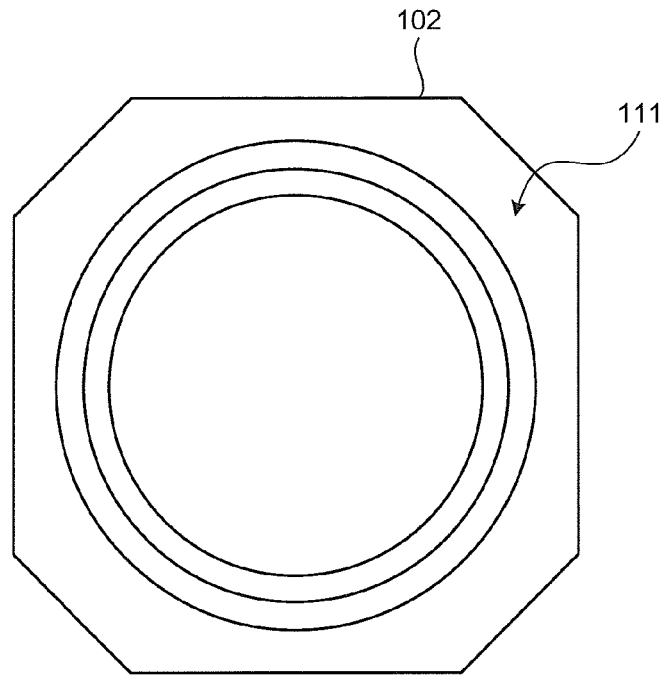
FIG. 9 is a schematic view showing an example of an image captured by the capsule medical device that is floating in the liquid, with an image viewing field facing vertically downward.

The following is a detailed description of the acquirement of the density $\rho_{CP}$ of the capsule medical device 10 observed in a case where the capsule medical device 10 can float on the liquid surface, with an image viewing field facing vertically downward. FIG. 7 is a schematic view showing an example of the container in which the capsule medical device floats on the liquid surface. FIG. 8 is a schematic view illustrating a situation where the capsule medical device is floating in a liquid in the container, with an image viewing field facing vertically downward. FIG. 9 is a schematic view showing an example of an image captured by the capsule medical device that is floating in the liquid, with an image viewing field facing vertically downward.

As shown in FIG. 7, the container 110 is a cylindrical hollow container, for example. The container 110 has an internal diameter that is greater than the external diameter of the capsule medical device 10, and has a depth that is greater than the length of the capsule medical device 10 in the long axis direction. The container 110 also has marks 111 drawn on the bottom. The marks 111 are formed with concentric circles combined as shown in FIG. 7. The number of concentric circles forming the marks 111 is more than one, and is not particularly limited to three.

The capsule medical device 10 and an appropriate amount of liquid 100 are introduced into the container 110. In this case, the capsule medical device 10 in the container 110 floats on the liquid surface of the liquid 100, with an image viewing field facing vertically downward, as shown in FIG. 8. The amount of the liquid 100 to be introduced into the container 110 is adjusted so that the level of the liquid 100 (the distance from the bottom surface of the container 110 to the liquid surface of the liquid 100) is fixed while the capsule medical device 10 is floating on the liquid surface.

The capsule medical device 10 floating in the liquid 100 captures the image 102 shown in FIG. 9, catching the bottom surface of the container 110 within the image viewing field. The image 102 captured by the capsule medical device 10 includes the marks 111 formed on the bottom surface of the container 110 as the subject. The marks 111 in the image 102 are more clearly shown, if the liquid 100 is transparent and colorless.

The receiving unit 3 receives the image signal of the image 102 captured by the capsule medical device 10 floating in the liquid 100 in the container 110. The information acquiring unit 4 acquires the image signal of the image 102 captured by the capsule medical device 10 from the receiving unit 3. Based on the acquired image 102, the information acquiring unit 4 calculates the density $\rho_{CP}$ as an example of the physical information about the magnetic guiding of the capsule medical device 10. In this case, the information acquiring unit 4 calculates the density $\rho_{CP}$, based on the captured state of the marks 111 in the image 102.

Here, the floating level of the capsule medical device 10 in the liquid 100 becomes higher and lower in accordance with the density $\rho_{CP}$ of the capsule medical device 10. Therefore, if the angle of view of the capsule medical device 10 is fixed, the range in which the marks 111 can be captured within the image viewing field of the capsule medical device 10 (hereinafter referred to as the capture allowing range of the marks 111) varies with the floating level of the capsule medical device 10 or the density $\rho_{CP}$ of the capsule medical device 10. More specifically, the capture allowing range of the marks 111 becomes narrower as the density $\rho_{CP}$ of the capsule medical device 10 becomes higher. The capture allowing range of the marks 111 becomes wider as the density $\rho_{CP}$ of the capsule medical device 10 becomes lower. The captured state of the marks 111 in the image 102 captured by the capsule medical device 10 varies as the capture allowing range of the marks 111 varies.

The information acquiring unit 4 calculates the density $\rho_{CP}$ of the capsule medical device 10, based on the captured state of the marks 111 in the image 102 captured by the capsule medical device 10, e.g., the number of concentric circles or the sizes of the concentric circles of the marks 111 included in the image 102. By performing this operation to calculate the density of the capsule medical device 10, the information acquiring unit 4 can acquire the density $\rho_{CP}$ as the physical information about the magnetic guiding of the capsule medical device 10, before the capsule medical device 10 is introduced into an internal organ of the test subject.

In a case where the capsule medical device 10 sinks below the liquid surface of the liquid 100, the information acquiring unit 4 calculates the density $\rho_{CP}$ of the capsule medical device 10, based on the physical information that is input by the input unit 5. More specifically, the input unit 5 inputs the weight W1 of the capsule medical device 10 in air, the weight W2 of the capsule medical device 10 in the liquid 100, and the density $\rho_{LIQ}$ of the liquid 100, into the control unit 8. The control unit 8 transmits each piece of the physical information that is input from the input unit 5 to the information acquiring unit 4, and controls the information acquiring unit 4 to calculate the density $\rho_{CP}$ of the capsule medical device 10. Acquiring the physical information from the control unit 8, the information acquiring unit 4 calculates the density $\rho_{CP}$ of the capsule medical device 10, under the control of the control unit 8. Based on the weights W1 and W2 of the capsule medical device 10 and the density $\rho_{LIQ}$ of the liquid 100, the information acquiring unit 4 calculates the density $\rho_{CP}$ of the capsule medical device 10, according to the following equation (4):

$$\rho_{CP} = \rho_{LIQ} \times W1/(W1-W2) \quad (4)$$

By performing the operation to calculate the density of the capsule medical device 10 according to the equation (4), the information acquiring unit 4 can acquire the density $\rho_{CP}$ as the physical information about the magnetic guiding of the capsule medical device 10, before the capsule medical device 10 is introduced into an internal organ of the test subject.

Figure 10:
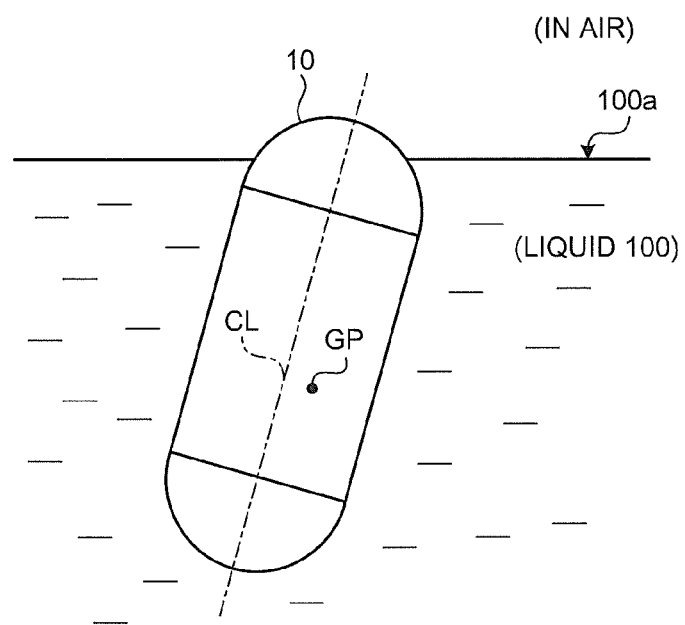
FIG. 10 is a schematic view showing an example of the capsule medical device that is floating in the liquid while tilting.

The following is a detailed description of the acquirement of the gravity center position GP of the capsule medical device 10 observed in a case where the capsule medical device 10 can float on the liquid surface, with an image viewing field facing upward. FIG. 10 is a schematic view showing an example case where the capsule medical device is floating in the liquid, while tilting. FIG. 11 is a schematic view showing an example of an image that is captured by the capsule medical device floating in the liquid while tilting.

In a case where the gravity center position GP of the capsule medical device 10 that can float in the liquid 100 deviates in the radial direction from the long axis CL, the capsule medical device 10 in such a gravity state tilts while floating on the liquid surface 100a of the liquid 100, as shown in FIG. 10. The tilting state of the capsule medical device 10 here refers to a state in which the long axis CL of the capsule medical device 10 is tilted relative to the vertical direction.

The capsule medical device 10 that is floating while tilting in the liquid 100 captures the image 101 shown in FIG. 11, with the image viewing field facing upward. The image 101 captured by the capsule medical device 10 in such a tilting state includes the boundary portion B between the liquid surface 100a of the liquid 100 and the exterior of the capsule medical device 10. In this case, the center C2 of the boundary portion B in the image 101 is shifted from the center C1 of the image 101, as shown in FIG. 11. The shift amount from the center C1 of the image 101 to the center C2 of the boundary portion B varies as the amount of tilt of the capsule medical device 10 relative to the vertically upward direction varies. Also, the relative shift direction of the center C2 of the boundary portion B with respect to the center C1 of the image 101 varies as the direction of tilt of the capsule medical device 10 relative to the vertically upward direction varies.

In this situation, the receiving unit 3 receives the image signal of the image 101 captured by the capsule medical device 10 in such a tilting state. The information acquiring unit 4 acquires the image signal of the image 101 captured by the capsule medical device 10 in the tilting state from the receiving unit 3. Based on the acquired image 101, the information acquiring unit 4 acquires the gravity center position GP as an example of the physical information about the magnetic guiding of the capsule medical device 10. In this case, the information acquiring unit 4 calculates a shift vector E that extends between the center C1 of the image 101 and the center C2 of the boundary portion B (see FIG. 11). The shift vector E is the vector that indicates the shift amount and shift direction of the center C2 of the boundary portion B relative to the center C1 of the image 101. The information acquiring unit 4 transmits the vector components information about the vector E to the control unit 8, with the vector components information indicating the relative shift amount and relative shift direction of the gravity center position GP of the capsule medical device 10 with respect to its long axis direction CL.

By performing the above operation to calculate the gravity center position of the capsule medical device 10, the information acquiring unit 4 can acquire the gravity center position GP as the physical information about the magnetic guiding of the capsule medical device 10, in both situations where the capsule medical device 10 has already been introduced into an internal organ of a test subject and where the capsule medical device 10 has not been introduced thereinto.

More specifically, in a case where the gravity center position GP of the capsule medical device 10 is acquired before the capsule medical device 10 is introduced into an internal organ of a test subject, the capsule medical device 10 and an appropriate amount of liquid 100 are introduced to a predetermined container, so that the capsule medical device 10 floats on the liquid surface 100a of the liquid 100 in the container. In this situation, the receiving unit 3 receives the image 101 captured by the capsule medical device 10 that is floating in the liquid 100 in the container. Based on the image 101 received by the receiving unit 3, the information acquiring unit 4 calculates the shift vector E of the boundary portion B in the above described manner. After that, the liquid 100 and the capsule medical device 10 are introduced into an internal organ of the test subject.

In this operation to calculate the gravity center position of the capsule medical device 10, the container is a hollow container that has an internal diameter that is greater than the external diameter of the capsule medical device 10, and has a depth that is greater than the length of the capsule medical device 10 in its long axis direction, as in the above described operation to calculate the density of the capsule medical device 10.

In a case where the gravity center position GP of the capsule medical device 10 is acquired after the capsule medical device 10 is introduced into an internal organ of the test subject, the capsule medical device 10 and an appropriate amount of liquid 100 are introduced into an internal organ of the test subject via the oral route, so that the capsule medical device 10 floats on the liquid surface 100a of the liquid 100 in the internal organ of the test subject. In this situation, the receiving unit 3 receives the image 101 captured by the capsule medical device 10 floating in the liquid 100 in the internal organ. Based on the image 101 received by the receiving unit 3, the information acquiring unit 4 calculates the shift vector E of the boundary portion B in the above described manner.

In a case where the capsule medical device 10 in a tilting state has an image viewing field facing downward, the receiving unit 3 receives the image 102 captured by the capsule medical device 10 floating in the liquid 100 in the above described container 110. In this case, the information acquiring unit 4 calculates the shift vector of the marks 111 in the image 102 (the vector indicating the shift amount and shift direction of the center of the marks 111 relative to the center of the image 102), instead of the shift vector E of the boundary portion B. The information acquiring unit 4 then transmits the vector components information about the calculated shift vector to the control unit 8, with the vector components information indicating the relative shift amount and the relative shift direction of the gravity center position GP of the capsule medical device 10 with respect to its long axis direction CL.

By combining the density calculating operation and the gravity center calculating operation, the information acquiring unit 4 can also calculate both the density $\rho_{CP}$ and the gravity center position GP (more specifically, the vector components information about the shift vector) of the capsule medical device 10, based on the image 101 and the image 102 captured by the capsule medical device 10. The information acquiring unit 4 can transmit both the density $\rho_{CP}$ and the gravity center position GP of the capsule medical device 10 as the physical information about the magnetic guiding of the capsule medical device 10, to the control unit 8.

The following is a detailed description of the magnetic guiding of the capsule medical device 10 in accordance with the magnetic field condition set by the above described magnetic field condition setting unit 8a. FIG. 12 is a schematic view showing an example case where the capsule medical device introduced into the body of a test subject is magnetically guided. As shown in FIG. 12, the capsule medical device 10 introduced into an internal organ of the test subject 120 is floating in the liquid 100 also introduced into the internal organ. In this case, the capsule medical device 10 has the image viewing field of the image capturing unit 14 facing upward in the vertical direction, and the image viewing field of the image capturing unit 15 facing downward in the vertical direction. The image capturing units 14 and 15 sequentially capture in-vivo images of the test subject 120.

Based on the density $\rho_{CP}$ and the gravity center position GP of the capsule medical device 10 acquired by the information acquiring unit 4 in the above described manner, the magnetic field condition setting unit 8a sets the magnetic field conditions for the guiding magnetic field to be applied to the capsule medical device 10. The control unit 8 controls the magnetic field generating unit 2a and the power supply unit 2b to apply the guiding magnetic field satisfying the set magnetic field condition (field intensity, a field direction, a field gradient, or the like) to the capsule medical device 10 in the body of the test subject 120. Under the control of the control unit 8, the magnetic field generating unit 2a applies the guiding magnetic field satisfying the magnetic field condition to the capsule medical device 10 inside the body of the test subject 120.

More specifically, the magnetic field generating unit 2a applies a canceling magnetic field H to the magnet 19 of the capsule medical device 10 inside the body of the test subject 120, as shown in FIG. 12. Here, the canceling magnetic field H is an example of the guiding magnetic field satisfying the magnetic field condition that is set by the magnetic field condition setting unit 8a. The canceling magnetic field H is a magnetic field having magnetic force PW (magnetic attraction or magnetic repulsion) that acts in such a direction as to cancel the difference between the gravity force and the buoyant force acting on the capsule medical device 10 in the liquid 100, as shown in FIG. 12. In FIG. 12, the canceling magnetic field H forms a magnetic gradient in such a vertical direction as to compensate for the shortage of the buoyant acting on the capsule medical device 10. Based on the density $\rho_{CP}$ of the capsule medical device 10, the magnetic field condition setting unit 8a sets the size of the magnetic gradient of the canceling magnetic field H.

In a case where instruction information to magnetically guide the capsule medical device 10 has not been input from the input unit 5, the magnetic field generating unit 2a applies the canceling magnetic field H to the capsule medical device 10 inside the body of the test subject 120, so that the difference between the gravity force and the buoyant force acting on the capsule medical device 10 is canceled. As a result, the capsule medical device 10 inside the body of the test subject 120 becomes free from the gravity force and the buoyant force in the liquid 100. In a case where the instruction information to magnetically guide the capsule medical device 10 has been input from the input unit 5, the magnetic field generating unit 2a applies the canceling magnetic field H to the capsule medical device 10 inside the body of the test subject 120, and further applies a guiding magnetic field according to the instruction information to the capsule medical device 10. As a result, the magnetic field generating unit 2a can magnetically guide the capsule medical device 10 inside the body of the test subject 120, continuously from the state in which the capsule medical device 10 is free from the gravity force and the buoyant force. In this manner, the capsule medical device 10 being magnetically guided can move slowly in the liquid 100, following the guiding magnetic field. As a result, users can more easily handle the capsule medical device 10 being magnetically guided by operating the input unit 5.

As described so far, in the magnetically guiding system and the magnetically guiding method in accordance with the first embodiment of the present invention, the physical information about the magnetic guiding of the capsule medical device is acquired, based on the image captured by the capsule medical device in a liquid. The magnetic field condition suitable for the acquired physical information is set, and the guiding magnetic field satisfying the set magnetic field condition is applied to the capsule medical device in the liquid. In this manner, the capsule medical device is magnetically guided. Accordingly, the optimum magnetic field condition can be set in accordance with the physical information such as the density or gravity center position of the capsule medical device, and the guiding magnetic field satisfying the optimum magnetic field condition is output so as to control the magnetic guiding of the capsule medical device. Thus, the optimum magnetic field is applied to the capsule medical device, and the capsule medical device inside the body of a test subject can be magnetically guided with high precision.

Next, a second embodiment of the present invention will be described. In the first embodiment, the physical information (the density $\rho_{CP}$, the gravity center position GP, or the like) about the magnetic guiding of the capsule medical device 10 is acquired based on images captured by the capsule medical device 10 in a liquid. In the second embodiment, on the other hand, the density $\rho_{CP}$ of the capsule medical device 10 is acquired based on the temperature of the liquid 100 measured when the capsule medical device 10 starts floating up or sinking down in the liquid 100.

Figure 13:
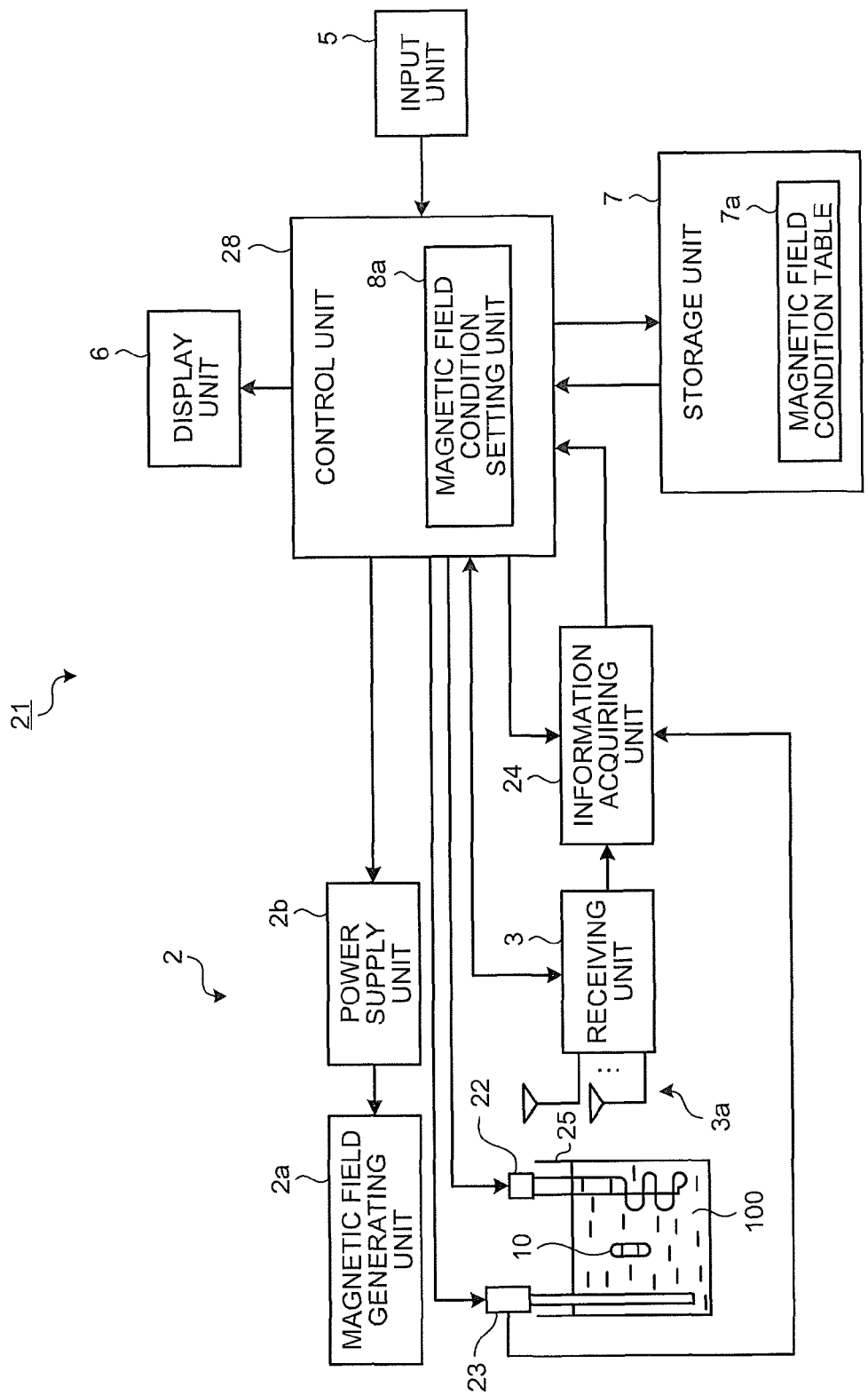
FIG. 13 is a block diagram schematically showing an example structure of a magnetically guiding system in accordance with a second embodiment of the present invention.

FIG. 13 is a block diagram schematically showing an example structure of a magnetically guiding system in accordance with the second embodiment of the present invention. As shown in FIG. 13, the magnetically guiding system 21 in accordance with the second embodiment differs from the magnetically guiding system 1 of the first embodiment in that the information acquiring unit 4 is replaced with an information acquiring unit 24, and the control unit 8 is replaced with a control unit 28. The magnetically guiding system 21 further includes a container 25 into which the capsule medical device 10 and the liquid 100 are to be introduced, a liquid temperature adjusting unit 22 that adjusts the temperature of the liquid 100 in the container 25, and a temperature measuring unit 23 that measures the temperature of the liquid 100 adjusted by the liquid temperature adjusting unit 22. The other configurations of this embodiment are the same as those of the first embodiment, and the same components as those of the first embodiment are denoted by the same reference numerals used in the first embodiment.

The container 25 is designed so that the capsule medical device 10 can float up or sink down in the liquid 100. More specifically, the container 25 has an internal diameter that is greater than the external diameter of the capsule medical device 10, and has a depth that is greater than the length of the capsule medical device 10 in its long axis direction. The capsule medical device 10 and an appropriate amount of liquid 100 are introduced into the container 25.

The liquid temperature adjusting unit 22 may be embodied with the use of at least one of a heating device and a cooling device, and is placed in the container 25. Under the control of the control unit 28, the liquid temperature adjusting unit 22 heats up or cools down the liquid 100 in the container 25, to adjust the temperature of the liquid 100.

The liquid temperature measuring unit 23 may be embodied with the use of a temperature sensor or the like, and is placed in the container 25. Under the control of the control unit 28, the liquid temperature measuring unit 23 measures the temperature of the liquid 100 in the container 25, and transmits the measured value of the temperature of the liquid 100 to the information acquiring unit 24.

Based on the temperature of the liquid 100 measured when the capsule medical device 10 starts floating up or sinking down in the liquid 100, the information acquiring unit 24 measures the density $\rho_{CP}$ as the physical information about the magnetic guiding of the capsule medical device 10. More specifically, under the control of the control unit 28, the information acquiring unit 24 sequentially acquires each image captured by the capsule medical device 10 in the liquid 100 from the receiving unit 3, and also sequentially acquires the measured values of the temperature of the liquid 100 from the liquid temperature measuring unit 23. Based on each image captured by the capsule medical device 10, the information acquiring unit 24 determines the timing when the capsule medical device 10 starts floating up or sinking down in the liquid 100. Based on the temperature of the liquid 100 measured by the liquid temperature measuring unit 23 when the capsule medical device 10 starts floating up or sinking down, the information acquiring unit 24 measures the density $\rho_{CP}$ of the capsule medical device 10. At the timing when the capsule medical device 10 in the liquid 100 starts floating up or sinking down in accordance with the temperature change of the liquid 100, the density $\rho_{CP}$ of the capsule medical device 10 is substantially the same as the density $\rho_{LIQ}$ of the liquid 100. Based on this fact, the information acquiring unit 24 converts the temperature of the liquid 100 measured at such timing into the density $\rho_{CP}$ of the capsule medical device 10, which is substantially the same as the density $\rho_{LIQ}$ of the liquid 100. In this manner, the information acquiring unit 24 acquires the density $\rho_{CP}$. Except for the function to measure the density of the capsule medical device 10, the information acquiring unit 24 has the same functions as those of the information acquiring unit 4 of the magnetically guiding system 1 in accordance with the first embodiment.

Based on instruction information that is input by the input unit 5, the control unit 28 controls each of the operations of the liquid temperature adjusting unit 22, the liquid temperature measuring unit 23, and the information acquiring unit 24. The control unit 28 also controls signal inputs and outputs between the liquid temperature measuring unit 23 and the information acquiring unit 24. In this case, the control unit 28 controls the liquid temperature adjusting unit 22 to adjust the temperature of the liquid 100 in the container 25 through a heating process or a cooling process. The control unit 28 also controls the liquid temperature measuring unit 23 to measure the temperature of the liquid 100 adjusted by the liquid temperature adjusting unit 22, and sequentially transmit the measured values of the temperature of the liquid 100 to the information acquiring unit 24. The control unit 28 further controls the information acquiring unit 24 to measure the density $\rho_{CP}$ of the capsule medical device 10, using each image captured by the capsule medical device 10 and the temperature of the liquid 100 measured by the liquid temperature measuring unit 23. The control unit 28 obtains the physical information such as the density $\rho_{CP}$ about the magnetic guiding of the capsule medical device 10, from the information acquiring unit 24. Except for the functions to control the liquid temperature adjusting unit 22, the liquid temperature measuring unit 23, and the information acquiring unit 24, the control unit 28 has the same functions as those of the control unit 8 of the magnetically guising system 1 in accordance with the first embodiment.

Next, the operation by the magnetically guiding system 21 in accordance with the second embodiment of the present invention will be described. The magnetically guiding system 21 in accordance with the second embodiment operates in the same manner as the magnetically guiding system 1 of the first embodiment, except for an operation when the density $\rho_{CP}$ as one kind of physical information about the magnetic guiding of the capsule medical device 10 is obtained. In other words, the control unit 28 of the magnetically guiding system 21 carries out the same procedures as those of steps S101 through S108 shown in FIG. 4. In this case, the control unit 28 acquires the density $\rho_{CP}$ of the capsule medical device 10 by a different technique from that utilized in step S102 by the control unit 8 of the first embodiment.

More specifically, in the above step S102, the control unit 28 controls the receiving unit 3 to receive images captured by the capsule medical device 10 in the liquid 100. The control unit 28 also controls the liquid temperature adjusting unit 22 to change the temperature of the liquid 100 having the capsule medical device 10 introduced thereinto. If the capsule medical device 10 is stabilized while floating in the liquid 100 at this point, the control unit 28 controls the liquid temperature adjusting unit 22 to gradually increase the temperature of the liquid 100 through a heating process. If the capsule medical device 10 is stabilized in a sunken state in the liquid 100 at this point, the control unit 28 controls the liquid temperature adjusting unit 22 to gradually lower the temperature of the liquid 100 through a cooling process. The control unit 28 also controls the liquid temperature measuring unit 23 to sequentially measure the temperature of the liquid 100 adjusted by the liquid temperature adjusting unit 22, and sequentially transmit the measured values of the temperature of the liquid 100 to the information acquiring unit 24.

The control unit 28 controls the information acquiring unit 24 to acquire physical information about the magnetic guiding of the capsule medical device 10, using each image captured by the capsule medical device 10 and received by the receiving unit 3, and the measured values of the temperature of the liquid 100 measured by the liquid temperature measuring unit 23. Under the control of the control unit 28, the information acquiring unit 24 acquires the physical information such as the density $\rho_{CP}$ about the magnetic guiding of the capsule medical device 10, and transmits the physical information to the control unit 28.

More specifically, the information acquiring unit 24 sequentially acquires each image captured by the capsule medical device 10 from the receiving unit 3, and calculates the motion vector between each two images. Based on the acquired motion vector between the images, the information acquiring unit 24 determines the timing when the capsule medical device 10 in the liquid 100 starts floating up or sinking down. The information acquiring unit 24 holds a data table indicating the density conversion data about the liquid 100 at each temperature. The information acquiring unit 24 measures the density $\rho_{CP}$ of the capsule medical device 10, based on the data table and the temperature of the liquid 100 measured by the liquid temperature measuring unit 23 at the timing when the capsule medical device 10 starts floating up or sinking down.

If the capsule medical device 10 is stabilized while floating in the liquid 100 at this point, the capsule medical device 10 in the floating state starts sinking down as the density $\rho_{LIQ}$ of the liquid 100 becomes lower due to an increase in the temperature of the liquid 100. When the capsule medical device 10 starts sinking down, the density $\rho_{CP}$ of the capsule medical device 10 becomes substantially equal to the density $\rho_{LIQ}$ of the liquid 100. If the capsule medical device 10 is stabilized in a sunken state in the liquid 100, the capsule medical device 10 in the sunken state starts floating up as the density $\rho_{LIQ}$ of the liquid 100 becomes higher due to a decrease in the temperature of the liquid 100. When the capsule medical device 10 starts sinking down, the density $\rho_{CP}$ of the capsule medical device 10 becomes substantially equal to the density $\rho_{LIQ}$ of the liquid 100.

Based on the relationship between the density $\rho_{LIQ}$ of the liquid 100 and the density $\rho_{CP}$ of the capsule medical device 100, and the data table in terms of the conversion of the density of the liquid 100, the information acquiring unit 24 converts the value of the temperature of the liquid 100 measured at the timing when the capsule medical device 10 starts floating up or sinking down, into the density $\rho_{CP}$ of the capsule medical device 10, which is substantially equal to the density $\rho_{LIQ}$ of the liquid 100. As a result, the information acquiring unit 24 acquires the density $\rho_{CP}$, which is one kind of physical information about the magnetic guiding of the capsule medical device 10. The information acquiring unit 24 acquires the other physical information about the magnetic guiding of the capsule medical device 10, such as the gravity center position GP of the capsule medical device 10, in the same manner as the first embodiment in which the information acquiring unit 4 acquires the physical information.

In a case where the density $\rho_{CP}$ of the capsule medical device 10 floating in the liquid 100 is measured in the second embodiment, a sheet-like member may be put on the liquid 100, so as to eliminate the surface tension acting on the capsule medical device 10 in the floating state.

Figure 14:
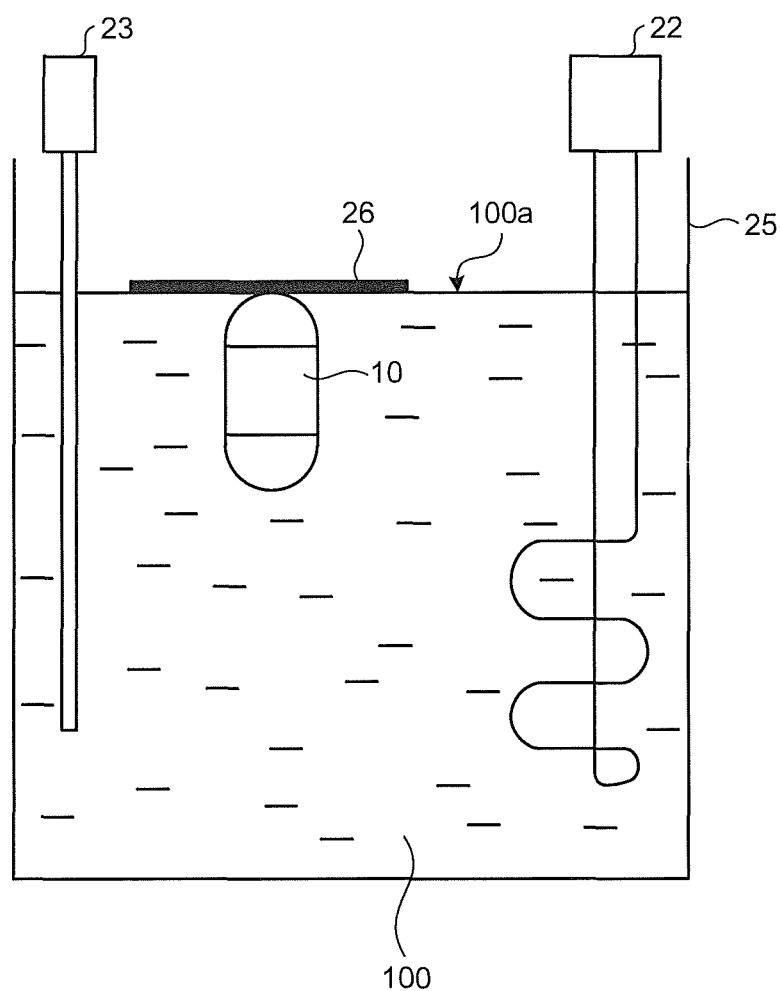
FIG. 14 is a schematic view showing an example case where a sheet-like member is put on the liquid surface in a container.

FIG. 14 is a schematic view showing an example case where a sheet-like member is placed on the liquid surface in the container. As shown in FIG. 14, the sheet-like member 26 is placed on the liquid surface 100a of the liquid 100 in the container 25. The sheet-like member 26 floats on the liquid surface 100a, and prevents the capsule medical device 10 protruding from the liquid surface 100a of the liquid 100. Accordingly, the sheet-like member 26 can eliminate the influence of surface tension acting on the capsule medical device 10. In other words, the capsule medical device 10 in the liquid 100 can start sinking down as the density $\rho_{LIQ}$ becomes lower due to an increase in the temperature of the liquid 100, without being affected by the surface tension at the liquid surface 100a. As a result, the liquid temperature measuring unit 23 can accurately measure the temperature of the liquid 100 when the density $\rho_{CP}$ of the capsule medical device 10 becomes substantially equal to the density $\rho_{LIQ}$ of the liquid 100. Using the accurately measured temperature of the liquid 100, the information acquiring unit 24 can measure the density $\rho_{CP}$ of the capsule medical device 10 with high precision.

As described above, in the magnetically guiding system and the magnetically guiding method in accordance with the second embodiment of the present invention, the temperature of the liquid into which the capsule medical device is introduced is adjusted so as to change the density of the liquid. By doing so, the capsule medical device in the liquid is caused to float up or sink down. When the capsule medical device starts floating up or sinking down in the liquid, the temperature of the liquid is measured. Based on the temperature of the liquid, the density of the capsule medical device is measured. The other configurations of this embodiment are the same as those of the first embodiment. Accordingly, not only the same effects as those of the first embodiment can be achieved, but also the capsule medical device can be magnetically guided with higher precision, as the density of the capsule medical device can be measured with high precision, and the magnetic field condition is set based on the highly precise density of the capsule medical device.

Next, a third embodiment of the present invention will be described. In the first embodiment, the physical information (the density $\rho_{CP}$, the gravity center position GP, or the like) about the magnetic guiding of the capsule medical device 10 is acquired based on images captured by the capsule medical device 10 in a liquid. In the third embodiment, on the other hand, a gradient magnetic field is applied to the capsule medical device 10 in the liquid 100, and the density $\rho_{CP}$ of the capsule medical device 10 is acquired based on the magnetic force of the gradient magnetic field that is being applied when the capsule medical device 10 starts floating up or sinking down in the liquid 100.

Figure 15:
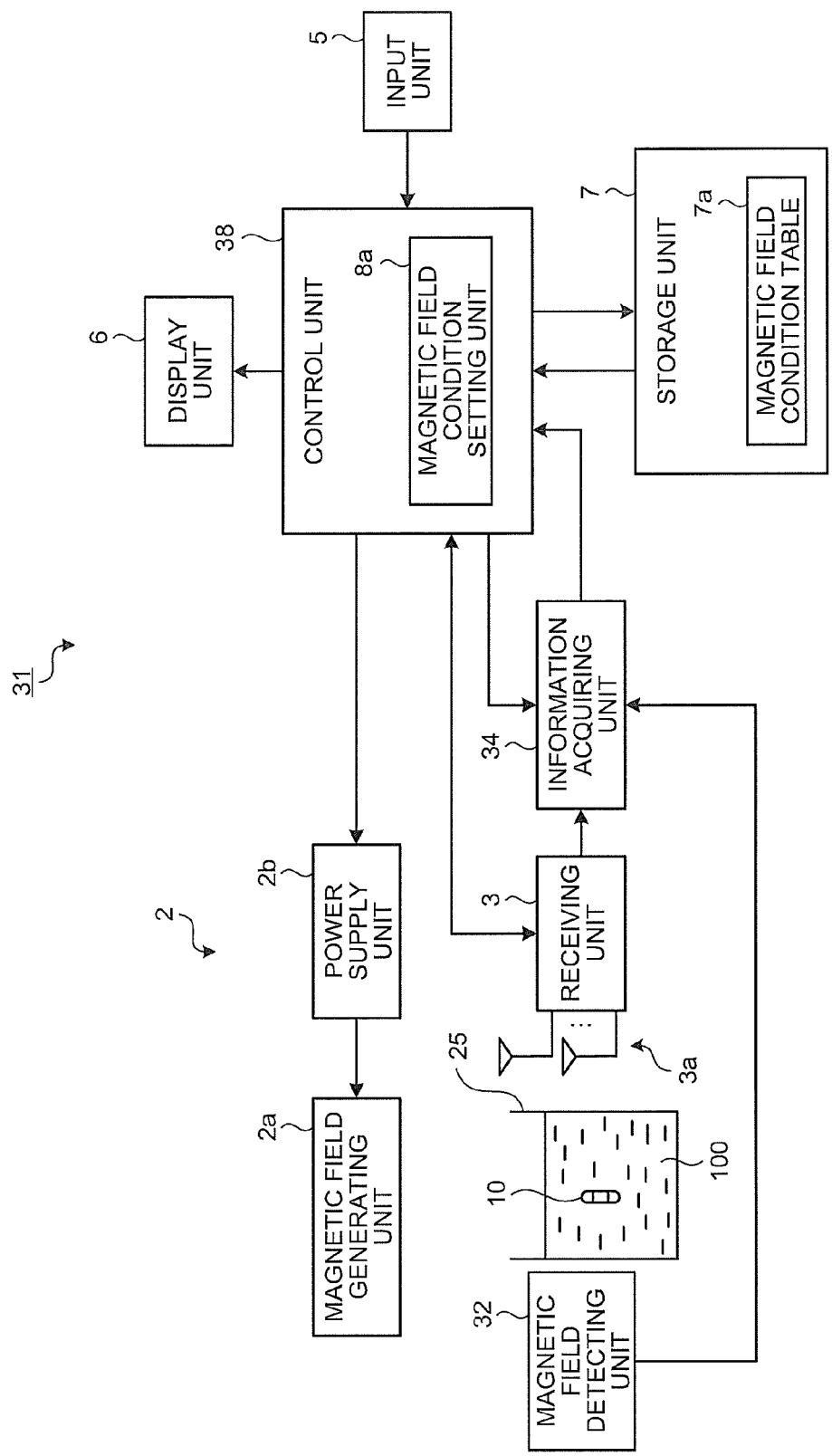
FIG. 15 is a block diagram schematically showing an example structure of a magnetically guiding system in accordance with a third embodiment of the present invention.

FIG. 15 is a block diagram schematically showing an example structure of a magnetically guiding system in accordance with the third embodiment of the present invention. As shown in FIG. 15, the magnetically guiding system 31 in accordance with the third embodiment differs from the magnetically guiding system 1 of the first embodiment in that the information acquiring unit 4 is replaced with an information acquiring unit 34, and the control unit 8 is replaced with a control unit 38. The magnetically guiding system 31 further includes a magnetic field detecting unit 32 that detects the gradient magnetic field applied to the capsule medical device 10 in the liquid 100. In the third embodiment, the capsule medical device 10 and the liquid 100 are put into the container 25 as in the above described second embodiment. The other configurations of this embodiment are the same as those of the first embodiment, and the same components as those of the first embodiment are denoted by the same reference numerals used in the first embodiment.

The magnetic field detecting unit 32 may be embodied with the use of detector coils, and detects the magnetic gradient of the gradient magnetic field applied to the capsule medical device 10 in the liquid 100. The magnetic field detecting unit 32 transmits the detected magnetic gradient of the gradient magnetic field to the information acquiring unit 34. The gradient magnetic field to be detected by the magnetic field detecting unit 32 is applied to the capsule medical device 10 in the liquid 100 by the magnetic field generating unit 2a. Under the control of the control unit 38, the magnetic field generating unit 2a applies the gradient magnetic field to the capsule medical device 10 in the liquid 100, while gradually changing the magnetic gradient.

Based on the magnetic gradient of the gradient magnetic field detected at the timing when the capsule medical device 10 in the liquid 100 starts floating up or sinking down in accordance with the gradient magnetic field generated from the magnetic field generating unit 2a, the information acquiring unit 34 acquires the density $\rho_{CP}$ as one kind of the physical information about the magnetic guiding of the capsule medical device 10. More specifically, under the control of the control unit 38, the information acquiring unit 34 sequentially acquires each image captured by the capsule medical device 10 in the liquid 100 from the receiving unit 3, and also sequentially acquires magnetic gradients of the gradient magnetic field applied to the capsule medical device 10. Based on each of the images captured by the capsule medical device 10, the information acquiring unit 34 determines the timing when the capsule medical device 10 starts floating up or sinking down in the liquid 100. The information acquiring unit 34 acquires the magnetic gradient of the gradient magnetic field detected by the magnetic field detecting unit 32 at the timing when the capsule medical device 10 starts floating up or sinking down. The information acquiring unit 34 then converts the acquired magnetic gradient into the magnetic force of the gradient magnetic field detected at this timing. Using the mass W1 of the capsule medical device 10 that is input beforehand by the input unit 5, the density $\rho_{LIQ}$ of the liquid 100, and the magnetic force of the gradient magnetic field, the information acquiring unit 34 calculates the density $\rho_{CP}$ of the capsule medical device 10. Except for the function to measure the density of the capsule medical device 10, the information acquiring unit 34 has the same functions as those of the information acquiring unit 4 of the magnetically guiding system 1 in accordance with the first embodiment.

The control unit 38 controls the information acquiring unit 34, instead of the information acquiring unit 4. In this case, the control unit 38 controls the information acquiring unit 34 to calculate the density $\rho_{CP}$ of the capsule medical device 10, using each of the images captured by the capsule medical device 10 and the result of the magnetic gradient detection performed on the gradient magnetic field by the magnetic field detecting unit 32. The control unit 38 acquires the physical information about the magnetic guiding of the capsule medical device 10, such as the density $\rho_{CP}$, from the information acquiring unit 34. Based on instruction information that is input by the input unit 5, the control unit 38 also controls the gradient magnetic field generating operation of the magnetic field generating unit 2a by controlling the power supply unit 2b. In this case, the control unit 38 controls the magnetic field generating unit 2a to apply the gradient magnetic field to the capsule medical device 10 in the liquid 100, while gradually changing the magnetic gradient. Except for the functions to control the magnetic field generating unit 2a and the information acquiring unit 34, the control unit 38 has the same functions as those of the control unit 8 of the magnetically guising system 1 in accordance with the first embodiment.

Next, the operation by the magnetically guiding system 31 in accordance with the third embodiment of the present invention will be described. The magnetically guiding system 31 in accordance with the third embodiment operates in the same manner as the magnetically guiding system 1 of the first embodiment, except for an operation when the density $\rho_{CP}$ as one kind of physical information about the magnetic guiding of the capsule medical device 10 is obtained. In other words, the control unit 38 of the magnetically guiding system 31 carries out the same procedures as those of steps S101 through S108 shown in FIG. 4. In this case, the control unit 38 acquires the density $\rho_{CP}$ of the capsule medical device 10 by a different technique from that utilized in step S102 by the control unit 8 of the first embodiment.

More specifically, in the above step S102, the control unit 38 controls the receiving unit 3 to receive images captured by the capsule medical device 10 in the liquid 100. The control unit 38 also controls the magnetic field generating unit 2a to apply a gradient magnetic field to the capsule medical device 10 in the liquid 100, while changing the magnetic gradient. If the capsule medical device 10 is stabilized while floating in the liquid 100 at this point, the control unit 38 controls the change of the magnetic gradient of the gradient magnetic field generated from the magnetic field generating unit 2a, so that the capsule medical device 10 in the floating state gradually sinks down in the liquid 100. If the capsule medical device 10 is stabilized in a sunken state in the liquid 100 at this point, the control unit 38 controls the change of the magnetic gradient of the gradient magnetic field generated from the magnetic field generating unit 2a, so that the capsule medical device 10 in the sunken state gradually floats up in the liquid 100.

The control unit 38 also controls the information acquiring unit 34 to acquire physical information about the magnetic guiding of the capsule medical device 10, appropriately using each image captured by the capsule medical device 10 and received by the receiving unit 3, and the result of the magnetic gradient detection performed on the gradient magnetic field by the magnetic field detecting unit 32. Under the control of the control unit 38, the information acquiring unit 34 acquires the physical information such as the density $\rho_{CP}$ about the magnetic guiding of the capsule medical device 10, and transmits the acquired physical information to the control unit 38.

More specifically, the information acquiring unit 34 sequentially acquires each image captured by the capsule medical device 10 from the receiving unit 3, and calculates the motion vector between each image. Based on the motion vector between the images, the information acquiring unit 34 determines the timing when the capsule medical device 10 in the liquid 100 starts floating up or sinking down.

The information acquiring unit 34 also acquires the magnetic gradient of the gradient magnetic field detected by the magnetic field detecting unit 32 at the timing when the capsule medical device 10 starts floating up or sinking down. The information acquiring unit 34 then converts the magnetic gradient into the magnetic force (magnetic attraction or magnetic repulsion) of the gradient magnetic field. Based on the magnetic force of the gradient magnetic field obtained through the conversion process and the mass W1 of the capsule medical device 10 in air, the information acquiring unit 34 calculates the buoyant force f acting on the capsule medical device 10 in the liquid 100. The information acquiring unit 34 then divides the calculated buoyant force f by the density $\rho_{LIQ}$ of the liquid 100, to calculate the volume $V_{CP}$ of the capsule medical device 10. The information acquiring unit 34 further divides the mass W1 of the capsule medical device 10 by the volume $V_{CP}$, to calculate the density $\rho_{CP}$ of the capsule medical device 10. As a result, the information acquiring unit 34 acquires the density $\rho_{CP}$ as one kind of physical information about the magnetic guiding of the capsule medical device 10.

The information acquiring unit 34 acquires the other physical information about the magnetic guiding of the capsule medical device 10, such as the gravity center position GP of the capsule medical device, in the same manner as the manner in which the information acquiring unit 4 of the first embodiment acquires the physical information. The mass W1 of the capsule medical device 10 and the density $\rho_{LIQ}$ of the liquid 100 that are used in the above operation by the information acquiring unit 34 to calculate the density of the capsule medical device 10 are input beforehand by the input unit 5.

In a case where the density $\rho_{CP}$ of the capsule medical device 10 floating in the liquid 100 is measured in the third embodiment, the sheet-like member 26 may be put on the liquid surface of the liquid 100 in the container 25, so as to eliminate the surface tension acting on the capsule medical device 10 in the floating state, as in the second embodiment. Accordingly, the capsule medical device 10 in the liquid 100 can start sinking down in accordance with the gradient magnetic field generated from the magnetic field generating unit 2a, without being affected by the surface tension at the liquid surface 100a. As a result, the magnetic field detecting unit 32 can detect the minimum magnetic gradient of the gradient magnetic field required for the capsule medical device 10 to start sinking in the liquid 100. Using the minimum magnetic gradient of the gradient magnetic field, the information acquiring unit 34 can measure the density $\rho_{CP}$ of the capsule medical device 10 with high precision. Also, since the liquid 100 in the container 25 is maintained at a fixed temperature, the information acquiring unit 34 can more accurately measure the density $\rho_{CP}$ of the capsule medical device 10 with higher precision.

In the third embodiment, the information acquiring unit 34 acquires the physical information such as the density $\rho_{CP}$ of the capsule medical device 10 in the container 25, before the capsule medical device 10 is introduced into an internal organ of a test subject. However, the information acquiring unit 34 may acquire the physical information such as the density $\rho_{CP}$ of the capsule medical device 10, after the capsule medical device 10 is introduced into the internal organ of the test subject. In such a case, the capsule medical device 10 and an appropriate amount of liquid 100 are introduced into an internal organ of the test subject via the oral route, so that the capsule medical device 10 is in a floating state or a sunken state in the liquid 100 inside the internal organ of the test subject. In this situation, the magnetic field generating unit 2a applies a gradient magnetic field to the capsule medical device 10 inside the body of the test subject, and the receiving unit 3 receives images captured by the capsule medical device 10 inside the body of the test subject. The magnetic field detecting unit 32 detects the magnetic gradient of the gradient magnetic field applied by the magnetic field generating unit 2a to the capsule medical device 10 inside the body of the test subject. In the same manner as in the case where the information acquiring unit 34 acquires the physical information before the capsule medical device 10 is introduced into the body of the test subject, the information acquiring unit 34 acquires the physical information such as the density $\rho_{CP}$ about the magnetic guiding of the capsule medical device 10, appropriately using each image captured by the capsule medical device 10 and received by the receiving unit 3, and the result of the magnetic gradient detection performed on the gradient magnetic field by the magnetic field detecting unit 32.

As described above, in the magnetically guiding system and the magnetically guiding method in accordance with the third embodiment of the present invention, a gradient magnetic field is applied to the capsule medical device in the liquid, and the magnetic gradient of the gradient magnetic field is detected when the capsule medical device in the liquid starts floating up or sinking down in accordance with the gradient magnetic field. Based on the detected magnetic gradient, the density of the capsule medical device is calculated. The other configurations of this embodiment are the same as those of the first embodiment. Accordingly, not only the same effects as those of the first embodiment can be achieved, but also the capsule medical device can be magnetically guided with higher precision, as the density of the capsule medical device can be calculated with high precision, and the magnetic field condition is set based on the highly precise density of the capsule medical device.

Next, a fourth embodiment of the present invention will be described. In the above described third embodiment, the density $\rho_{CP}$ of the capsule medical device 10 is calculated, based on the magnetic gradient of a gradient magnetic field detected by the magnetic field detecting unit 32 when the capsule medical device 10 in the liquid 100 starts floating up or sinking down. In the fourth embodiment, on the other hand, the magnetic gradient of a gradient magnetic field detected by the magnetic field detecting unit 32 at the timing when the capsule medical device 10 starts floating up or sinking down in the liquid 100 is acquired as one kind of physical information about the magnetic guiding of the capsule medical device 10.

Figure 16:
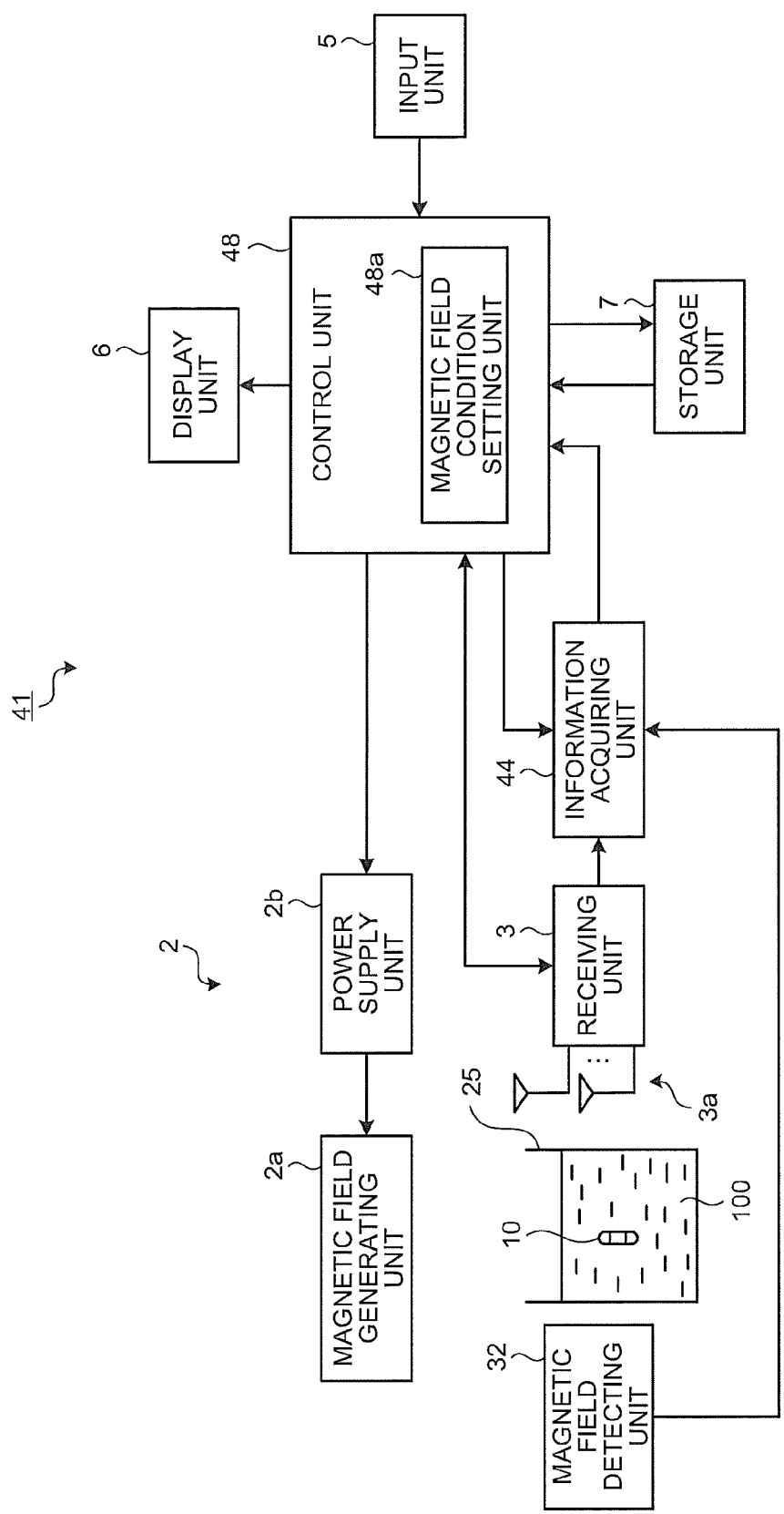
FIG. 16 is a block diagram schematically showing an example structure of a magnetically guiding system in accordance with a fourth embodiment of the present invention.

FIG. 16 is a block diagram schematically showing an example structure of a magnetically guiding system in accordance with the fourth embodiment of the present invention. As shown in FIG. 16, the magnetically guiding system 41 in accordance with the fourth embodiment differs from the magnetically guiding system 31 of the third embodiment in that the information acquiring unit 34 is replaced with an information acquiring unit 44, and the control unit 38 is replaced with a control unit 48. The control unit 48 includes a magnetic field condition setting unit 48a, instead of the magnetic field condition setting unit 8a. In the fourth embodiment, the storage unit 7 does not hold the magnetic field condition table 7a. The other configurations of this embodiment are the same as those of the third embodiment, and the same components as those of the third embodiment are denoted by the same reference numerals used in the third embodiment.

The information acquiring unit 44 acquires the magnetic gradient of the gradient magnetic field at the timing when the capsule medical device 10 in the liquid 100 starts flowing up or sinking down following the gradient magnetic field. The information acquiring unit 44 uses the magnetic gradient as the physical information about the magnetic guiding of the capsule medical device 10. More specifically, under the control of the control unit 48, the information acquiring unit 44 sequentially acquires each image captured by the capsule medical device 10 in the liquid 100 from the receiving unit 3, and sequentially acquires the magnetic gradients of the gradient magnetic field applied to the capsule medical device 10 from the magnetic detecting unit 32. Based on each of the images captured by the capsule medical device 10, the information acquiring unit 44 determines the timing when the capsule medical device 10 starts floating up or sinking down in the liquid 100. The information acquiring unit 44 acquires the magnetic gradient of the gradient magnetic field detected by the magnetic field detecting unit 32 when the capsule medical device 10 starts floating up or sinking down. The information acquiring unit 44 acquires the magnetic gradient as the physical information about the magnetic guiding of the capsule medical device 10. The information acquiring unit 44 transmits the acquired magnetic gradient of the gradient magnetic field to the control unit 48. As a result, the magnetic gradient of the gradient magnetic field as the physical information about the magnetic guiding of the capsule medical device 10 is fed back to the control unit 48.

The control unit 48 controls the information acquiring unit 44, instead of the information acquiring unit 34. In this case, the control unit 48 controls the information acquiring unit 44 to acquire the magnetic gradient of the gradient magnetic field detected by the magnetic field detecting unit 32 at the timing when the capsule medical device 10 starts floating up or sinking down, and use the magnetic gradient of the gradient magnetic field as the physical information about the magnetic guiding of the capsule medical device 10. In this manner, the control unit 48 acquires the magnetic gradient of the gradient magnetic field as the physical information about the magnetic guiding of the capsule medical device 10, from the information acquiring unit 44.

The control unit 48 includes a magnetic field condition setting unit 48a. The magnetic field condition setting unit 48a sets a magnetic field condition for the guiding magnetic field to be applied to the capsule medical device 10. Here, the magnetic gradient acquired as the physical information about the magnetic guiding of the capsule medical device 10 by the information acquiring unit 44 is set as the magnetic field condition. In other words, as the magnetic field condition for the guiding magnetic field, the magnetic field condition setting unit 48a sets the magnetic gradient of the gradient magnetic field fed back by the information acquiring unit 44. Except for the function to control the information acquiring unit 44 and the function to set the magnetic field condition, the control unit 48 has the same functions as those of the control unit 38 of the magnetically guising system 31 in accordance with the third embodiment.

Next, the operation by the magnetically guiding system 41 in accordance with the fourth embodiment of the present invention will be described. The magnetically guiding system 41 in accordance with the fourth embodiment operates in the same manner as the magnetically guiding system 31 of the third embodiment, except for an operation when the physical information about the magnetic guiding of the capsule medical device 10 is obtained, and when the magnetic field condition is set. In other words, the control unit 48 of the magnetically guiding system 41 carries out the same procedures as those of steps S101 through S108 shown in FIG. 4. In this case, the control unit 48 acquires the physical information about the magnetic guiding of the capsule medical device 10 by a different technique from that utilized in step S102 by the control unit 38 in the third embodiment. Also, the control unit 48 sets the magnetic field condition for magnetically guiding the capsule medical device 10 by a different technique from that utilized in step S103 by the control unit 38 in the third embodiment.

More specifically, in step S102, the control unit 48 controls the receiving operation of the receiving unit 3 and the gradient magnetic field generating operation of the magnetic field generating unit 2a, as in the third embodiment. The control unit 48 also controls the information acquiring unit 44 to acquire physical information about the magnetic guiding of the capsule medical device 10, using each image captured by the capsule medical device 10 and received by the receiving unit 3, and the result of the magnetic gradient detection performed on the gradient magnetic field by the magnetic field detecting unit 32. Under the control of the control unit 48, the information acquiring unit 44 acquires the physical information about the magnetic guiding of the capsule medical device 10, and transmits the acquired physical information to the control unit 48.

More specifically, the information acquiring unit 44 determines the timing when the capsule medical device 10 in the liquid 100 starts floating up or sinking down, based on the motion vector between the images captured by the capsule medical device 10, as in the third embodiment. The information acquiring unit 44 also acquires the magnetic gradient of the gradient magnetic field detected by the magnetic field detecting unit 32 when the capsule medical device 10 starts floating up or sinking down, among the magnetic gradients of the gradient magnetic field sequentially detected by the magnetic field detecting unit 32. The information acquiring unit 44 acquires the magnetic gradient as the physical information about the magnetic guiding of the capsule medical device 10. The information acquiring unit 44 then transmits the magnetic gradient of the gradient magnetic field in that timing as the physical information about the magnetic guiding of the capsule medical device 10, to the control unit 48.

In the above step S103, the control unit 48 acquires the magnetic gradient of the gradient magnetic field as the physical information about the magnetic guiding of the capsule medical device 10, from the information acquiring unit 44. The magnetic field condition setting unit 48a sets the magnetic gradient acquired from the information acquiring unit 44, as the magnetic field condition for the magnetically guiding magnetic field to be applied to the capsule medical device 10.

In a case where the magnetic gradient of the gradient magnetic field for causing the capsule medical device 10 in a floating state to start sinking down in the fourth embodiment, the sheet-like member 26 may be put on the liquid surface of the liquid 100 in the container 25, so as to eliminate the surface tension acting on the capsule medical device 10 in the floating state, as in the second embodiment. Accordingly, the capsule medical device 10 in the liquid 100 can start sinking down in accordance with the gradient magnetic field generated from the magnetic field generating unit 2a, without being affected by the surface tension at the liquid surface 100a. As a result, the magnetic field detecting unit 32 can accurately detect the magnetic gradient of the gradient magnetic field required for causing the capsule medical device 10 to start sinking in the liquid 100. Thus, the information acquiring unit 44 can acquire the accurate magnetic gradient as the physical information about the magnetic guiding of the capsule medical device 10.

In the fourth embodiment, the information acquiring unit 44 acquires the physical information about the magnetic guiding of the capsule medical device 10 in the container 25, before the capsule medical device 10 is introduced into an internal organ of a test subject. However, the information acquiring unit 44 may acquire the physical information about the magnetic guiding of the capsule medical device 10, after the capsule medical device 10 is introduced into the internal organ of the test subject. In such a case, the capsule medical device 10 and an appropriate amount of liquid 100 are introduced into the internal organ of the test subject via the oral route, so that the capsule medical device 10 is in a floating state or a sunken state in the liquid 100 inside the internal organ of the test subject. In this situation, the magnetic field generating unit 2a applies a gradient magnetic field to the capsule medical device 10 inside the body of the test subject, and the receiving unit 3 receives images captured by the capsule medical device 10 inside the body of the test subject. The magnetic field detecting unit 32 detects the magnetic gradient of the gradient magnetic field applied by the magnetic field generating unit 2a to the capsule medical device 10 inside the body of the test subject. In the same manner as in the case where the information acquiring unit 44 acquires the physical information before the capsule medical device 10 is introduced into the body of the test subject, the information acquiring unit 44 acquires the magnetic gradient of the gradient magnetic field detected by the magnetic field detecting unit 32 when the capsule medical device 10 starts floating up or sinking down inside the body of the test subject. The information acquiring unit 44 acquires the magnetic gradient as the physical information about the magnetic guiding of the capsule medical device 10.

As described above, in the magnetically guiding system and the magnetically guiding method in accordance with the fourth embodiment of the present invention, a gradient magnetic field is applied to the capsule medical device in the liquid, and the magnetic gradient of the gradient magnetic field is detected when the capsule medical device in the liquid starts floating up or sinking down in accordance with the applied gradient magnetic field. The detected magnetic gradient is obtained as the physical information about the magnetic guiding of the capsule medical device, and the obtained physical information (the magnetic gradient) is set as the magnetic field condition for magnetically guiding the capsule medical device. The other configurations of this embodiment are the same as those of the third embodiment. Accordingly, not only the same effects as those of the third embodiment can be achieved, but also the magnetic gradient of the gradient magnetic field generated for magnetically guiding the capsule medical device in the liquid can be fed back to the control system for the magnetic guiding. As a result, the magnetic guiding of the capsule medical device can be more practically controlled.

Next, a fifth embodiment of the present invention will be described. In the first embodiment, the physical information (the density $\rho_{CP}$, the gravity center position GP, or the like) about the magnetic guiding of the capsule medical device 10 is calculated based on images captured by the capsule medical device 10 in a liquid. In the fifth embodiment, on the other hand, the physical information about the magnetic guiding of the capsule medical device 10 is stored beforehand in the capsule medical device 10 after the manufacture, and the physical information that is radio-transmitted together with images from the capsule medical device 10 to the outside is to be obtained.

Figure 17:
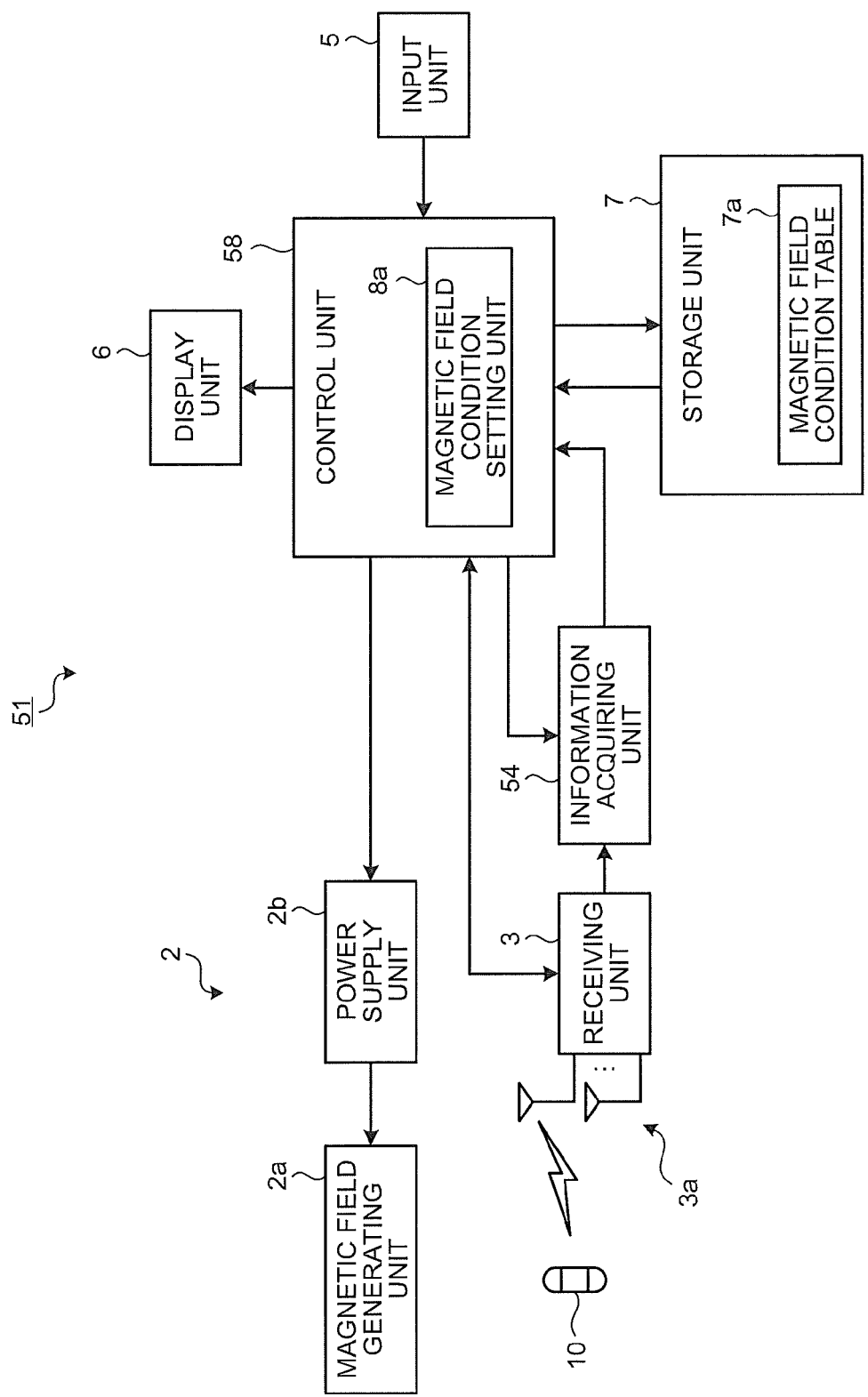
FIG. 17 is a block diagram schematically showing an example structure of a magnetically guiding system in accordance with a fifth embodiment of the present invention.

FIG. 17 is a block diagram schematically showing an example structure of a magnetically guiding system in accordance with the fifth embodiment of the present invention. As shown in FIG. 17, the magnetically guiding system 51 in accordance with the fifth embodiment differs from the magnetically guiding system 1 of the first embodiment in that the information acquiring unit 4 is replaced with an information acquiring unit 54, and the control unit 8 is replaced with a control unit 58. In the fifth embodiment, the physical information about the magnetic guiding of the capsule medical device 10, such as the density $\rho_{CP}$ and the gravity center position GP, is stored beforehand in an internal memory (not shown) of the capsule medical device 10. The capsule medical device 10 radio-transmits the physical information together with captured images to the outside. The other configurations of this embodiment are the same as those of the first embodiment, and the same components as those of the first embodiment are denoted by the same reference numerals used in the first embodiment.

The information acquiring unit 54 acquires the physical information about the magnetic guiding of the capsule medical device 10 via the receiving unit 3. More specifically, under the control of the control unit 58, the receiving unit 3 receives image signals that contain data about images captured by the capsule medical device 10 in the liquid 100 and the physical information about the magnetic guiding of the capsule medical device 10. The receiving unit 3 then transmits the image signals from the capsule medical device 10 to the information acquiring unit 54 and the control unit 58. Under the control of the control unit 58, the information acquiring unit 54 acquires the image signals from the capsule medical device 10 via the receiving unit 3. From the acquired image signals, the information acquiring unit 54 extracts the physical information about the magnetic guiding of the capsule medical device 10. In this manner, the information acquiring unit 54 acquires the physical information about the magnetic guiding of the capsule medical device 10, and transmits the acquired physical information to the control unit 58.

As shown in FIG. 3, the capsule medical device 10 includes the control unit 17. The control unit 17 may be embodied with the use of a CPU that executes processing programs, and a memory that stores various kinds of information. After the manufacture of the capsule medical device 10, the memory of the control unit 17 stores the physical information about the magnetic guiding of the capsule medical device 10. The control unit 17 controls the radio communication unit 16 to radio-transmit the image signals containing the data about images captured by the image capturing units 14 and 15, and the physical information stored in the memory (the physical information about the magnetic guiding of the capsule medical device 10) to the outside. The image signals radio-transmitted from the radio communication unit 16 are received by the receiving unit 3 as described above.

Based on instruction information that is input from the input unit 5, the control unit 58 controls the operation of the information acquiring unit 54. In this case, the control unit 58 controls the information acquiring unit 54 to extract the physical information about the magnetic guiding of the capsule medical device 10 from the image signals that are transmitted from the capsule medical device 10 and are received by the receiving unit 3. The control unit 58 obtains the physical information about the magnetic guiding of the capsule medical device 10, such as the density $\rho_{CP}$, from the information acquiring unit 54. Except for the function to control the information acquiring unit 54, the control unit 58 has the same functions as those of the control unit 8 of the magnetically guising system 1 in accordance with the first embodiment.

Next, the operation by the magnetically guiding system 51 in accordance with the fifth embodiment of the present invention will be described. The magnetically guiding system 51 in accordance with the fifth embodiment operates in the same manner as the magnetically guiding system 1 of the first embodiment, except for an operation when the physical information about the magnetic guiding of the capsule medical device 10 is obtained. In other words, the control unit 58 of the magnetically guiding system 51 carries out the substantially same procedures as those of steps S101 through S108 shown in FIG. 4. In this case, the control unit 58 acquires the physical information about the magnetic guiding of the capsule medical device 10 by a different technique from that utilized in step S102 by the control unit 8 of the first embodiment.

More specifically, in step S102, the control unit 58 controls the receiving unit 3 to receive image signals captured by the capsule medical device 10 in the liquid 100. The control unit 58 also controls the information acquiring unit 54 to acquire image signals from the capsule medical device 10 via the receiving unit 3. The control unit 58 further controls the information acquiring unit 54 to acquire the physical information about the magnetic guiding of the capsule medical device 10 contained in the image signals.

Under the control of the control unit 58, the information acquiring unit 54 acquires the image signals from the capsule medical device 10 via the receiving unit 3, and extracts the physical information about the magnetic guiding of the capsule medical device 10 from the acquired image signals. In this manner, the information acquiring unit 54 acquires the physical information about the magnetic guiding of the capsule medical device 10, and transmits the acquired physical information to the control unit 58.

The information acquiring unit 54 of the fifth embodiment can acquire the physical information about the magnetic guiding of the capsule medical device 10, in both situations where the capsule medical device 10 has already been introduced into an internal organ of a test subject and where the capsule medical device 10 has not been introduced thereinto. More specifically, the receiving unit 3 receives image signals from the capsule medical device 10 that has not been introduced to an internal organ of a test subject. The information acquiring unit 54 extracts the physical information about the magnetic guiding of the capsule medical device 10 from the image signals received by the receiving unit 3. Alternatively, the receiving unit 3 receives image signals from the capsule medical device 10 that has been introduced into an internal organ of a test subject, and the information acquiring unit 54 extracts the physical information about the magnetic guiding of the capsule medical device 10 from the image signals received by the receiving unit 3.

As described above, in the magnetically guiding system and the magnetically guiding method in accordance with the fifth embodiment of the present invention, the physical information about the magnetic guiding of the capsule medical device is stored beforehand in an internal memory of the capsule medical device, and the stored physical information is included in image signals captured by the capsule medical device and is then radio-transmitted. The image signals from the capsule medical device are received, and the physical information about the magnetic guiding of the capsule medical device is extracted from the received image signals. The other configurations of this embodiment are the same as those of the first embodiment. Accordingly, not only the same effects as those of the first embodiment can be achieved, but also the physical information about the magnetic guiding of the capsule medical device can be readily obtained, in both situations where the capsule medical device has been introduced into an internal organ of a test subject and where the capsule medical device has not been introduced thereinto.

In each of the second through fourth embodiments, the timing when the capsule medical device 10 starts floating up or sinking down in the liquid 100 is determined, based on the motion vector between images sequentially captured by the capsule medical device 10 in the liquid 100. However, the present invention is not limited to that arrangement, and the timing when the capsule medical device 10 starts floating up or sinking down may be determined based on the location information about the capsule medical device 10 in the liquid 100. In such a case, each of the magnetically guiding systems of the second through fourth embodiments further includes a position detecting unit that detects the position of the capsule medical device 10 in the liquid 100. Based on the location information about the capsule medical device 10 detected by the position detecting unit, the information acquiring unit determines the timing when the capsule medical device 10 in the liquid 100 starts floating up or sinking down. The position detecting unit may detect the position of the capsule medical device 10, based on the reception field intensity of the receiving antennas 3a detected when the receiving unit 3 receives an image signal from the capsule medical device 10. Alternatively, the position detecting unit may detect the position of the capsule medical device 1, based on the intensity of the magnetic field generated from the magnet 19 provided inside the capsule medical device 10, or may detect the position of the capsule medical device 10 by some other techniques.

In each of the second through fourth embodiments, the timing when the capsule medical device 10 starts floating up or sinking down in the liquid 100 is determined with the use of images captured by the capsule medical device 10. However, the present invention is not limited to that arrangement. For example, images of the capsule medical device 10 in the liquid 100 may be captured by a camera independent of the capsule medical device 10, and the timing when the capsule medical device 10 starts floating up or sinking down in the liquid 100 may be determined with the use of the images captured by the camera independent of the capsule medical device 10.

Also, in each of the first through fifth embodiments, the physical information about the magnetic guiding of the capsule medical device is obtained by the information acquiring unit. However, the present invention is not limited to that arrangement, and the physical information about the magnetic guiding of the capsule medical device may be input through the input unit.

In the first embodiment, the mark 111 formed with concentric circles is provided at the bottom of the container 110. However, the present invention is not limited to that arrangement, and the mark to be provided at the bottom of the container 110 may have any desired shape such as an oval shape or a rectangular shape. Alternatively, the mark to be provided at the bottom of the container 110 may be scaled at predetermined intervals, or may be colored in different colors at predetermined intervals. The mark to be provided at the bottom of the container 110 may have different kinds of line at predetermined intervals. It is also possible to form the mark by combining selected two or more of the above mentioned types of mark.

In each of the first through fifth embodiments, the capsule medical device 10 is of a twin-lens type that has two image capturing units provided therein. However, the present invention is not limited to that arrangement, and the capsule medical device to be magnetically guided by a magnetically guiding system of the present invention may be a capsule medical device of a single-lens type that includes a single image capturing unit, or may be a capsule medical device of multi-lens type that includes three or more image capturing units. The image capturing direction of such a capsule medical device of a twin-lens or multi-lens type may be the direction of the long axis CL of the capsule medical device as described above, or may be the radial direction of the capsule-like casing 11 or a direction tilted with respect to the long axis CL.

In each of the first through fifth embodiments, the magnetically guiding system of the present invention guides the capsule medical device 10 with magnetic force. However, the magnetically guiding system of the present invention is not limited thereto and is applicable to magnetically guide a medical device that includes at least one magnet. For example, the magnetically guiding system of the present invention may magnetically guide a catheter including a magnet or may magnetically guide an endoscope.

In each of the first through fifth embodiments, the magnetically guiding system of the present invention guides the capsule medical device 10 with magnetic force. However, the present invention is not limited to that arrangement, and the present invention may be applied to a checking device that checks the characteristics of the magnet 19 in the capsule medical device 10.

The following is a description of such a checking device and a magnetically guiding system that uses the checking device. In the following description, a checking device that checks a capsule medical device housed in a predetermined package and a magnetically guiding system that magnetically guides the capsule medical device checked by the checking device and introduced into the body of a test subject are taken as examples. However, this embodiment does not limit the present invention.

Figure 18:
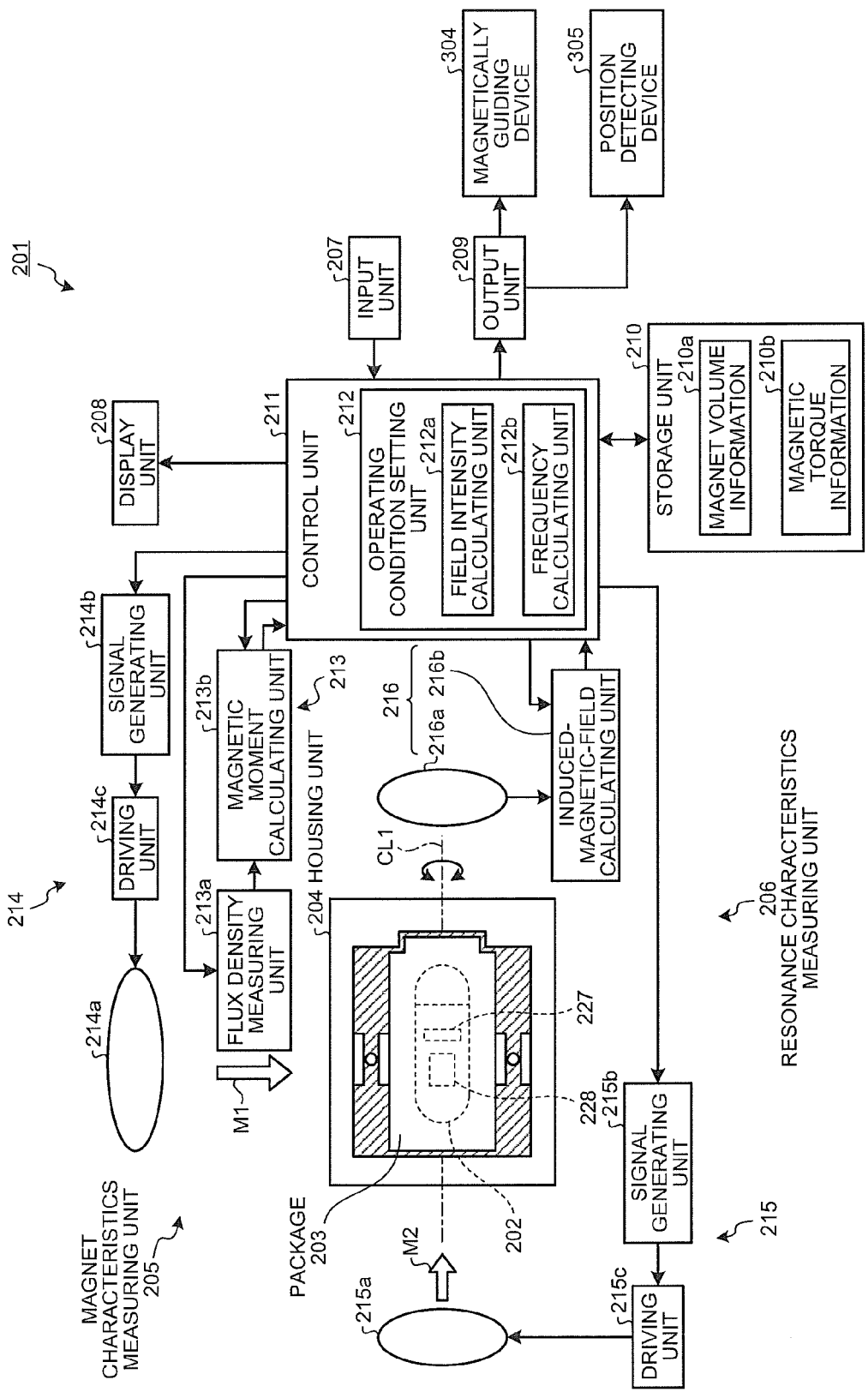
FIG. 18 is a block diagram schematically showing an example structure of a checking device in accordance with a sixth embodiment of the present invention.

FIG. 18 is a block diagram schematically showing an example structure of a checking device in accordance with a sixth embodiment of the present invention. As shown in FIG. 18, the checking device 201 in accordance with the sixth embodiment includes: a housing unit 204 that houses a capsule medical device 202 to be magnetically guided by a predetermined magnetically guiding device 304 together with the package 203 of the capsule medical device 202; a magnet characteristics measuring unit 205 that measures the characteristics of a magnet 227 provided inside the capsule medical device 202; and a resonance characteristics measuring unit 206 that measures the characteristics of a resonance circuit 228 provided inside the capsule medical device 202. The checking device 201 also includes: an input unit 207 that inputs various kinds of information; a display unit 208 that displays various kinds of information such as the conditions for operating the magnetically guiding device 304; an output unit 209 that outputs operating condition information and the likes to the magnetically guiding device 304; a storage unit 210 that stores various kinds of information; and a control unit 211 that controls the respective components of the checking device 201.

The capsule medical device 202 is a capsule-like medical device that obtains in-vivo images of a test subject, and has an image capturing function and a radio communication function inside a capsule-like casing. The capsule medical device 202 can be magnetically guided by the predetermined magnetically guiding device 304, and has the magnet 227 and the resonance circuit 228 provided inside the capsule-like casing. The capsule medical device 202 is subjected to a sterilizing treatment after its manufacture, and is then put into the package 203. After shipped to users such as medical doctors and nurses, the capsule medical device 202 is kept inside the package 203 until it is introduced into the body of a test subject.

The package 203 has such a structure that can accommodate the capsule medical device 202 therein, and has such an external shape that the long axis direction of the housed capsule medical device 202 can be visually recognized. The package 203 supports the sterilized capsule medical device 202 therein in a detachable manner, and houses the capsule medical device 202 in a sealed state. The capsule medical device 202 housed (supported) inside the package 203 cannot move freely inside the package 203 (that is, cannot change its relative position and direction with respect to the package 203).

The housing unit 204 functions as a supporting unit that supports the capsule medical device 202 to be checked. More specifically, the housing unit 204 has a concave portion (the shaded portion in FIG. 18) that can accommodate the package 203 while defining the direction of the package 203. The housing unit 204 supports the package 203 fitted with the concave portion in such a manner that a bearing structure allows the package 203 to rotate. The housing unit 204 houses and supports the capsule medical device 202 in a rotative manner via the package 203. In this case, the package 203 housed in the housing unit 204 can rotate about the central axis CL1 of the package 203. It is desirable that the central axis CL1 of the package 203 is parallel to the long axis of the capsule medical device 202 inside the package 203 (or the central axis CL2 of the later described capsule-like housing 220 in the longitudinal axis), and it is more desirable that the central axis CL1 of the package 203 is coincident with the long axis of the capsule medical device 202.

The magnet characteristics measuring unit 205 measures the characteristics of the magnet 227 provided in the capsule medical device 202. More specifically, the magnet characteristics measuring unit 205 measures the magnetic moment that is part of the characteristics of the magnet 227. The magnet characteristics measuring unit 205 includes a magnetic moment measuring unit 213 that measures the magnetic moment of the magnet 227 in the capsule medical device 202 housed in the housing unit 204, and a magnetization direction control unit 214 that magnetically controls the magnetization direction of the magnet 227.

The magnetic moment measuring unit 213 measures the magnetic moment of the magnet 227 through the measurement of the residual flux density of the magnet 227 inside the capsule medical device 202. The magnetic moment measuring unit 213 includes a flux density measuring unit 213a that measures the residual flux density of the magnet 227, and a magnetic moment calculating unit 213b that calculates the magnetic moment of the magnet 227 based on the result of the measurement carried out on the residual flux density by the flux density measuring unit 213.

The flux density measuring unit 213a is placed in the vicinity of the housing unit 204, and is located near the capsule medical device 202 in the package 203 housed in the housing unit 204. Under the control of the control unit 211, the flux density measuring unit 213a measures the residual flux density of the magnet 227 indicating the maximum intensity of the magnetic field (the maximum magnetic force) that can be generated from the magnet 227 in the capsule medical device 202 at that time. The flux density measuring unit 213a transmits the result of the measurement of the residual flux density of the magnet 227 to the magnetic moment calculating unit 213b.

Based on the result of the measurement carried out by the flux density measuring unit 213a, the magnetic moment calculating unit 213b calculates the magnetic moment of the magnet 227 in the capsule medical device 202. More specifically, the magnetic moment calculating unit 213b obtains the residual flux density of the magnet 227 in the capsule medical device 202 from the flux density measuring unit 213a. The magnetic moment calculating unit 213b obtains magnet volume information 210a that is read from the storage unit 210 by the control unit 211. Under the control of the control unit 211, the magnetic moment calculating unit 213b multiplies the residual flux density (the measured value) of the magnet 227 by the magnet volume information 210a (the volume of the magnet 227), so as to calculate the magnetic moment of the magnet 227. The magnetic moment calculating unit 213b then transmits the magnetic moment of the magnet 227 calculated in this manner as the result of the measurement of the magnetic moment of the magnet 227, to the control unit 211.

The magnetization direction control unit 214 applies a magnetic field to the capsule medical device 202, to control the magnetization direction of the magnet 227 inside the capsule medical device 202. More specifically, the magnetization direction control unit 214 includes a magnetic field generating coil 214a, a signal generating unit 214b, and a driving unit 214c. The magnetization direction control unit 214 magnetically rotates the capsule medical device 202 in the package 203 housed in the housing unit 204 together with the package 203. By doing so, the magnetization direction control unit 214 controls the magnetization direction of the magnet 227 in the capsule medical device 202 to be in the direction suited for the flux density measuring unit 213a to measure the residual flux density of the magnet 227.

Based on a current supplied from the driving unit 214c, the magnetic field generating coil 214a generates a guiding magnetic field M1, and applies the generated guiding magnetic field M1 to the capsule medical device 202 in the package 203. The guiding magnetic field M1 of the magnetic field generating coil 214a is a magnetic field for guiding the capsule medical device 202, and acts on the magnet 227 inside the capsule medical device 202. Accordingly, the capsule medical device 202 changes the magnetization direction of the magnet 227 toward the flux density measuring unit 213a, while rotating in accordance with the guiding magnetic field M1. In other words, the magnetic field generating coil 214a causes the magnetization direction of the magnet 227 in the capsule medical device 202 to be coincident with the magnetization direction of the guiding magnetic field M1 applied to the capsule medical device 202.

The signal generating unit 214b generates a current signal, under the control of the control unit 211. The signal generating unit 214b then transmits the current signal to the driving unit 214c. The driving unit 214c amplifies the current signal generated from the signal generating unit 214b, and transmits the amplified current signal to the magnetic field generating coil 214a. In this manner, the driving unit 214c supplies the power (the current) required for generating the guiding magnetic field M1 to the magnetic field generating coil 214a.

The resonance characteristics measuring unit 206 measures the resonance characteristics of the resonance circuit 228 provided inside the capsule medical device 202. More specifically, the resonance characteristics measuring unit 206 includes a magnetic field generating unit 215 that applies a magnetic field to the resonance circuit 228 inside the capsule medical device 202 housed in the housing unit 204, and an induced magnetic field measuring unit 216 that measures the intensity of an induced magnetic field generated from the resonance circuit 228.

The magnetic field generating unit 215 causes the resonance circuit 228 in the capsule medical device 202 to generate an induced magnetic field. The magnetic field generating unit 215 includes a magnetic field generating coil 215a, a signal generating unit 215b, and a driving unit 215c. Based on a current supplied from the driving unit 215c, the magnetic field generating coil 215a generates a magnetic field M2 while changing frequencies, and sequentially applies the magnetic field M2 of different frequencies to the capsule medical device 202 in the package 203. The magnetic field M2 generated from the magnetic field generating coil 215a acts on the resonance circuit 228 inside the capsule medical device 202. In this case, upon receipt of the magnetic field M2, the resonance circuit 228 is put into a resonant state and generates an induced magnetic field. The induced magnetic field generated from the resonance circuit 228 is a magnetic field that is output (as a response) from the resonance circuit 228 that has received the magnetic field M2 from the magnetic field generating coil 215a.

Under the control of the control unit 211, the signal generating unit 215b generates a frequency sweep signal, and transmits the generated frequency sweep signal to the driving unit 215c. The driving unit 215c electrically amplifies the frequency sweep signal generated from the signal generating unit 215b, and transmits the electrically amplified frequency sweep signal to the magnetic field generating coil 215a. In this manner, the driving unit 215c supplies the electric power (the current) required for generating the magnetic field M2 to the magnetic field generating coil 215a. Under the control of the control unit 211, the signal generating unit 215b may generate a signal of at least one frequency, and may transmit the generated signal of at least one frequency to the driving unit 215c. In other words, the frequency of the signal generated from the signal generating unit 215b (the electric signal to be applied to the magnetic field generating coil 215a) may be one frequency or continuous frequencies.

The induced magnetic field measuring unit 216 is designed to measure the intensity of the induced magnetic field generated from the resonance circuit 228 inside the capsule medical device 202. The induced magnetic field measuring unit 216 includes; a magnetic field sensor 216a that detects an induced magnetic field that is generated from the resonance circuit 228 in the capsule medical device 202 in response to the magnetic field M2 generated from the magnetic field generating coil 215a; and an induced magnetic field calculating unit 216b that performs predetermined signal processing on the results of the detection performed by the magnetic field sensor 216a.

The magnetic field sensor 216a may be embodied with the use of a coil or the like. The magnetic field sensor 216a detects the induced magnetic field generated from the resonance circuit 228 inside the capsule medical device 202, and converts the detected induced magnetic field into a voltage signal. The magnetic field sensor 216a then transmits the voltage signal as the result of the detection performed on the induced magnetic field from the resonance circuit 228, to the induced magnetic field calculating unit 216b.

The induced magnetic field calculating unit 216b may be embodied with the use of an A-D converting unit, an FFT processing unit, and the likes. The induced magnetic field calculating unit 216b obtains the voltage signal as the result of the detection performed on the induced magnetic field from the magnetic field sensor 216a, and performs a digital conversion on the obtained voltage signal. After that, the induced magnetic field calculating unit 216b performs a fast Fourier transform (FTT processing) on the digitized voltage signal, and transmits the result of the FFT processing (or the measured value of the induced magnetic field generated from the resonance circuit 228) to the control unit 211. The induced magnetic field calculating unit 216b may set the field intensity information about the magnetic field M2 from the magnetic field generating coil 215a as the operating parameter in advance, or may obtain the field intensity information from the control unit 211. In this case, the induced magnetic field calculating unit 216b may subtract the field intensity information (the set value of the field intensity) about the magnetic field M2 from the result (the measured value of the field intensity) of the magnetic field detection performed by the magnetic field sensor 216a, so as to obtain the measured value of the field intensity of the induced magnetic field generated from the resonance circuit 228.

The input unit 207 may be embodied with the use of input devices such as a keyboard, a mouse, and the likes. The input unit 207 inputs various kinds of information to the control unit 211, in accordance with input operations performed by a user such as a medical doctor, a nurse, or the like. The various kinds of information to be input to the control unit 211 from the input unit 207 include: magnet information that indicates the volume of the magnet 227 provided inside the capsule medical device 202; magnetic guiding information that indicates the magnetic torque required for the magnetically guiding device 304 to magnetically guide the capsule medical device 202 inside the body of a test subject; frequency information that indicates an alternating magnetic field of a position detecting device 305 that detects a position of the capsule medical device 202 in the body of the test subject; and various kinds of instruction information for issuing instructions to the control unit 211, for example.

The display unit 208 may be embodied with the use of a CRT display, a liquid crystal display, or the like. The display unit 208 displays various kinds of information instructed to display by the control unit 211. More specifically, the display unit 208 displays the result of the measurement of the residual flux density of the magnet 227 inside the capsule medical device 202 (the result of the measurement carried out by the flux density measuring unit 213a), the measured value of the induced magnetic field generated from the resonance circuit 228 inside the capsule medical device 202 (the result of the measurement carried out by the induced magnetic field measuring unit 216), the operating condition information about each of the magnetically guiding device 304 and the position detecting device 305, and the likes.

Under the control of the control unit 211, the output unit 209 performs an information communication with the magnetically guiding device 304, and transmits the information instructed to output by the control unit 211 (to be specific, the information about the conditions for operating the magnetically guiding device 304) to the magnetically guiding device 304. Under the control of the control unit 211, the output unit 209 also performs an information communication with the position detecting device 305, and transmits the information instructed to output by the control unit 211 (to be specific, the information about the conditions for operating the position detecting device 305) to the position detecting device 305. The output unit 209 may perform radio communications or wire communications with the magnetically guiding device 304 and the position detecting device 305.

The storage unit 210 may be embodied with the use of a storage medium that stores information in a rewritable fashion, such as a RAM, an EEPROM, a flash memory, or a hard disk. The storage unit 210 stores various kinds of information instructed to store by the control unit 211. Among the various kinds of stored information, the storage unit 210 transmits information instructed to read out by the control unit 211, to the control unit 211. Under the control of the control unit 211, the storage unit 210 stores the magnet volume information 210a that indicates the volume of the magnet 227 in the capsule medical device 202, and magnetic torque information 210b that indicates the torque required for magnetically guiding the capsule medical device 202 introduced into the body of a test subject. In addition to the magnet volume information 210a and the magnetic torque information 210b, the storage unit 210 also stores the result of the measurement carried out by the magnetic moment measuring unit 213, the result of the measurement carried out by the induced magnetic field measuring unit 216, the information about the conditions for operating the magnetically guiding device 304, the information about the conditions for operating the position detecting device 305, and the likes.

The control unit 211 controls the operations of the components (the magnet characteristics measuring unit 205, the resonance characteristics measuring unit 206, the input unit 207, the display unit 208, the output unit 209, and the storage unit 210) of the checking device 201, and also controls signal inputs and outputs among those components. More specifically, the control unit 211 controls the display unit 208 to display various kinds of information such as the results of the measurements and the information about the conditions for operating the magnetically guiding device 304. The control unit 211 also controls the output unit 209 to output the information about the operating conditions to the magnetically guiding device 304. The control unit 211 further controls the output unit 209 to output the information about the conditions for operating the position detecting device 305. The control unit 211 controls the storage unit 210 to store the various kinds of information such as the results of the measurements and the information about the conditions for operating the magnetically guiding device 304.

Based on instruction information that is input from the input unit 207, the control unit 211 also controls the magnet characteristics measuring unit 205 to measure the characteristics of the magnet 227 inside the capsule medical device 202. In this case, the control unit 211 controls the signal generating unit 214b to generate the current signal required for generating the guiding magnetic field M1. By controlling the signal generating unit 214b, the control unit 211 controls the magnetic field generating operation of the magnetic field generating coil 214a. The control unit 211 controls the magnetic field generating coil 214a to apply the guiding magnetic field M1 to the capsule medical device 202 for a predetermined period of time. By doing so, the control unit 211 directs the magnetization direction of the magnet 227 inside the capsule medical device 202 toward the flux density measuring unit 213a. After that, the control unit 211 controls the signal generating unit 214b to stop generating the current signal. By doing so, the control unit 211 stops the generation of the guiding magnetic field M1 from the magnetic field generating coil 214a (the application of a magnetic field to the capsule medical device 202). The control unit 211 controls the flux density measuring unit 213a to measure the residual flux density of the magnet 227 at the timing when the generation of the magnetic field is stopped, and then controls the magnetic moment calculating unit 213b to calculate the magnetic moment of the magnet 227 based on the measured value of the residual flux density. In this manner, the control unit 211 obtains the value calculated by the magnetic moment calculating unit 213b or the value measured by the magnetic moment measuring unit 213.

Based on instruction information that is input from the input unit 207, the control unit 211 further controls the resonance characteristics measuring unit 206 to measure the resonance characteristics of the resonance circuit 228 inside the capsule medical device 202. In this case, the control unit 211 controls the signal generating unit 215b to generate the current signal required for generating the magnetic field M2. By controlling the signal generating unit 215b, the control unit 211 controls the magnetic field generating operation of the magnetic field generating coil 215a. The control unit 211 also controls the induced magnetic field calculating unit 216b to calculate the measurement value of the induced magnetic field generated from the resonance circuit 228. In this manner, the control unit 211 obtains the measurement value of the induced magnetic field from the induced magnetic field calculating unit 216b.

The control unit 211 includes an operating condition setting unit 212 that sets the conditions for operating the magnetically guiding device 304 and the position detecting device 305. Based on the result of the measurement carried out by the magnet characteristics measuring unit 205 or the result of the measurement carried out by the resonance characteristics measuring unit 206, the operating condition setting unit 212 sets the conditions for operating the magnetically guiding device 304 to magnetically guide the capsule medical device 202 inside the body of a test subject, and the conditions for operating the position detecting device 305 to detect the position of the capsule medical device 202 being magnetically guided by the magnetically guiding device 304 inside the body of the test subject. The operating condition setting unit 212 includes a field intensity calculating unit 212a that calculates the field intensity condition for the magnetically guiding device 304, and a frequency calculating unit 212b that calculates the frequency condition for the position detecting device 305.

The field intensity calculating unit 212a calculates the field intensity condition for the magnetically guiding device 304, based on the result of the measurement carried out by the magnetic moment measuring unit 213. More specifically, the field intensity calculating unit 212a obtains the magnetic moment of the magnet 227 inside the capsule medical device 202 from the magnetic moment calculating unit 213b. The field intensity calculating unit 212a also obtains the magnetic torque information 210b that is read from the storage unit 210 under the control of the control unit 211. The field intensity calculating unit 212a divides the magnetic torque information 210b (the torque required for the magnetic guiding) by the magnetic moment (the measurement value) of the magnet 227, so as to calculate the field intensity. The field intensity calculated by the field intensity calculating unit 212a is the field intensity condition for the magnetically guiding device 304 to magnetically guide the capsule medical device 202 inside the body of the test subject. The operating condition setting unit 212 sets the result (the field intensity) of the calculation performed by the field intensity calculating unit 212a as the field intensity condition for the magnetically guiding device 304.

The frequency calculating unit 212b calculates the frequency condition for the position detecting device 305, based on the result of the FFT processing performed by the induced magnetic field calculating unit 216b. More specifically, the frequency calculating unit 212b obtains the measurement value of the induced magnetic field generated from the resonance circuit 228 (or the result of the FFT processing), from the induced magnetic field calculating unit 216b. The frequency calculating unit 212b then calculates the frequency at which the measurement value of the induced magnetic field becomes the local maximum and the frequency at which the measurement value of the induced magnetic field becomes the local minimum (or calculates each frequency before and after the resonance point of the resonance circuit 228). The frequencies calculated by the frequency calculating unit 212b represent the frequency condition for the position detecting device 305 to detect the magnetic field (the induced magnetic field) generated from the capsule medical device 202. The operating condition setting unit 212 sets the results (the frequencies) of the calculations performed by the frequency calculating unit 212b as the frequency condition for the position detecting device 305. Meanwhile, the frequency calculating unit 212b may calculate the resonance frequency of the resonance circuit 228, based on the result of the FFT processing performed by the induced magnetic field calculating unit 216b, and sets the resonance frequency as the frequency condition for the position detecting device 305.

The magnetically guiding device 304 is an external device for magnetically guiding the capsule medical device 202 introduced into the body of a test subject. The magnetically guiding device 304 performs an information communication with the output unit 209, to obtain the operating condition information that indicates the results of the condition setting operation by the operating condition setting unit 212. The operating condition setting information obtained from the operating condition setting unit 212 includes the field intensity condition calculated by the field intensity calculating unit 212a. The magnetically guiding device 304 sets the field intensity condition as the initial field intensity condition for magnetically guiding the capsule medical device 202 inside the body of a test subject. After that, the magnetically guiding device 304 adjusts the intensity of the magnetic field to be applied to the capsule medical device 202, when necessary. The magnetically guiding device 304 uses the field intensity condition set by the operating condition setting unit 212 as the maximum intensity value of the magnetic field required for magnetically guiding the capsule medical device 202 inside the body of the test subject.

The position detecting device 305 is an external device for detecting the position of the capsule medical device 202 introduced into the body of the test subject. The position detecting device 305 performs an information communication with the output unit 209, to obtain the operating condition information that indicate the result of the condition setting operation by the operating condition setting unit 212. The operating condition information obtained from the operating condition setting unit 212 includes the frequency condition calculated by the frequency calculating unit 212b. The position detecting device 305 appropriately selects one of the frequencies represented by the obtained frequency condition (to be more specific, the frequency equivalent to the local maximum value of the detected intensity of the induced magnetic field and the frequency equivalent to the local minimum value). The position detecting device 305 applies the magnetic field of the selected frequency to the capsule medical device 202 in the body of the test subject. By doing so, the position detecting device 305 detects the intensity of the magnetic field (the induced magnetic field) generated from the capsule medical device 202. Based on the detected intensity value of the induced magnetic field generated from the capsule medical device 202, the position detecting device 305 calculates (detects) the position of the capsule medical device 202 in the body of the test subject. Using the result of the position detecting operation by the position detecting device 305 to detect the position of the capsule medical device 202, the magnetically guiding device 304 magnetically guides the capsule medical device 202.

The frequency indicated by the frequency condition set by the operating condition setting unit 212 (or the result of the operation by the frequency calculating unit 212b) may be the resonance frequency of the resonance circuit 228 inside the capsule medical device 202. The position detecting device 305 may apply a magnetic field of the resonance frequency to the capsule medical device 202 inside the body of the test subject, so as to detect the position of the capsule medical device 202 inside the body of the test subject.

Figure 19:
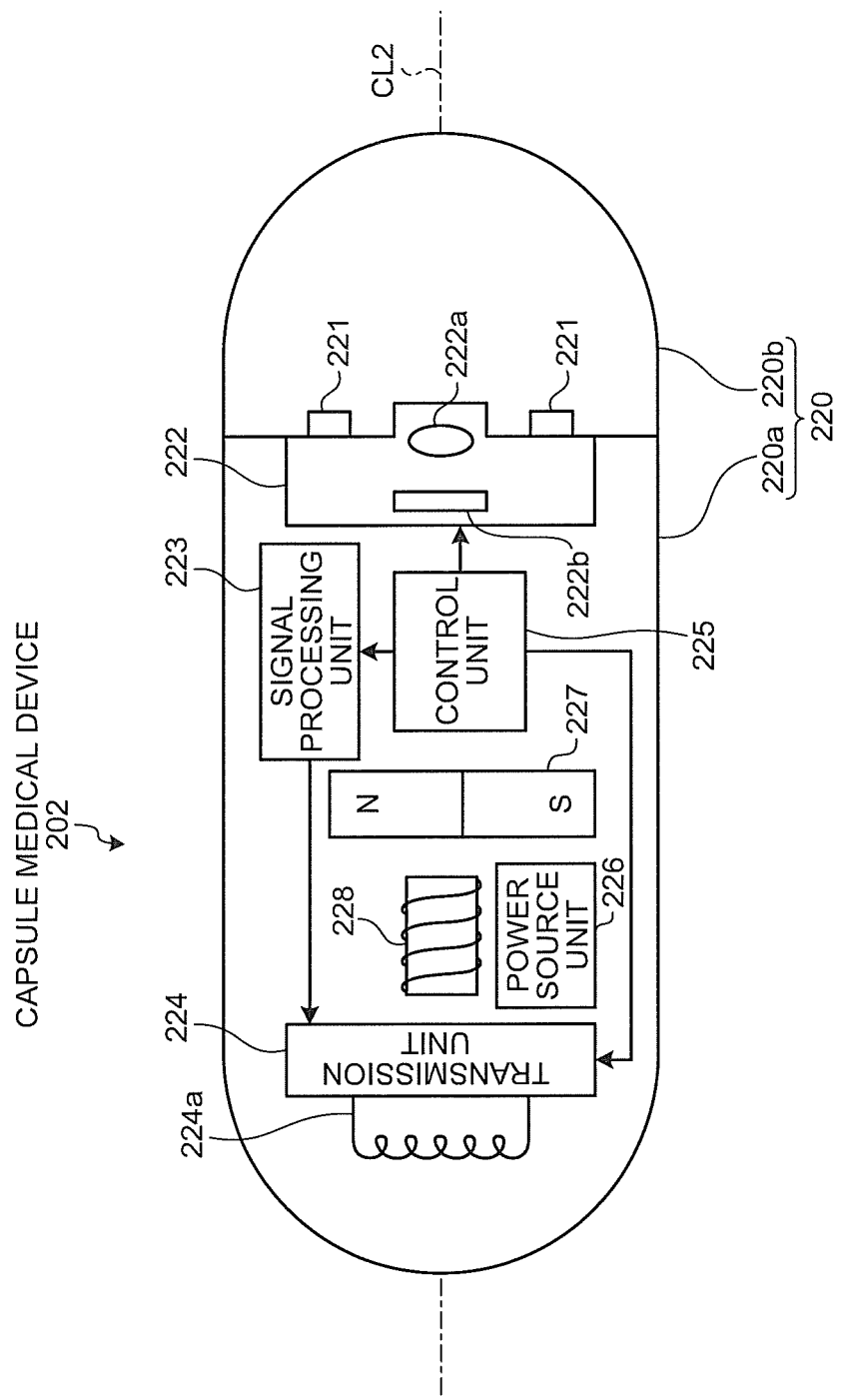
FIG. 19 is a schematic view showing an example structure of a capsule medical device to be checked by the checking device in accordance with the sixth embodiment of the present invention.

Next, the structure of the capsule medical device 202 to be checked by the checking device 201 in accordance with the sixth embodiment of the present invention will be described. FIG. 19 is a schematic view showing an example structure of the capsule medical device to be checked by the checking device in accordance with the sixth embodiment of the present invention. As shown in FIG. 19, the capsule medical device 202 to be checked includes the capsule-like casing 220 formed with a cylindrical casing 220a and a dome-like casing 220b, an illuminating unit 221 such as LEDs, and an image capturing unit 222 that captures images of a subject illuminated by the illuminating unit 221. The capsule medical device 202 also includes a signal processing unit 223 that generates the image signals of the image data captured by the image capturing unit 222, a transmission unit 224 that radio-transmits the image signals to the outside, a control unit 225 that controls the components of the capsule medical device 202, and a power source unit 226 such as a battery. The capsule medical device 202 further includes the magnet 227 that operates following an external magnetic field, and the resonance circuit 228 formed with a coil and a capacitor.

The capsule-like casing 220 has such a size as to be introduced into an internal organ of a test subject. One end (the opening end) of the cylindrical casing 220a having the other end in a dome-like shape is covered with the dome-like casing 220b. The dome-like casing 220b is a dome-like optical material that is transparent to light in a predetermined wavelength band (visible light, for example). The cylindrical casing 220a is a casing that is substantially not transparent to visible light. The illuminating unit 221, the image capturing unit 222, the signal processing unit 223, the transmission unit 224, the control unit 225, the power source unit 226, the magnet 227, and the resonance circuit 228 are housed in a liquid-tight manner in the capsule-like casing 220 formed with the cylindrical casing 220a and the dome-like casing 220b.

The illuminating unit 221 and the image capturing unit 222 form a function executing unit for capturing in-vivo images of a test subject when the capsule medical device 202 is introduced into the body of the test subject. More specifically, the illuminating unit 221 may be embodied with the use of a light emitting element such as LEDs, and illuminates the subject of the image capturing unit 222 through the dome-like housing 220b.

The image capturing unit 222 includes an optical system 222a such as a condenser lens, and a solid-state image sensor 222b such as a CCD or a CMOS image sensor. The image capturing unit 222 is fixed inside the capsule-like casing 220 in such a manner that the reference direction (the vertical direction of the light receiving face, for example) of the solid-state image sensor 222b is substantially coincident with the radial direction of the capsule-like casing 220. The optical system 222a gathers the light reflected from the subject illuminated by the illuminating unit 221, and forms an optical image of the subject on the light receiving face of the solid-state image sensor 222b. The solid-state image sensor 222b captures optical images of the subject or images (in-vivo images, for example) of the subject illuminated by the illuminating unit 221.

The signal processing unit 223 obtains signals that are photoelectrically converted by the solid-state image sensor 222b of the image capturing unit 222. The signal processing unit 223 performs predetermined signal processing on the obtained signals, so as to generate image signals that contain the image data (the in-vivo images and the likes) of the subject captured by the image capturing unit 222. The transmission unit 224 includes a coil-like antenna 224a, and performs radio communications with an external device through the antenna 224a. More specifically, the transmission unit 224 obtains the image signals generated from the signal processing unit 223, and performs modulation or the like on the obtained image signals, so as to generate radio signals including the image signals. The transmission unit 224 then radio-transmits the radio signals including the image signals to the outside through the antenna 224a.

The control unit 225 controls the components (the illuminating unit 221, the image capturing unit 222, the signal processing unit 223, and the transmission unit 224) of the capsule medical device 202, and also controls signal inputs and outputs among those components. More specifically, the control unit 225 controls the illuminating unit 221 and the image capturing unit 222 to operate in such timing that the image capturing unit 222 captures an image of the subject when the illuminating unit 221 illuminates the subject of the image capturing unit 222. The control unit 225 controls the illuminating unit 221 and the image capturing unit 222 to repeat the image capturing operation at predetermined time intervals (every 0.5 seconds, for example). The control unit 225 also controls the signal processing unit 223 and the transmission unit 224 to radio-transmit the image signals including the image data captured by the image capturing unit 222, to the outside.

The power source unit 226 may be embodied with the use of a switch circuit and a button battery or the like. When switched on by the switch circuit, the power source unit 226 supplies electric power to the illuminating unit 221, the image capturing unit 222, the signal processing unit 223, the transmission unit 224, and the control unit 225. When switched off by the switch circuit, the power source unit 226 stops the supply of electric power to those components. The switch circuit of the power source unit 226 may be a magnetic switch that switches on and off the power source unit 226 by virtue of the actions of a magnetic field applied from the outside, or may be an optical switch that switches on and off the power source unit 226 by virtue of optical signals such as infrared rays entering from the outside.

The magnet 227 may be a permanent magnet, for example, and is placed at a predetermined position inside the capsule-like casing 220 (placed in the vicinity of the center portion of the capsule-like casing 220, for example). In this case, the magnet 227 is fixed in the capsule-like casing 220 in such a manner that the direction perpendicular to the central axis CL2 of the longitudinal direction of the capsule-like casing 220 (or the radial direction of the capsule-like casing 220) is substantially coincident with the magnetization direction. The magnet 227 operates in accordance with the magnetic field generated from the magnetically guiding device 304 located outside, so as to move the capsule medical device 202 or stop the capsule medical device 202 at a desired location inside the body of a test subject. Accordingly, the capsule medical device 202 having the magnet 227 provided therein can be magnetically guided by the magnetically guiding device 304 located outside.

The resonance circuit 228 may be embodied by connecting a coil and a capacitor, and may be fixed inside the capsule-like casing 220 in such a manner that the axial direction of the coil is substantially coincident with the longitudinal direction of the capsule-like casing 220, for example. The resonance circuit 228 has a predetermined resonance frequency, and generates an induced magnetic field in response to a magnetic field applied from the outside (to be more specific, the magnetic field M2 of the magnetic field generating coil 215a or the magnetic field of the position detecting device 305).

Figure 20:
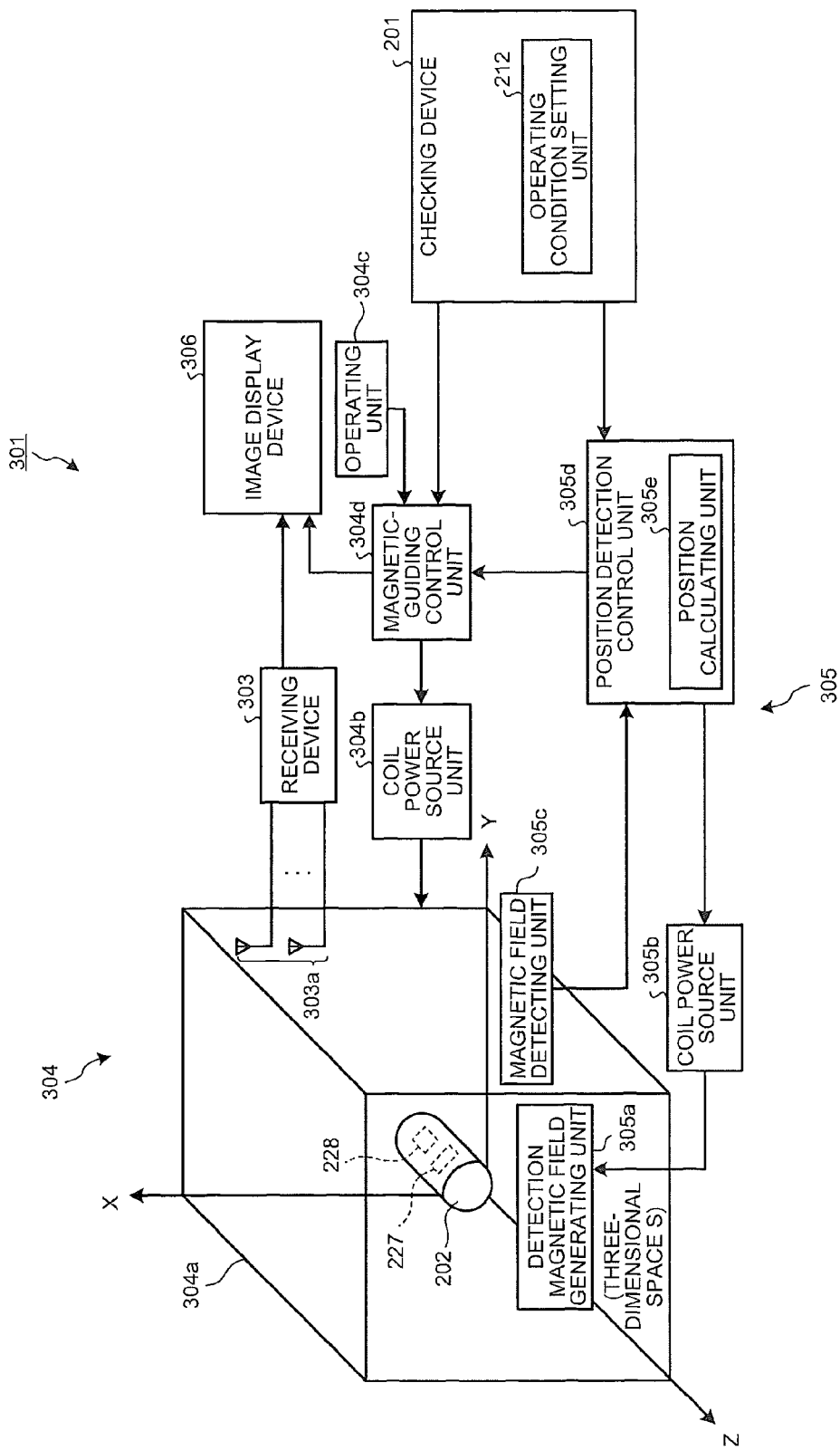
FIG. 20 is a block diagram schematically showing an example structure of a magnetically guiding system in accordance with the sixth embodiment of the present invention.

Next, a magnetically guiding system in accordance with the sixth embodiment of the present invention will be described. FIG. 20 is a block diagram schematically showing an example structure of the magnetically guiding system in accordance with the sixth embodiment of the present invention. As shown in FIG. 20, the magnetically guiding system 301 in accordance with the sixth embodiment includes: the checking device 201 that checks the capsule medical device 202 to be introduced into the body of a test subject; the capsule medical device 202 to be introduced into the body of the test subject; a receiving device 303 that receives in-vivo image groups captured by the capsule medical device 202 inside the body of the test subject; the magnetically guiding device 304 that magnetically guides the capsule medical device 202 inside the body of the test subject; the position detecting device 305 that detects the position and orientation of the capsule medical device 202 inside the body of the test subject; and an image display device 306 that displays various kinds of information such as the in-vivo images captured by the capsule medical device 202 inside the body of the test subject.

The capsule medical device 202 has the image capturing function and the radio communication function, as shown in FIG. 19 described above. When introduced into an internal organ of a test subject via the oral route, the capsule medical device 202 sequentially captures in-vivo images of the test subject, and sequentially radio-transmits the obtained in-vivo images to the receiving device 303. The capsule medical device 202 also includes the magnet 227 and the resonance circuit 228, as described above. The capsule medical device 202 is magnetically guided by the magnetically guiding device 304, and the position of the capsule medical device 202 is detected by the position detecting device 305.

The receiving device 303 has receiving antennas 303a, and receives the in-vivo images of the test subject from the capsule medical device 202 via the receiving antennas 303a. More specifically, the receiving antennas 303a are scattered on the surface of the body of the test subject having the capsule medical device 202 being introduced into patient's digestive tract. The receiving antennas 303a catch radio signals transmitted from the capsule medical device 202 that is moving (or is magnetically guided) through the digestive tract. The receiving device 303 receives radio signals from the capsule medical device 202 via the receiving antennas 303a. The receiving device 303 then performs a predetermined demodulating operation or the like on the received radio signals, to extract the image signals contained in the radio signals. The image signals extracted by the receiving device 303 contain the in-vivo images captured by the capsule medical device 202. The receiving device 303 then sequentially transmits the image signals from the capsule medical device 202 to the image display device 306.

The magnetically guiding device 304 is designed to magnetically guide the capsule medical device 202 inside the body of the test subject. The magnetically guiding device 304 includes: a guiding magnetic field generating unit 304a that generates a guiding magnetic field for magnetically guiding the capsule medical device 202 inside the body of the test subject; a coil power source unit 304b that supplies a current to the coil of the guiding magnetic field generating unit 304a; an operating unit 304c that is designed for starting the magnetic guiding of the capsule medical device 202; and a magnetic-guiding control unit 304d that controls the components of the magnetically guiding device 304.

The guiding magnetic field generating unit 304a may be embodied with a combination of electromagnets such as Helmholtz coils, and generates a guiding magnetic field that allows the magnetic guiding of the capsule medical device 202 inside the body of the test subject. More specifically, the guiding magnetic field generating unit 304a has a triaxial orthogonal coordinate system defined by three axes (X-axis, Y-axis, and Z-axis) perpendicular to one another (hereinafter referred to as the absolute coordinate system), and generates a magnetic field of desired intensity in each of the axis directions (the X-axis direction, the Y-axis direction, and the Z-axis direction) of the absolute coordinate system. The guiding magnetic field generating unit 304a generates a guiding magnetic field that is a three-dimensional rotating magnetic field or gradient magnetic field formed by the magnetic fields of the respective axis directions of the absolute coordinate system inside the three-dimensional space S of the absolute coordinate system (or inside the space surrounded by the electromagnets of the guiding magnetic field generating unit 304a). The guiding magnetic field generating unit 304a applies the guiding magnetic field to the magnet 227 inside the capsule medical device 202 located inside the body of the test subject (not shown) on a bed moved to the inside of the three-dimensional space S. Using the guiding magnetic field, the guiding magnetic field generating unit 304a magnetically guides the capsule medical device 202.

The coil power source unit 304b supplies the current required for the guiding magnetic field generating unit 304a to generate the guiding magnetic field to be applied to the capsule medical device 202 inside the body of the test subject. More specifically, the coil power source unit 304b has power source units for the respective coils (not shown) of the guiding magnetic field generating unit 304a. Under the control of the magnetic-guiding control unit 304d, the coil power source unit 304b supplies an alternating current to each of the coils of the guiding magnetic field generating unit 304a. By doing so, the coil power source unit 304b causes the guiding magnetic field generating unit 304a to generate the guiding magnetic field.

The operating unit 304c may be embodied with the use of an input device such as a joystick and an input button. In accordance with an input operation by a user such as a medical doctor or a nurse, the operating unit 304c inputs instruction information to the magnetic-guiding control unit 304d, so that the capsule medical device 202 is magnetically guided.

The magnetic-guiding control unit 304b controls the amount of current to be supplied from the coil power source unit 304b to the guiding magnetic field generating unit 304a, based on the instruction information that is input from the operating unit 304c. By controlling the coil power source unit 304b, the magnetic-guiding control unit 304d controls the guiding magnetic field generating operation of the guiding magnetic field generating unit 304a. In this case, the magnetic-guiding control unit 304d obtains the location information (hereinafter referred to as the capsule location information) and the direction information (hereinafter referred to as the capsule direction information) about the capsule medical device 202 inside the body of the test subject, from the position detection control unit 305d of the position detecting device 305 described later. Based on the capsule location information and the capsule direction information, the magnetic-guiding control unit 304d controls the field intensity and the field direction of the guiding magnetic field to be applied to the capsule medical device 202. By controlling the field intensity and the field direction of the guiding magnetic field, the magnetic-guiding control unit 304d controls the magnetic guiding of the capsule medical device 202 to be directed toward the desired location or in the desired direction in accordance with the instruction information input from the operating unit 304c. The magnetic-guiding control unit 304d transmits magnetic-guiding information to the image display device 306, with the magnetic-guiding information including the information about the field intensity and field direction of the guiding magnetic field observed when the magnetic guiding of the capsule medical device 202 is controlled.

As described above, the magnetic-guiding control unit 304d obtains the operating condition information that is set by the operating condition setting unit 212, from the checking device 201. The magnetic-guiding control unit 304d sets the field intensity condition included in the obtained operating condition information as the initial field intensity condition for magnetically guiding the capsule medical device 202 inside the body of the test subject. In this case, the magnetic-guiding control unit 304d sets the field intensity condition at the maximum intensity value of the guiding magnetic field required for magnetically guiding the capsule medical device 202 inside the body of the test subject. The magnetic-guiding control unit 304d controls the guiding magnetic field within a range under the field intensity condition that is initially set.

The position detecting device 305 detects at least one of the position and the orientation of the capsule medical device 202 inside the body of the test subject located in the three-dimensional space S as described above. More specifically, the position detecting device 305 includes: a detection magnetic field generating unit 305a that applies a detection magnetic field to the resonance circuit 228 inside the capsule medical device 202; a coil power source unit 305b that supplies a current to the detection magnetic field generating unit 305a; a magnetic field detecting unit 305c that detects an induced magnetic field generated from the resonance circuit 228; and a position detection control unit 305d that controls the components of the position detecting device 300, and obtains the capsule location information and the capsule direction information.

The detection magnetic field generating unit 305a may be embodied with the use of one or more coil(s), and generates a detection magnetic field that is an alternating magnetic field for detecting at least one of the position and the orientation of the capsule medical device 202 inside the body of the test subject. Based on the current supplied from the coil power source unit 305b, the detection magnetic field generating unit 305a generates a detection magnetic field having the optimum intensity and orientation for the position of the resonance circuit 228 and the coil axis direction in the three-dimensional space S. The detection magnetic field generating unit 305a then applies the detection magnetic field to the resonance circuit 228 inside the capsule medical device 202. By virtue of the action of the detection magnetic field, the detection magnetic field generating unit 305a causes the resonance circuit 228 to generate an induced magnetic field.

The coil power source unit 305b includes one or more power source unit(s) corresponding to the number of coils in the detection magnetic field generating unit 305a. Under the control of the position detection control unit 305d, the coil power source unit 305b supplies an alternating current to the coils of the detection magnetic field generating unit 305a. By doing so, the coil power source unit 305b causes the detection magnetic field generating unit 305a to generate the detection magnetic field.

The magnetic field detecting unit 305c detects the induced magnetic field generated from the resonance circuit 228 as the magnetic field required for detecting at least one of the position and the orientation of the capsule medical device 202 inside the body of the test subject. The magnetic field detecting unit 305c transmits the result of the operation performed to detect the induced magnetic field generated from the resonance circuit 228, to the position detection control unit 305d.

When at least one of the position and orientation of the capsule medical device 202 inside the body of the test subject is detected, the position detection control unit 305d controls the detection magnetic field generating unit 305a, the coil power source unit 305b, and the magnetic field detecting unit 305c as described above. More specifically, the position detection control unit 305d obtains the operating condition information set by the operating condition setting unit 212 from the checking device 201, as described above. The position detection control unit 305d sets the frequency condition included in the obtained operating condition information as the operating condition for generating the detection magnetic field. The position detection control unit 305d controls the detection magnetic field generating unit 305a to apply a detection magnetic field of the frequency defined by the set frequency condition, to the resonance circuit 228 of the capsule medical device 202 inside the body of the test subject. In this case, the position detection control unit 305d controls the amount of current to be supplied from the coil power source unit 305b to the detection magnetic field generating unit 305a. By controlling the amount of current, the position detection control unit 305d controls the detection magnetic field generating operation of the detection magnetic field generating unit 305a.

The position detection control unit 305d includes a position calculating unit 305e. By controlling inputs and outputs of signals from the magnetic field detecting unit 305c, the position detection control unit 305d obtains the result of the detecting operation by the magnetic field detecting unit 305c to detect the guiding magnetic field generated from the resonance circuit 228. Based on the result of the induced magnetic field detection obtained from the magnetic field detecting unit 305c, the position calculating unit 305e calculates at least one of the positional coordinates and the directional vector of the capsule medical device 202 inside the body of the test subject. The positional coordinates calculated by the position calculating unit 305e are the capsule location information that indicates the position of the capsule medical device 202 in the three-dimensional space S. The directional vector calculated by the position calculating unit 305e is the capsule direction information that indicates the orientation of the capsule medical device 202 in the three-dimensional space S. The position detection control unit 305d transmits the capsule location information and the capsule direction information calculated (or detected) in the above manner to the magnetic-guiding control unit 304d. The capsule location information and the capsule direction information calculated by the position detection control unit 305d are then transmitted together with the magnetic guiding information from the magnetic-guiding control unit 304d to the image display device 306.

The image display device 306 has a structure similar to a workstation that displays various kinds of information such as the in-vivo images captured by the capsule medical device 202. More specifically, the image display device 306 sequentially obtains the image signals received by the receiving device 303. Based on the obtained image signals, the image display device 306 generates the images captured by the capsule medical device 202 or the in-vivo images of the test subject. The image display device 306 sequentially displays the generated in-vivo images of the test subject on its display, and sequentially stores the data about the in-vivo images into a storage medium.

The image display device 306 also obtains the magnetic guiding information from the magnetic-guiding control unit 304d, and further obtains the capsule location information and the capsule direction information from the position detection control unit 305d via the magnetic-guiding control unit 304d. Based on the magnetic guiding information, the capsule location information, and the capsule direction information, the image display device 306 displays various kinds of information that is useful in magnetically guiding the capsule medical device 202. The various kinds of information includes the information about the position at which the currently displayed in-vivo image is captured, the movement locus of the capsule medical device 202 inside the body of the test subject, the direction and intensity of the guiding magnetic field applied to the capsule medical device 202 to be magnetically guided. A user (an operator) such as a medical doctor or a nurse performs the magnetic guiding of the capsule medical device 202 by referring to the various kinds of information displayed on the image display device 306, while observing the in-vivo image of the test subject shown on the image display device 306.

Figure 21:
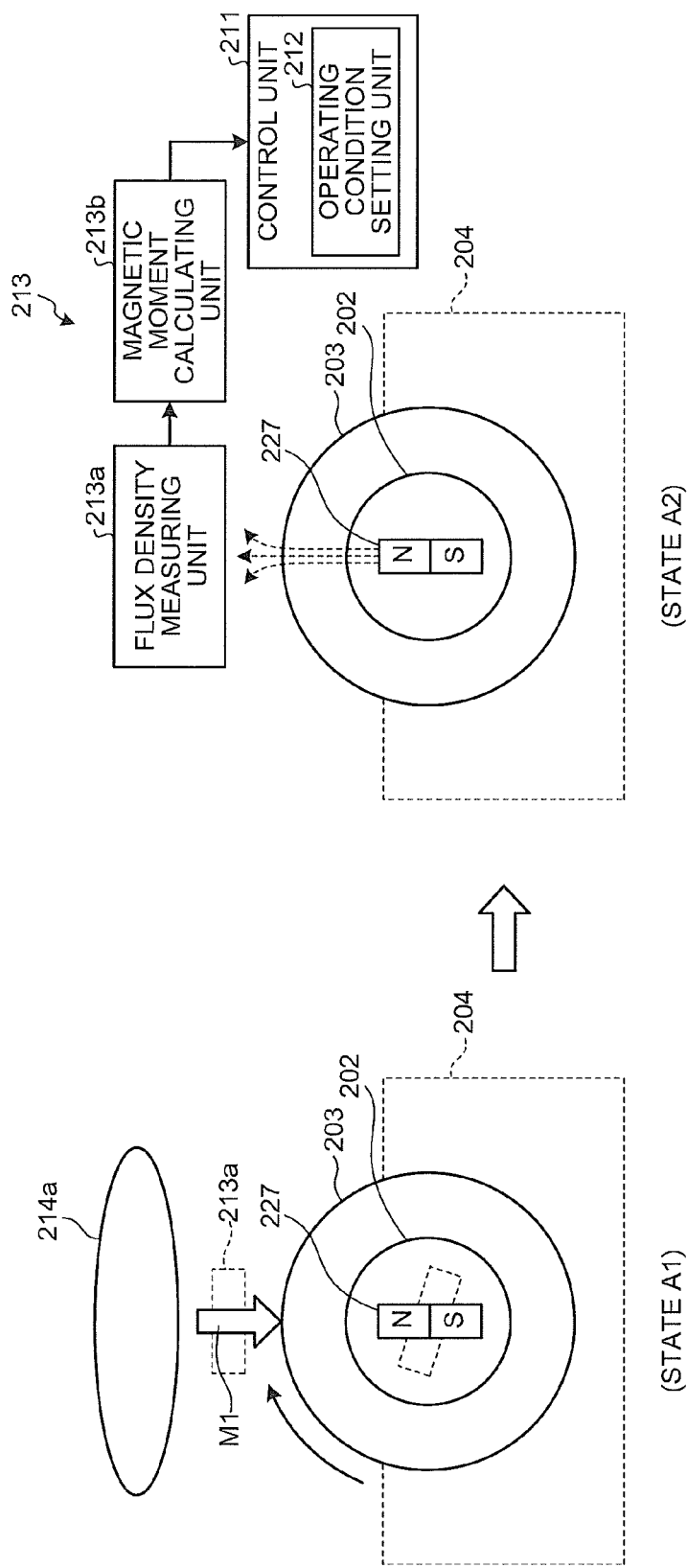
FIG. 21 is a schematic view showing an example case where the magnetic moment of a magnet inside the capsule medical device is measured by the checking device in accordance with the sixth embodiment of the present invention.

Next, the operation of the checking device 201 in accordance with the sixth embodiment of the present invention will be described. FIG. 21 is a schematic view illustrating an example case where the checking device in accordance with the sixth embodiment of the present invention measures the magnetic moment of the magnet inside the capsule medical device. Referring to FIG. 21, the operation by the checking device 201 to measure the magnetic moment of the magnet 227 inside the capsule medical device 202 will be described in detail.

As described above, the capsule medical device 202 to be checked is accommodated in the package 203 that is housed in the concave portion of the housing unit 204 (see FIG. 18). The housing unit 204 rotatably supports the capsule medical device 202 via the package 203. With this arrangement, the capsule medical device 202 housed in the housing unit 204, as well as the package 203, can rotate about the central axis CL1 of the package 203. The capsule medical device 202 has an external shape that is rotationally symmetrical with respect to the central axis CL2 of the capsule-like casing 220. Therefore, it is difficult to visually recognize the magnetization direction of the magnet 227 inside the capsule medical device 202.

Under the control of the control unit 211, the magnetic field generating coil 214a generates the guiding magnetic field M1, and applies the guiding magnetic field M1 to the capsule medical device 202 inside the package 203 housed in the housing unit 204. In this case, the guiding magnetic field M1 acts on the magnet 227 inside the capsule medical device 202, and the magnet 227 operates in accordance with the guiding magnetic field M1. The capsule medical device 202 as well as the package 203 rotates about the central axis CL1 by the action of the magnet 227. Accordingly, the magnetization direction of the magnet 227 shifts toward the flux density measuring unit 213a of the magnetic moment measuring unit 213. As a result, the magnet 227 has its magnetization direction shifting toward the flux density measuring unit 213a (state A1).

In a state where the capsule medical device 202 directs the magnetization direction of the magnet 227 toward the flux density measuring unit 213a, the magnetic field generating coil 214a stops generating the guiding magnetic field M1, under the control of the control unit 211. With this arrangement, the flux density measuring unit 213a can receive the magnetic field from the magnet 227, without receiving the guiding magnetic field M1 from the magnetic field generating coil 214a. Under the control of the control unit 211, the flux density measuring unit 213a measures the flux density of the magnet 227, and calculates the residual flux density of the magnet 227. The magnetic moment calculating unit 213b of the magnetic moment measuring unit 213 multiplies the value of the residual flux density measured by the flux density measuring unit 213a by the value of the volume of the magnet 227 according to the magnet volume information 210a. In this manner, the magnetic moment calculating unit 213b calculates the magnetic moment of the magnet 227 (state A2).

After that, the magnetic moment measuring unit 213 transmits the value of the magnetic moment of the magnet 227 calculated by the magnetic moment calculating unit 213b as the measurement value of the magnetic moment to the control unit 211. The control unit 211 obtains the measurement value of the magnetic moment of the magnet 227 from the magnetic moment measuring unit 213. Based on the obtained measurement value of the magnetic moment, the operating condition setting unit 212 sets the field intensity condition for the magnetically guiding device 304 to magnetically guide the capsule medical device 202 inside the body of the test subject.

The capsule medical device 202 checked by the checking device 201 is taken out of the package 203, and is introduced into an internal organ of the test subject via the oral route. Accordingly, immediately before the capsule medical device 202 is introduced into the body of the test subject, the checking device 201 can check the characteristics (such as the magnetic moment) of the magnet 227 and the resonance characteristics (such as the frequency) of the resonance circuit 228 inside the capsule medical device 202. Before the magnetically guiding device 304 starts magnetically guiding the capsule medical device 202, the checking device 201 can set the field intensity condition in advance, based on the characteristics of the magnet 227 (to be more specific, the magnetic moment of the magnet 227). Further, the checking device 201 can set the frequency condition for the position detecting device 305 in advance, based on the resonance characteristics of the resonance circuit 228 (to be more specific, the result of the FFT processing performed by the induced magnetic field calculating unit 216b or the like).

Based on the field intensity condition set by the checking device 201, the magnetically guiding device 304 can easily set the initial operating condition for magnetically guiding the capsule medical device 202 inside the body of the test subject. Accordingly, the magnetically guiding device 304 can magnetically guide the capsule medical device with high efficiency, without unnecessary consumption of electric power due to excessive application of a magnetic field to the capsule medical device 202. Based on the frequency condition that is set by the checking device 201, the position detecting device 305 can easily set the operating condition for detecting at least one of the position and orientation of the capsule medical device 202 inside the body of the test subject.

Accordingly, the position detecting device 305 can detect the position and orientation of the capsule medical device 202 inside the body of the test subject with high precision, in accordance with the resonance characteristics of the capsule medical device 202.

As described above, in the sixth embodiment of the present invention, the residual flux density of the magnet inside the capsule medical device kept by a user such as a medical doctor or a nurse is measured by the flux density measuring unit. Based on the result of the measurement of the residual flux density, the magnetic moment of the magnet is calculated by the magnetic moment calculating unit. Accordingly, the characteristics of the magnet (such as the magnetic moment of the internal magnet at that time) inside the capsule medical device that is difficult to visually recognize from the outside of the capsule medical device can be readily checked. Thus, a checking device that can check the characteristics of the magnet inside the capsule medical device immediately before the capsule medical device is introduced into the body of a test subject can be realized.

By using the checking device in accordance with the sixth embodiment, a user can recognize the characteristics of the magnet of the capsule medical device to be magnetically guided by the magnetically guiding device at that time by means of information displayed on the display unit. Based on the result of the check made on the magnet characteristics, the initial operating condition for the magnetically guiding device can be set. Accordingly, the magnetically guiding device can apply the required minimum magnetic field to the capsule medical device inside the body of a test subject, and can magnetically guide the capsule medical device inside the body of the test subject with high efficiency, without unnecessary consumption of electric power.

In the sixth embodiment, the characteristics of the magnet of the capsule medical device that has been sterilized and is accommodated in the package are checked. Accordingly, the magnetic moment of the magnet inside the capsule medical device can be measured without taking the capsule medical device out of the package. Thus, the sterilized state of the capsule medical device can be maintained until immediately before the capsule medical device is introduced into the body of the test subject.

Further, in the sixth embodiment, the capsule medical device to be checked is rotatably supported by the housing unit, and a magnetic field from the outside acts on the magnet inside the capsule medical device, so as to cause the magnetization direction of the magnet to shift toward the flux density measuring unit. With this arrangement, the magnetization direction of the magnet can easily shift toward the flux density measuring unit, when the residual flux density of the magnet inside the capsule medical device is measured. Accordingly, the residual flux density can be accurately measured.

Also, in the magnetically guiding system in accordance with the sixth embodiment, the operating condition setting unit sets the field intensity condition for the magnetically guiding device, based on the result of the measurement carried out by the flux density measuring unit. The output unit then transmits the field intensity condition to the magnetically guiding device. Accordingly, the checking device of the present invention checks the characteristics of the magnet in the capsule medical device, and the magnetically guiding device can easily set the field intensity condition based on the result of the setting operation by the operating condition setting unit, as the initial operating condition for magnetically guiding the capsule medical device inside the body of the test subject. As a result, the magnetically guiding device can easily perform efficient magnetic guiding of the capsule medical device inside the body of the test subject.

Further, in the sixth embodiment, the resonance characteristics of the resonance circuit inside the capsule medical device are measured by the resonance characteristics measuring unit, so that a user can check the resonance characteristics of the resonance circuit immediately before the capsule medical device is introduced into the body of the test subject. Based on the result of the operation to check the resonance characteristics, the initial operating condition for the magnetically guiding device can be properly set by means of information displayed on the display unit. Based on the initial operating condition, the position detecting unit of the magnetically guiding device can obtain the information about the inherent characteristics of the resonance circuit inside the capsule medical device. Accordingly, the position detecting unit can detect the position and orientation of the capsule medical device by adjusting the measurement frequency to the resonance point of the resonance circuit. As a result, there is no need to widen the measurement frequency spacing by taking frequency shifts into account, and the position of the capsule medical device inside the body of the test subject can be detected with high precision.

Also, in the magnetically guiding system in accordance with the sixth embodiment, the operating condition setting unit sets the frequency condition for the magnetically guiding device, based on the result of the measurement carried out by the resonance characteristics measuring unit. The output unit then transmits the frequency condition to the magnetically guiding device. With this arrangement, the checking device in accordance with this embodiment checks the resonance characteristics of the capsule medical device, and the position detecting unit of the magnetically guiding device sets the frequency condition based on the result of the setting operation by the operating condition setting unit, as the initial operating condition (the measurement frequency) for detecting the position of the capsule medical device inside the body of the test subject. As a result, the magnetically guiding device can readily detect the position of the capsule medical device inside the body of the test subject with high precision.

Next, a seventh embodiment of the present invention will be described. In the above described sixth embodiment, the capsule medical device 202 to be checked is rotatably supported by the housing unit 204, and the magnetization direction of the magnet 227 inside the capsule medical device 202 is controlled to shift toward the flux density measuring unit 213a by virtue of the action of the guiding magnetic field M1 generated from the magnetic field generating coil 214a. In the seventh embodiment, on the other hand, the capsule medical device to be checked is fixed by a housing unit, and a measuring device of a flux density measuring unit rotatively moves around the capsule medical device, to sequentially measure flux densities of the magnet inside the capsule medical device.

Figure 22:
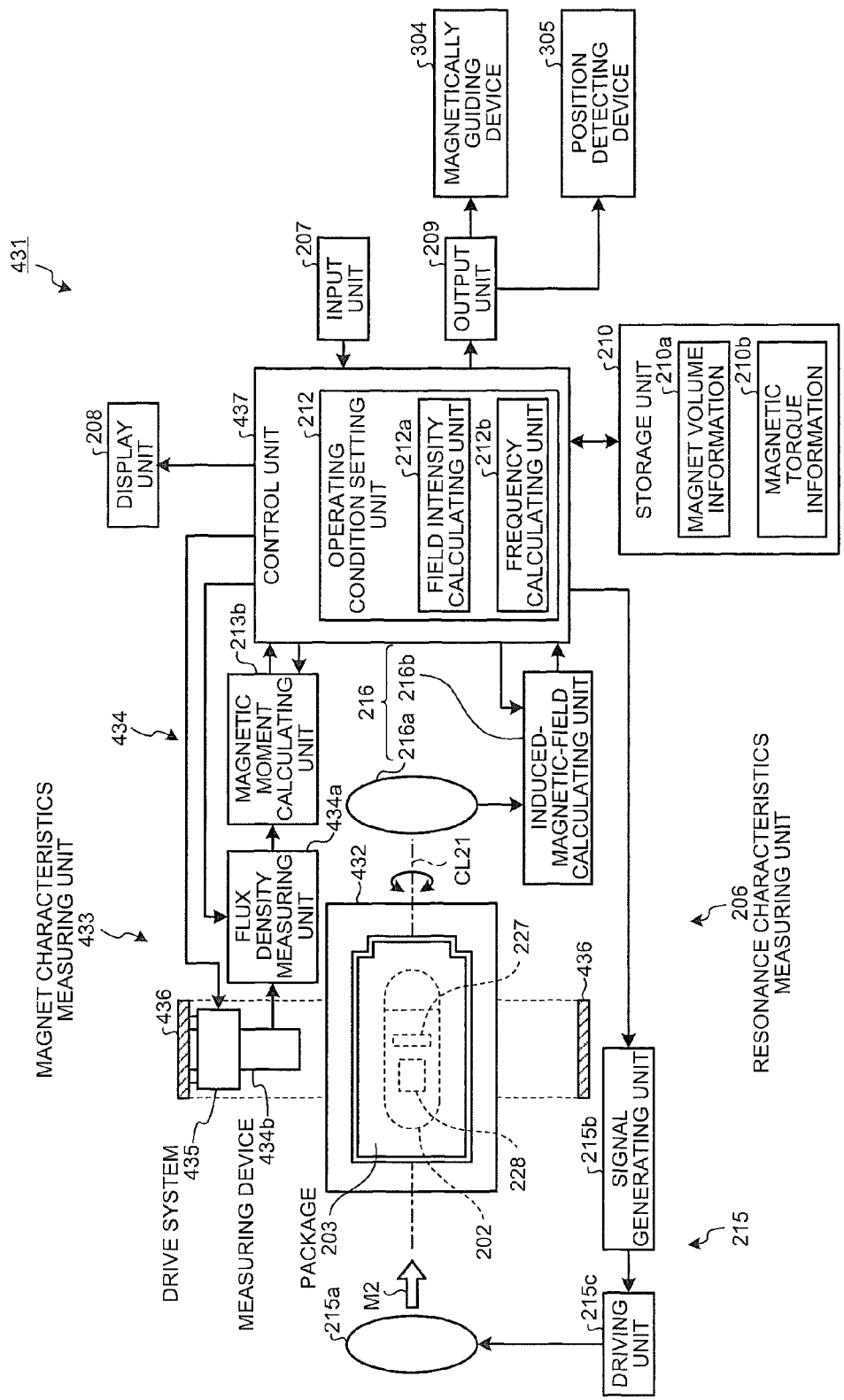
FIG. 22 is a block diagram schematically showing an example structure of a checking device in accordance with a seventh embodiment of the present invention.

FIG. 22 is a block diagram schematically showing an example structure of a checking device in accordance with the seventh embodiment of the present invention. As shown in FIG. 22, the checking device 431 in accordance with the seventh embodiment is the same as the checking device 201 of the sixth embodiment, except that the housing unit 204 is replaced with a housing unit 432, the magnet characteristics measuring unit 205 is replaced with a magnet characteristics measuring unit 433, and the control unit 211 is replaced with a control unit 437. In this checking device 431, the magnet characteristics measuring unit 433 includes a magnetic moment measuring unit 434 in place of the magnetic moment measuring unit 213 of the sixth embodiment, and a drive system 435 and a rail 436 in place of the magnetization direction control unit 214. A magnetically guiding system in accordance with the seventh embodiment is the same as the magnetically guiding system 301 of the sixth embodiment (see FIG. 20), except that the checking device 201 is replaced with the checking device 431. The other configurations of this embodiment are the same as those of the sixth embodiment, and the same components as those of the sixth embodiment are denoted by the same reference numerals as those used in the sixth embodiment.

The housing unit 432 functions as a supporting unit that supports the capsule medical device 202 to be checked. More specifically, the housing unit 432 defines the direction of the package 203, and has a concave portion that has such a shape as to be engaged with the external shape of the package 203. The housing unit 432 secures and detachably supports the package fitted with the concave portion. In this manner, the housing unit 432 houses the capsule medical device 202, while securing and supporting the capsule medical device 202 via the package 203.

The magnet characteristics measuring unit 433 measures the characteristics of the magnet 227 provided inside the capsule medical device 202. More specifically, the magnet characteristics measuring unit 433 measures the magnetic moment as an example of the characteristics of the magnet 227 inside the capsule medical device 202 secured and supported by the housing unit 432 via the package 203. As shown in FIG. 22, the magnet characteristics measuring unit 433 includes the magnetic moment measuring unit 434 that measures the magnetic moment of the magnet 227, the drive system 435 that rotatively moves a measuring device 434b of a flux density measuring unit 434a of the magnetic moment measuring unit 434, and the rail 436 that forms the pathway for the drive system 435.

The magnetic moment measuring unit 434 measures the magnetic moment of the magnet 227 by measuring the residual flux density of the magnet 227 inside the capsule medical device 202. The magnetic moment measuring unit 434 includes the flux density measuring unit 434a that measures the residual flux density of the magnet 227 and the magnetic moment calculating unit 213b.

The flux density measuring unit 434a includes the independent measuring device 434b, and uses the measuring device 434b to measure the residual flux density of the magnet 227 inside the capsule medical device 202. More specifically, the measuring device 434b is radio-connected or wire-connected to the flux density measuring unit 434a in a communicable manner, and is mounted on the drive system 435. The measuring device 434b sequentially measures flux densities of the magnet 227 inside the capsule medical device 202, while being rotatively moved around the housing unit 432 by the drive system 435, with the capsule medical device 202 being the center of the rotational movement. With the use of the measuring device 434b, the flux density measuring unit 434a sequentially measures the magnetic flux densities of the magnet 227 at various positions around the housing unit 432. The flux density measuring unit 434a obtains the largest value of the flux densities of the magnet 227 measured at the various positions around the housing unit 432, and regards the largest value as the value of the residual flux density of the magnet 227. The flux density measuring unit 434a then transmits the result of the measurement of the residual flux density of the magnet 227 measured in the above manner to the magnetic moment calculating unit 213b. The value of the residual flux density of the magnet 227 measured by the flux density measuring unit 434a is used by the magnetic moment calculating unit 213b to calculate the magnetic moment of the magnet 227 as described above.

The drive system 435 and the rail 436 are designed for rotatively move the measuring device 434b of the flux density measuring unit 434a around the capsule medical device 202 to be checked. More specifically, the drive system 435 may be embodied with the use of wheels and an actuator, and the measuring device 434b of the flux density measuring unit 434a is fixed onto the drive system 435. The rail 436 forms the pathway for the drive system 435, and is placed along a circle formed around the central axis CL1 of the package 203 housed in the housing unit 432 (desirably, around the central axis CL2 of the capsule medical device 202 inside the package 203). The drive system 435 travels on the rail 436, so as to rotatively move the measuring device 434b around the housing unit 432, with the capsule medical device 202 (the magnet 227, to be more specific) being the center of the rotational movement.

The actuator of the drive system 435 may be a drive motor including an electromagnet or the like, but it is desirable that the actuator of the drive system 435 is a nonmagnetic actuator such as an ultrasonic motor or an artificial muscle actuator, so as to achieve higher precision in the flux density measurement by the measuring device 434b.

The control unit 437 controls the magnetic moment measuring unit 434 and the drive system 435 to measure the magnetic moment of the magnet 227. In this case, the control unit 437 controls the drive system 435 to rotatively move along the rail 436 and around the housing unit 432 at least once. The control unit 437 also controls the flux density measuring unit 434a to sequentially measure flux densities of the magnet 227 at various positions around the housing unit 432 with the use of the measuring device 434b. The control unit 437 also recognizes the moving distance of the drive system 435 on the rail 436. The control unit 437 then controls the flux density measuring unit 434a to select the residual flux density having the value equivalent to the largest value among the results of the measurement carried out by the measuring device 434b (or the values of the flux densities of the magnet 227 measured at various positions around the housing unit 432) when the drive system 435 finishes moving around the housing unit 432 at least once. By controlling the magnetic moment measuring unit 434 and the drive system 435 in this manner, the control unit 437 obtains the magnetic moment of the magnet 227 inside the capsule medical device 202. Except for the functions to control the flux density measuring unit 434a and the drive system 435, the control unit 437 has the same functions as those of the control unit 211 of the checking device 201 in accordance with the sixth embodiment.

Figure 23:
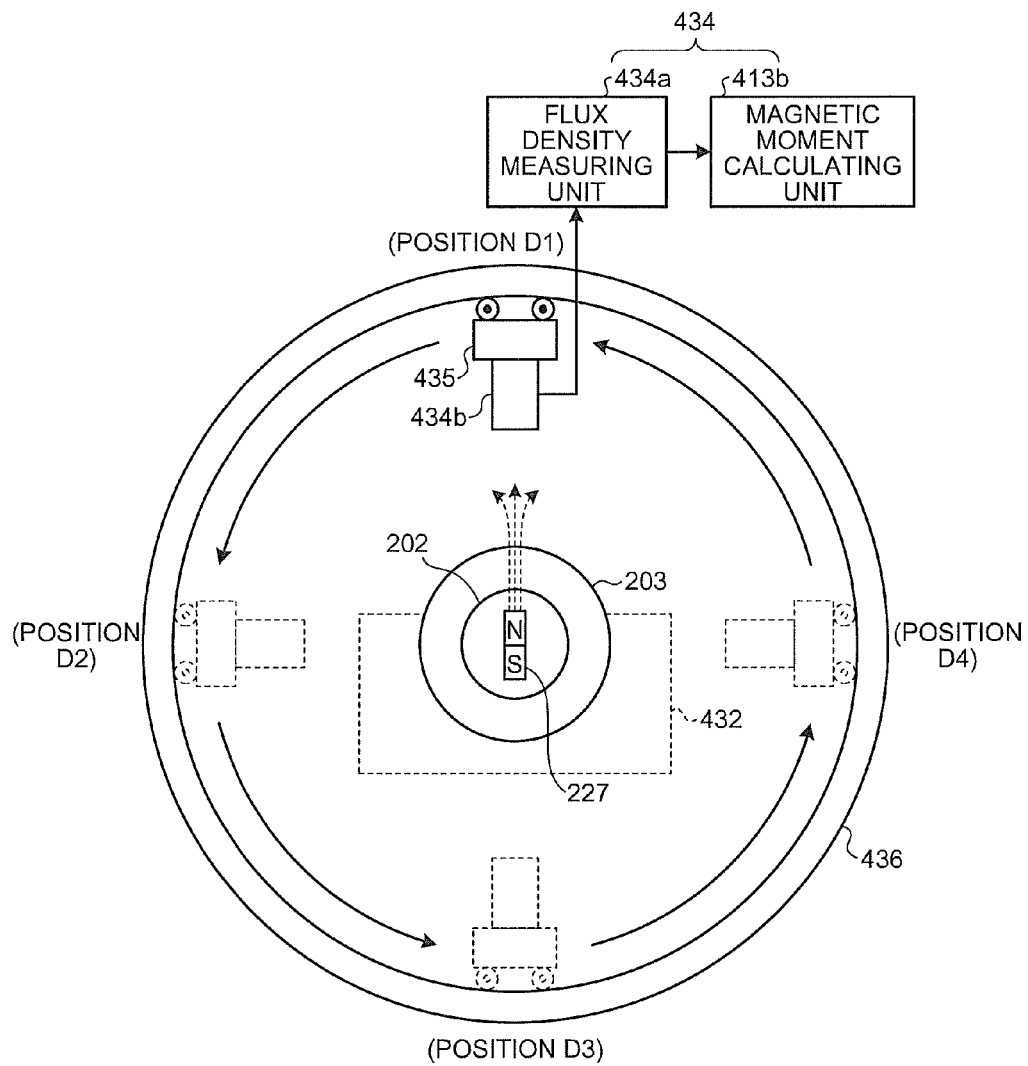
FIG. 23 is a schematic view showing an example case where the magnetic moment of a magnet inside a capsule medical device is measured by the checking device in accordance with the seventh embodiment of the present invention.

Next, the operation of the checking device 431 in accordance with the seventh embodiment of the present invention will be described. FIG. 23 is a schematic view showing an example case where the checking device in accordance with the seventh embodiment of the present invention measures the magnetic moment of the magnet inside the capsule medical device. Referring now to FIG. 23, the operation by the checking device 431 to measure the magnetic moment of the magnet 227 inside the capsule medical device 202 will be described in detail.

As described above, the capsule medical device 202 to be checked is housed in the concave portion of the housing unit 432, while accommodated in the package 203 (see FIG. 22). In this case, the housing unit 432 secures and supports the capsule medical device 202 via the package 203.

Under the control of the control unit 437, the drive system 435 travels on the rail 436, and moves around the housing unit 432 at least once, with the capsule medical device 202 being the center of the rotational movement. The measuring device 434b sequentially measures flux densities of the magnet 227 at various positions around the housing unit 432 at predetermined time intervals, while being moved around the housing unit 432 at least once by the drive system 435, with the magnet 227 inside the capsule medical device 202 being the center of the rotational movement. In this case, the measuring device 434b rotatively moves in a circle having a radial direction that is coincident with the magnetization direction of the magnet 227. As shown in FIG. 23, the measuring unit 434b sequentially passes through positions D1 through D4 located around the housing unit 432, and sequentially measures the flux densities of the magnet 227 at the positions D1 through D4, for example.

Here, the flux densities of the magnet 227 around the housing unit 432 vary at the positions, and the magnet 227 has the highest flux density at the position located in the magnetization direction of the magnet 227 (the position D1 in FIG. 23). In the magnetic moment measuring unit 434, the flux density measuring unit 434a obtains the flux densities sequentially measured at the respective positions D1 through D4 by the measuring device 434b, and selects the flux density measured at the position D1, which has the largest value among those measured flux densities. In this manner, the flux density measuring unit 434a regards the flux density at the position D1 as the residual flux density of the magnet 227. The flux density measuring unit 434a then transmits the value of the residual flux density to the magnetic moment calculating unit 213b. As in the sixth embodiment, the magnetic moment calculating unit 213b multiplies the volume of the magnet 227 according to the magnet volume information 210a by the value of the residual flux density measured by the flux density measuring unit 434a, so as to calculate the magnetic moment of the magnet 227. After that, the value of the magnetic moment of the magnet 227 measured by the magnetic moment measuring unit 434 is transmitted to the control unit 437.

The flux density measuring unit 434a may either intermittently or continuously measure the flux densities of the magnet 227 at various positions around the housing unit 432 with the use of the measuring device 434b. In other words, the measuring device 434b may sequentially measure flux densities at the various positions (the positions D1, D2, D3, and D4 shown in FIG. 23, for example) around the housing unit 432 every time a predetermined period of times has passed or every time the drive system 435 has traveled a predetermined distance, while rotatively moving around the housing unit 432. Alternatively, the measuring device 434b may continuously measure flux densities over the entire circle surrounding the housing unit 432.

As described above, in the seventh embodiment of the present invention, the housing unit secures and supports the capsule medical device to be checked via the package. The measuring device of the flux density measuring unit sequentially measures the flux densities of the magnet inside the capsule medical device at various positions around the housing unit, while being rotatively moved by the drive system around the housing unit, with the capsule medical device being the center of the rotational movement. The flux density measuring unit selects the largest value among the flux densities measured by the measuring device, and regards the largest value as the residual flux density of the magnet. The other configurations of this embodiment are the same as those of the sixth embodiment. Accordingly, the residual flux density of the magnet can be measured, even though the magnetization direction of the magnet inside the capsule medical device to be checked is not controlled by a magnetic field. As a result, the same effects as those of the sixth embodiment can be achieved, and a checking device that consumes less electric power can be easily realized.

Next, an eighth embodiment of the present invention will be described. In the above described sixth and seventh embodiments, the magnetic moment of the magnet 227 is measured as the characteristics of the magnet 227 inside the capsule medical device 202. In the eighth embodiment, on the other hand, the relative angle difference between the reference direction of the image capturing unit 222 (the vertical direction of the light receiving face, for example) and the magnetization direction of the magnet 227 inside the capsule medical device 202 is also measured as the characteristics of the magnet 227.

Figure 24:
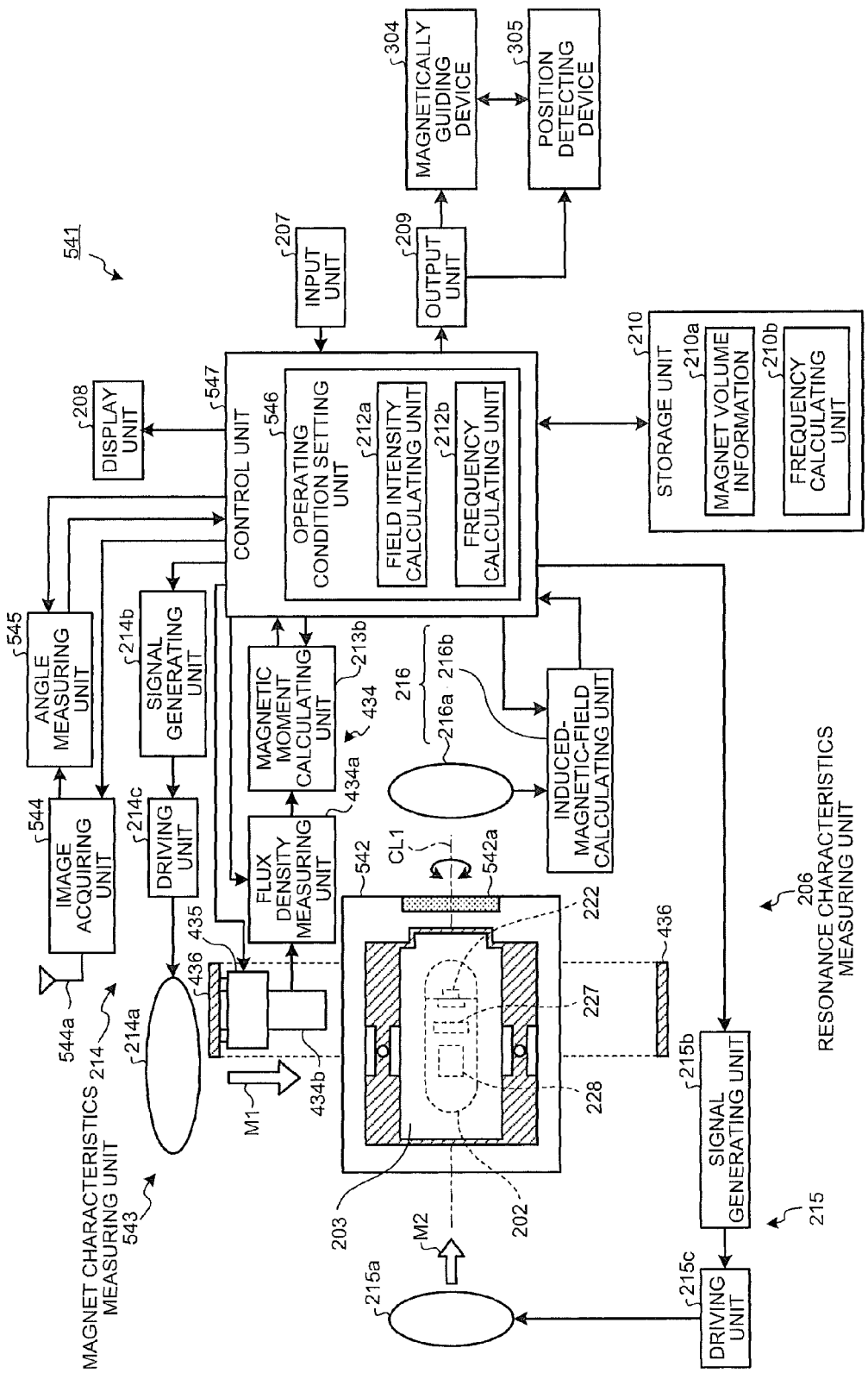
FIG. 24 is a block diagram schematically showing an example structure of a checking device in accordance with an eighth embodiment of the present invention.

FIG. 24 is a block diagram schematically showing an example structure of a checking device in accordance with the eighth embodiment of the present invention. As shown in FIG. 24, the checking device 541 in accordance with the eighth embodiment is the same as the checking device 201 of the sixth embodiment, except that the housing unit 204 is replaced with a housing unit 542, the magnet characteristics measuring unit 205 is replaced with a magnet characteristics measuring unit 543, and the control unit 211 is replaced with a control unit 547. A magnetically guiding system in accordance with the eighth embodiment of the present invention is the same as the magnetically guiding system 301 of the sixth embodiment (see FIG. 20), except that the checking device 201 is replaced with the checking device 541. The other configurations of this embodiment are the same as those of the sixth embodiment, and the same components as those of the sixth embodiment are denoted by the same reference numerals as those used in the sixth embodiment.

The housing unit 542 has the same structure and functions as those of the housing unit 204 of the checking device 201 of the sixth embodiment, except for an image member 542a. The image member 542a is a plate-like or sheet-like member on which an image having an orientation is drawn. As shown in FIG. 24, the image member 542a is fixed in the housing unit 542 in such a manner as to be in the image viewing field of the image capturing unit 222 inside the capsule medical device 202. The image drawn on the image member 542a is a pattern with which the reference direction such as the vertical direction of the drawn image can be easily defined. For example, the image may be a striped pattern as shown in FIG. 25.

Figure 25:
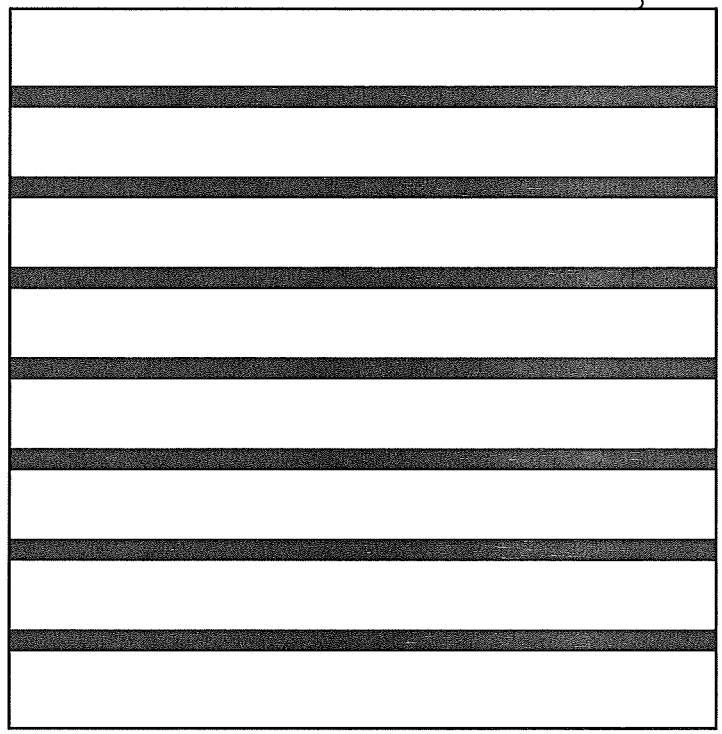
FIG. 25 is a schematic view showing an example of an image drawn on an image member.

The striped pattern shown in FIG. 25 is merely an example of the image drawn on the image member 542a. The image drawn on the image member 542a may be any pattern other than a striped pattern, may be a symbol, a numeric character, or a character, or may be a combination of those symbols and characters, as long as the reference direction such as the vertical direction of the image can be easily detected.

The magnet characteristics measuring unit 543 measures the magnetic moment of the magnet 227, and the relative angle difference between the reference direction of the image capturing unit 222 and the magnetization direction of the magnet 227 inside the capsule medical device 202. The magnet characteristics measuring unit 543 regards the magnetic moment and the relative angle difference as the characteristics of the magnet 227 provided inside the capsule medical device 202. More specifically, the magnet characteristics measuring unit 543 measures the characteristics of the magnet 227 inside the capsule medical device 202 that is rotatably supported by the housing unit 542 via the package 203. As shown in FIG. 24, the magnet characteristics measuring unit 543 includes the magnetization direction control unit 214 described in the sixth embodiment, and the magnetic moment measuring unit 434, the drive system 435, and the rail 436 described in the seventh embodiment. The magnet characteristics measuring unit 543 further includes an image acquiring unit 544 that acquires each image captured by the image capturing unit 222, and an angle measuring unit 545 that measures the angle between the reference direction of the image capturing unit 222 and the magnetization direction of the magnet 227.

The image acquiring unit 544 has a receiving antenna 544a, and exchanges image data with the capsule medical device 202 via the receiving antenna 544a. More specifically, the image acquiring unit 544 receives images (images of the image member 542a) captured by the image capturing unit 222 of the capsule medical device 202 inside the package 203 housed in the housing unit 542, via the receiving antenna 544a. Under the control of the control unit 547, the image acquiring unit 544 acquires an image of the image member 542a captured by the image capturing unit 222 when the reference direction of the image capturing unit 222 is coincident with the reference direction of the image member 542a (the image captured here will be hereinafter referred to as the reference image). The image acquiring unit 544 also acquires an image of the image member 542a captured by the image capturing unit 222 when the reference direction of the image member 542a is coincident with the magnetization direction of the magnet 227 (the image captured here will be hereinafter referred to as the comparative image). The image acquiring unit 544 transmits the reference image and the comparative image obtained from the capsule medical device 202 to the angle measuring unit 545.

Under the control of the control unit 547, the angle measuring unit 545 measures the angle between the reference direction of the image capturing unit 222 and the magnetization direction of the magnet 227, based on the reference image and the comparative image received from the image acquiring unit 544. Here, the reference direction of the image capturing unit 222 is the vertical direction of the light receiving face of the solid-state image sensor 222b (see FIG. 19), for example. In this case, the vertical direction of the image captured by the image capturing unit 222 is defined by the reference direction of the image capturing unit 222. The angle between the reference direction of the image capturing unit 222 and the magnetization direction of the magnet 227 represents the relative angle difference between the reference direction of the image capturing unit 222 and the magnetization direction of the magnet 227, and is regarded as one aspect of the characteristics of the magnet 227. The angle measuring unit 545 transmits the result of the measurement of the angle formed between the reference direction of the image capturing unit 222 and the magnetization direction of the magnet 227, to the control unit 547.

In the magnet characteristics measuring unit 543, the magnetization direction control unit 214 includes the magnetic field generating coil 214a, the signal generating unit 214b, and the driving unit 214c, as described above. The magnetization direction control unit 214 applies the guiding magnetic field M1 to the magnet 227 inside the capsule medical device 202, so as to relatively change the magnetization direction of the magnet 227 with respect to the housing unit 542, as described above. By doing so, the magnetization direction control unit 214 controls the magnetization direction of the magnet 227 to shift in a desired direction.

As in the above described seventh embodiment, the drive system 435 travels on the rail 436, with the measuring device 434b being mounted thereon. The drive system 435 rotatively moves around the housing unit 542, with the capsule medical device 202 being the center of the rotational movement. The flux density measuring unit 434a sequentially measures flux densities of the magnet 227 at various positions around the housing unit 542 with the use of the measuring device 434b. The flux density measuring unit 434a then selects the largest value among the measured flux densities, and regards the largest value as the value of the residual flux density of the magnet 227. Using the measurement value of the residual flux density, the magnetic moment calculating unit 213b calculates the magnetic moment of the magnet 227, and transmits the value of the calculated magnetic moment to the control unit 547.

The flux density measuring unit 434a may directly measure the residual flux density of the magnet 227 with the use of the measuring device 434b located in the magnetization direction of the magnet 227, instead of sequentially measuring the flux densities of the magnet 227 at various positions around the housing unit 542. In such a case, the drive system 435 travels on the rail 436, and moves the measuring device 434b to a position situated in the magnetization direction of the magnet 227, under the control of the control unit 547. The flux density measuring unit 434a sets the measurement value of the flux density obtained with the use of the measuring device 434b located in the magnetization direction of the magnet 227, as the measurement value of the residual flux density of the magnet 227, under the control of the control unit 547.

The control unit 547 controls the guiding magnetic field M1 of the magnetization direction control unit 214, so that the reference direction of the image capturing unit 222 is coincident with the reference direction of the image member 542a. In this case, the control unit 547 obtains the image data (the images of the image member 542a captured by the image capturing unit 222) from the image acquiring unit 544 via the angle measuring unit 545, and compares the obtained image data with preset reference image data. The control unit 547 controls the field intensity or the magnetization direction of the guiding magnetic field M1, so that the obtained image data is coincident with the reference image data. By doing so, the control unit 547 causes the reference direction of the image capturing unit 222 and the reference direction of the image member 542a to be coincident with each other. With the reference direction of the image member 542a being set in advance, the control unit 547 controls the field intensity or the magnetization direction of the guiding magnetic field M1, so that the reference direction of the image member 542a is coincident with the magnetization direction of the magnet 227.

The control unit 547 also controls the image acquiring unit 544 to sequentially acquire the images captured by the image capturing unit 222 from the capsule medical device 202 via the receiving antenna 544a. The control unit 547 then controls the angle measuring unit 545 to measure (calculate) the angle formed between the reference direction of the image capturing unit 222 and the magnetization direction of the magnet 227, based on the reference image and the comparative image acquired by the image acquiring unit 544. By controlling the image acquiring unit 544 and the angle measuring unit 545 in this manner, the control unit 547 obtains the measurement value of the angle formed between the reference direction of the image capturing unit 222 and the magnetization direction of the magnet 227, or the measurement value of the relative angle difference between the reference direction of the image capturing unit 222 and the magnetization direction of the magnet 227.

The control unit 547 further controls the magnetic moment measuring unit 434 and the drive system 435 to measure the magnetic moment of the magnet 227. In this case, the control unit 547 may control the magnetic moment measuring unit 434 and the drive system 435, like the control unit 437 of the checking device 431 in the seventh embodiment, or may control the drive system 435 to move the measuring device 434b to a position situated in the magnetization direction of the magnet 227. The control unit 547 may also control the flux density measuring unit 434a to measure the residual flux density of the magnet 227 with the use of the measuring unit 434b located in the magnetization direction of the magnet 227.

The control unit 547 also includes an operating condition setting unit 546 in place of the operating condition setting unit 212 of the checking device 201 of the sixth embodiment. The operating condition setting unit 546 obtains the result of the measurement carried out by the angle measuring unit 545. Based on the measurement result (to be more specific, the measurement value of the angle formed between the reference direction of the image capturing unit 222 and the magnetization direction of the magnet 227), the operating condition setting unit 546 sets a condition for correcting the magnetization direction of the magnetically guiding device 304. The condition for correcting the magnetization direction is the operating condition for correcting the relative angle difference between the reference direction of the image capturing unit 222 and the magnetization direction of the magnet 227 inside the capsule medical device 202 to be magnetically guided by the magnetically guiding device 304. The control unit 547 controls the display unit 208 to display the magnetization direction correcting condition set by the operating condition setting unit 546 as one of the operating conditions set for the magnetically guiding device 304. The control unit 547 also controls the output unit 209 to output the magnetization direction correcting condition to the magnetically guiding device 304.

Upon receipt of the magnetization direction correcting condition, the magnetic-guiding control unit 304d (see FIG. 20) of the magnetically guiding device 304 corrects the angle difference between the reference direction of the image capturing unit 222 and the magnetization direction of the magnet 227 inside the capsule medical device 202 introduced into the body of a test subject, or the angle difference between the reference direction (the vertical direction of the screen, for example) of an in-vivo image of the test subject captured by the image capturing unit 222 and the magnetization direction of the magnet 227. By doing so, the magnetic-guiding control unit 304d also controls the magnetic guiding of the capsule medical device 202 inside the body of the test subject. In this manner, the magnetic-guiding control unit 304d can cause the vertical and horizontal directions of the in-vivo image shown on the screen to be coincident with the vertical and horizontal directions of the magnetic guiding of the capsule medical device 202.

Except for the function to control the magnet characteristics measuring unit 543, the control unit 547 has the same control functions as those of the control unit 211 of the checking device 201 of the sixth embodiment. Also, the operating condition setting unit 546 includes the field intensity calculating unit 212a and the frequency calculating unit 212b, and sets the field intensity condition for the magnetically guiding device 304 and the frequency condition for the position detecting device 305, like the operating condition setting unit 212 in the sixth and seventh embodiments.

Next, the operation of the checking device 541 in accordance with the eighth embodiment of the present invention will be described. FIG. 26 is a schematic view illustrating the operation by the checking device of the eighth embodiment of the present invention to measure the angle formed between the reference direction of the magnet and the reference direction of the image capturing unit inside the capsule medical device. Referring now to FIG. 26, the operation by the checking device 541 to measure the angle θ formed between the reference direction F1 of the image capturing unit 222 and the magnetization direction F2 of the magnet 227 inside the capsule medical device 202 will be described in detail, with an example case where the reference direction of the image member 542a is the vertical direction of the image drawn thereon.

The capsule medical device 202 inside the package 203 housed in the housing unit 542 as shown in FIG. 24 is switched on and off by a magnetic field or an optical signal applied from a predetermined external device. The capsule medical device 202 captures images of the image member 542a with the use of the image capturing unit 222. Every time an image is captured, the capsule medical device 202 radio-transmits the image to the outside via the transmission unit 224 (see FIG. 19).

In this situation, the control unit 547 of the checking device 541 controls the image acquiring unit 544 and the angle measuring unit 545, to sequentially acquire images of the image member 542a captured by the image capturing unit 222. The control unit 547 controls the guiding magnetic field M1 of the magnetization direction control unit 214, so that the obtained image data is coincident with the reference image data. In this case, the magnetization direction control unit 214 applies the guiding magnetic field M1 to the magnet 227 inside the capsule medical device 202, so that the reference direction of the image capturing unit 222 is coincident with the reference direction (the vertical direction) of the image member 542a. With the reference direction F1 being coincident with the reference direction of the image member 542a, the image capturing unit 222 captures an image of the image member 542a (the reference image P1). The image capturing unit 544 then acquires the reference image P1 captured by the image capturing unit 222 from the capsule medical device 202 via the receiving antenna 544a, and transmits the reference image P1 to the angle measuring unit 545. The vertical direction of the reference image P1 is coincident with the reference direction F1 of the image capturing unit 222, as shown in FIG. 26.

The control unit 547 then controls the guiding magnetic field M1 of the magnetization direction control unit 214, so that the magnetization direction F2 of the magnet 227 is coincident with the reference direction of the image member 542a. In this case, the magnetization direction control unit 214 applies the guiding magnetic field M1 to the magnet 227 inside the capsule medical device 202, so that the magnetization direction F2 of the magnet 227 is coincident with the reference direction of the image member 542a. If the reference direction F1 of the image capturing unit 222 has a rotational displacement relative to the magnetization direction F2 of the magnet 227, the image capturing unit 222 captures an image of the image member 542a (the comparative image P2), with the magnetization direction F2 of the magnet 227 being coincident with the reference direction of the image member 542a, or with the image capturing unit 222 tilting (rotating) at the angle θ with respect to the reference direction of the image member 542a. The image acquiring unit 544 acquires the comparative image P2 captured by the image capturing unit 222 from the capsule medical device 202 via the receiving antenna 544a, and transmits the obtained comparative image P2 to the angle measuring unit 545. Here, the vertical direction of the comparative image P2 is coincident with the magnetization direction F2 of the magnet 227, as shown in FIG. 26.

Based on the reference image P1 and the comparative image P2 obtained from the image acquiring unit 544 as described above, the angle measuring unit 545 measures the angle θ between the reference direction F1 of the image capturing unit 222 and the magnetization direction F2 of the magnet 227. More specifically, the angle measuring unit 545 calculates the angle between the striped pattern of the reference image P1 and that of the comparative image P2. If the reference image P1 and the comparative image P2 are superimposed on each other, the striped pattern of the comparative image P2 is tilted relative to the striped pattern of the reference image P1 indicated by the diagonal lines in FIG. 26. The angle between the reference image P1 and the comparative image P2 is the angle θ between the reference direction F1 of the image capturing unit 222 and the magnetization direction F2 of the magnet 227. By calculating the angle between the reference image P1 and the comparative image P2, the angle measuring unit 545 measures the angle θ between the reference direction F1 of the image capturing unit 222 and the magnetization direction F2 of the magnet 227. The angle measuring unit 545 then transmits the measurement value of the angle θ to the control unit 547.

The control unit 547 obtains the result (the angle θ) of the measurement carried out by the angle measuring unit 545, as the relative angle difference between the reference direction F1 of the image capturing unit 222 and the magnetization direction F2 of the magnet 227. Based on the angle θ as the result of the measurement carried out by the angle measuring unit 545, the operating condition setting unit 546 sets the magnetization direction correcting condition for the magnetically guiding device 304, as described above. The control unit 547 obtains the magnetic moment calculated by the magnetic moment calculating unit 213b using the value obtained by the flux density measuring unit 434a when the measuring device 434b is located in the magnetization direction F2 of the magnet 227. The control unit 547 regards the obtained magnetic moment as the measured magnetic moment of the magnet 227.

As described above, in the eighth embodiment of the present invention, the image member on which an image having an orientation is drawn is placed and fixed in the housing unit that rotatably houses the capsule medical device to be checked. The image acquiring unit acquires the reference image that is the image of the image member captured by the image capturing unit when the reference direction of the image capturing unit inside the capsule medical device is coincident with the reference direction of the image member, and the comparative image that is the image of the image member captured by the image capturing unit when the reference direction of the image member is coincident with the magnetization direction of the magnet inside the capsule medical device. Based on the reference image and the comparative image, the angle between the reference direction of the image capturing unit and the magnetization direction of the magnet is measured. When the measuring device is moved to a position situated in the magnetization direction of the magnet by the drive system, the residual flux density of the magnet is measured. The other configurations of this embodiment are the same as those of the sixth embodiment. Accordingly, the relative angle difference between the reference direction of the image capturing unit and the magnetization direction of the magnet inside the capsule medical device, as well as the magnetic moment of the magnet, can be measured. As a result, it is possible to not only achieve the same effects as those of the sixth embodiment, but also form a checking device that can check the relative angle difference between the vertical direction of each image captured by the image capturing unit and the magnetization direction of the magnet inside the capsule medical device.

With the use of the checking device in accordance with the eighth embodiment, a user can check the display information shown on the display unit, so as to recognize the magnetization direction correcting condition required for the magnetically guiding device to correct the relative angle difference between the reference direction of the image capturing unit and the magnetization direction of the magnet when the capsule medical device is magnetically guided. Accordingly, the user can set the magnetization direction correcting condition for the magnetically guiding device in the initial stage. As a result, the magnetically guiding device can magnetically guide the capsule medical device inside the body of a test subject accurately in response to an operation instruction, while correcting the angle difference between the magnetization direction of the magnet and the reference direction (the vertical direction of the screen, for example) of each in-vivo image of the test subject captured by the image capturing unit inside the capsule medical device introduced into the body of the test subject.

Also, as the output unit transmits the magnetization direction correcting condition to the magnetically guiding device, the initial magnetization direction correcting condition can be easily set for the magnetically guiding device to magnetically guide the capsule medical device inside the body of the test subject. As a result, a magnetically guiding system that can be more easily operated to magnetically guide the capsule medical device inside the body of a test subject can be readily realized.

Next, a ninth embodiment of the present invention will be described. In the above described eighth embodiment, the relative angle difference between the reference direction of the image capturing unit 222 and the magnetization direction of the magnet 227 is measured based on the reference image and the comparative image captured by the image capturing unit 222 inside the capsule medical device 202. In the ninth embodiment, on the other hand, the angle between the magnetization direction of the magnet 227 and the reference direction of the image member 542a observed when the image capturing unit 222 captures the reference image is measured as the relative angle difference between the reference direction of the image capturing unit 222 and the magnetization direction of the magnet 227.

Figure 27:
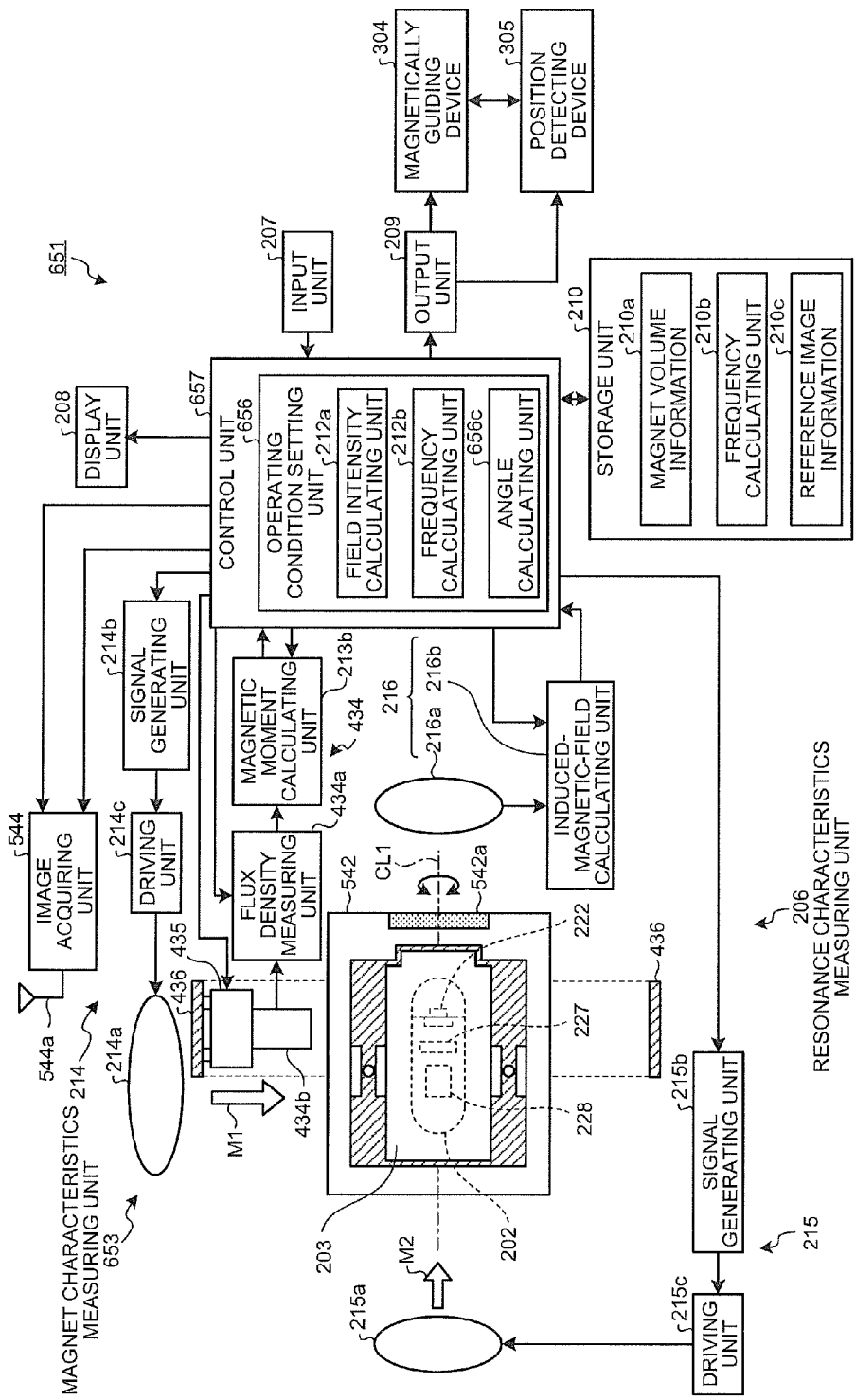
FIG. 27 is a block diagram schematically showing an example structure of a checking device in accordance with a ninth embodiment of the present invention.

FIG. 27 is a block diagram schematically showing an example structure of a checking device in accordance with the ninth embodiment of the present invention. As shown in FIG. 27, the checking device 651 in accordance with the ninth embodiment is the same as the checking device 541 of the eighth embodiment, except the magnet characteristics measuring unit 543 is replaced with a magnet characteristics measuring unit 653, and the control unit 547 is replaced with a control unit 657. In this checking device 651, the magnet characteristics measuring unit 653 does not include the angle measuring unit 545. Under the control of the control unit 657, the image capturing unit 544 acquires image data captured by the image capturing unit 222 from the capsule medical device 202. Every time image data is acquired, the image acquiring unit 544 transmits the acquired image data to the control unit 657. The storage unit 210 further stores reference image information 210c that is the data about the reference image obtained when the image capturing unit 222 captures an image of the image member 542a, with the reference direction (the vertical direction, for example) of the image member 542a being coincident with the reference direction of the image capturing unit 222. A magnetically guiding system in accordance with the ninth embodiment is the same as the magnetically guiding system of the eighth embodiment, except that the checking device 541 is replaced with the checking device 651. The other configurations of this embodiment are the same as those of the eighth embodiment, and the same components as those of the eighth embodiment are denoted by the same reference numerals as those used in the eighth embodiment.

The magnet characteristics measuring unit 653 does not include the angle measuring unit 545, and measures the magnetic moment of the magnet 227 as the characteristics of the magnet 227 inside the capsule medical device 202. The image acquiring unit 544 acquires the image data captured by the image capturing unit 222 inside the capsule medical device 202. In this case, the image acquiring unit 544 acquires the image data captured by the image capturing unit 222 from the capsule medical device 202, under the control of the control unit 657, as described above. Every time image data is acquired, the image acquiring unit 544 transmits the image data to the control unit 657. Except for this function, the magnet characteristics measuring unit 653 has the same functions as those of the magnet characteristics measuring unit 543 of the checking device 541 of the eighth embodiment.

The control unit 657 controls the image acquiring unit 544 to acquire the image data captured by the image capturing unit 222 from the capsule medical device 202. By doing so, the control unit 657 sequentially obtains the image data captured by the image capturing unit 222 via the image acquiring unit 544. The control unit 657 reads the reference image information 210c from the storage unit 210, and controls the guiding magnetic field M1 of the magnetization direction control unit 214, so that the reference image information 210c is coincident with the image data obtained from the image acquiring unit 544 (the data about the image captured by the image capturing unit 222). In this case, the control unit 657 controls the field intensity or the magnetization direction of the guiding magnetic field M1, so that the reference image information 210c is coincident with the obtained image data. By doing so, the control unit 657 causes the reference direction of the image capturing unit 222 to match the reference direction of the image member 542a.

The control unit 657 includes an operating condition setting unit 656 in place of the operating condition setting unit 546 of the checking device 541 of the eighth embodiment. The operating condition setting unit 656 includes the field intensity calculating unit 212a and the frequency calculating unit 212b, and further includes an angle calculating unit 656c. With the reference direction of the image member 542a being set in advance, the angle calculating unit 656c calculates the angle between the magnetization direction of the magnet 227 and the reference direction of the image member 542a observed when the image capturing unit 222 captures an image that is coincident with the reference image information 210c or captures the reference image. In a state where the image capturing unit 222 captures the reference image of the image member 542a, the reference direction of the image capturing unit 222 is coincident with the reference direction (the vertical direction, for example) of the image member 542a. More specifically, the angle calculated by the angle calculating unit 656c is the angle between the reference direction of the image capturing unit 222 and the magnetization direction of the magnet 227, and represents the relative angle difference between the reference direction of the image capturing unit 222 and the magnetization direction of the magnet 227. The operating condition setting unit 656 sets the magnetization direction correcting condition for the magnetically guiding device 304, based on the result of the calculation performed by the angle calculating unit 656c (or based on the angle between the reference direction of the image capturing unit 222 and the magnetization direction of the magnet 227).

Except for the function to control the image acquiring unit 544, the control unit 657 has the same functions as those of the control unit 547 of the checking device 541 of the eighth embodiment. Except for the function to calculate the relative angle difference between the reference direction of the image capturing unit 222 and the magnetization direction of the magnet 227, the operating condition setting unit 656 has the same functions as those of the operating condition setting unit 546 of the checking device 541 of the eighth embodiment.

Figure 28:
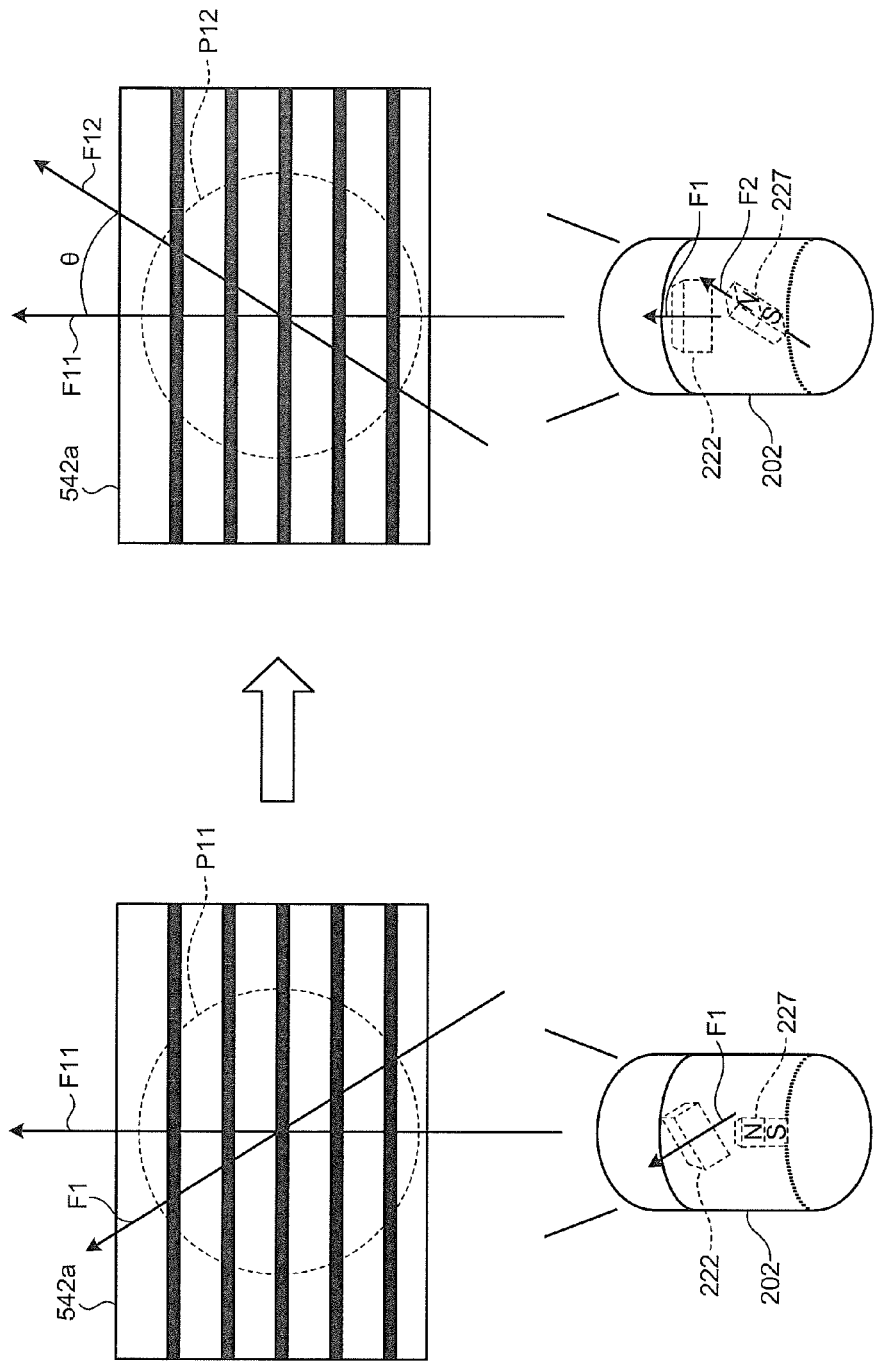
FIG. 28 is a schematic view illustrating an operation by the checking device in accordance with the ninth embodiment of the present invention to calculate the angle between the reference direction of a magnet provided in a capsule medical device and the reference direction of an image capturing unit.

Next, the operation of the checking device 651 in accordance with the ninth embodiment of the present invention will be described. FIG. 28 is a schematic view illustrating the operation by the checking device of the ninth embodiment of the present invention to calculate the angle between the reference direction of the magnet and the reference direction of the image capturing unit inside the capsule medical device. Referring now to FIG. 28, the operation by the checking device 651 to measure the angle θ formed between the reference direction F1 of the image capturing unit 222 and the magnetization direction F2 of the magnet 227 inside the capsule medical device 202 will be described in detail, with taking a case where the reference direction of the image member 542*a* is the vertical direction of the image drawn thereon as an example.

The capsule medical device 202 inside the package 203 housed in the housing unit 542 as shown in FIG. 27 is switched on and off by a magnetic field or an optical signal applied from a predetermined external device. The capsule medical device 202 captures images of the image member 542*a* with the use of the image capturing unit 222. Every time an image is acquired, the capsule medical device 202 radiotransmits the image to the outside via the transmission unit 224 (see FIG. 19).

In this situation, the control unit 657 of the checking device 651 controls the image acquiring unit 544, to sequentially acquire images of the image member 542*a* captured by the image capturing unit 222. The control unit 657 reads the reference image information 210*c* from the storage unit 210, and compares the read reference image information 210*c* with the images obtained from the image acquiring unit 544 (the images of the image member 542*a* captured by the image capturing unit 222).

If the reference direction F1 of the image capturing unit 222 is tilted relative to the reference direction F11 (the vertical direction) of the image member 542*a* as shown in FIG. 28, the image capturing unit 222 captures an image P11 (hereinafter referred to as the rotated image) of the image member 542*a*, with its reference direction being rotated with respect to the reference direction F11 of the image member 542*a*. The control unit 657 obtains the rotated image P11 captured by the image capturing unit 222 via the image acquiring unit 544, and compares the rotated image P11 with the reference image information 210*c*. Since the rotated image P11 is not coincident with the reference image information 210*c*, the control unit 657 controls the field intensity or the magnetization direction of the guiding magnetic field M1, based on the relative angle difference between the rotated image P11 and the reference image information 210*c*. By doing so, the control unit 657 causes the reference direction F1 of the image capturing unit 222 to be coincident with the reference direction F11 of the image member 542*a*.

When the reference direction F1 of the image capturing unit 222 is coincident with the reference direction F11 of the image member 542*a* (see FIG. 28), the image capturing unit 222 captures an image that is coincident with the reference image information 210*c*, or captures a reference image P12 of the image member 542*a*. In this situation, the control unit 657 of the checking device 651 obtains the reference image P12 captured by the image capturing unit 222 via the image capturing unit 544, and compares the obtained reference image P12 with the reference image information 210*c*. Since the reference image P12 is coincident with the reference image information 210*c*, the control unit 657 obtains the magnetization direction F2 of the magnet 227 observed when the image capturing unit 222 captures the reference image P12, based on the control information about the guiding magnetic field M1 observed at the same time.

In the checking device 651, the angle calculating unit 656*c* calculates the angle θ between the magnetization direction F2 of the magnet 227 and the reference direction F11 of the image member 542*a* observed when the image capturing unit 222 captures the reference image P12. The angle calculating unit 656*c* calculates the angle θ as the angle between the reference direction F1 of the image capturing unit 222 and the magnetization direction F2 of the magnet 227 (or the relative angle difference between the reference direction F1 and the magnetization direction F2). As described above, the operating condition setting unit 656 sets the magnetization direction correcting condition for the magnetically guiding device 304, based on the angle θ, which is the result of the calculation performed by the angle calculating unit 656*c*.

As described above, in the ninth embodiment of the present invention, the magnetization direction of the magnet inside the capsule medical device is controlled, so that the image data obtained by capturing an image of the image member by the image capturing unit inside the capsule medical device is coincident with the reference image information. The angle between the magnetization direction of the magnet and the reference direction of the image member observed when the image capturing unit captures the reference image is calculated as the relative angle difference between the reference direction of the image capturing unit and the magnetization direction of the magnet. The other configurations of this embodiment are the same as those of the eighth embodiment. Accordingly, a checking device that can achieve the same effects as those of the eighth embodiment can be realized with a simple device structure.

Next, a tenth embodiment of the present invention will be described. In the above described sixth embodiment, the magnetic moment of the magnet 227 is calculated with the use of the residual flux density of the magnet 227 inside the capsule medical device 202. In the tenth embodiment, on the other hand, the magnetic torque that is generated when a magnetic field is applied to the capsule medical device 202 is measured, and the magnetic moment of the magnet 227 is measured based on the result of the magnetic torque measurement.

Figure 29:
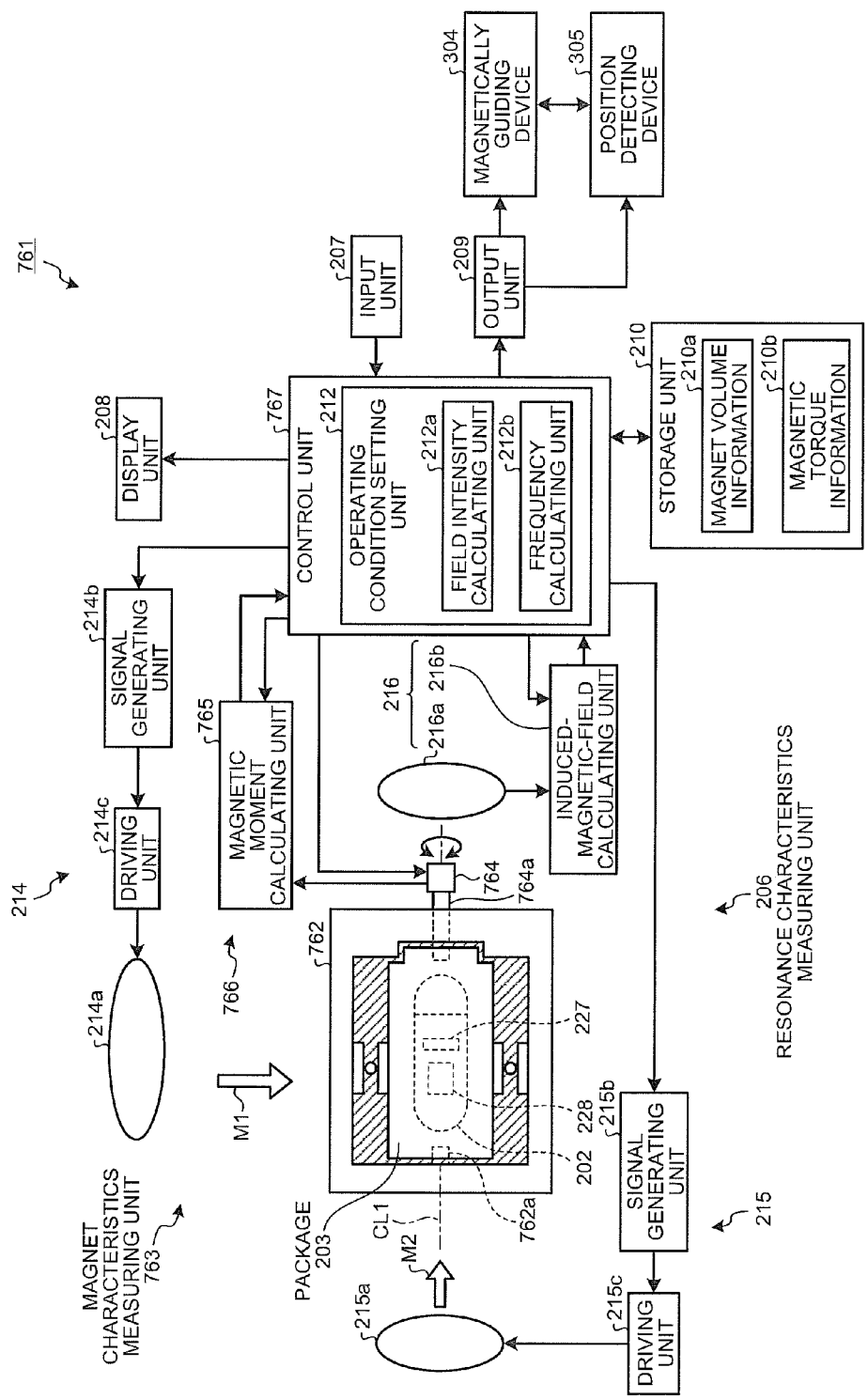
FIG. 29 is a block diagram schematically showing an example structure of a checking device in accordance with a tenth embodiment of the present invention.

FIG. 29 is a block diagram schematically showing an example structure of a checking device in accordance with the tenth embodiment of the present invention. As shown in FIG. 29, the checking device 761 in accordance with the tenth embodiment is the same as the checking device 201 of the sixth embodiment, except that the housing unit 204 is replaced with a housing unit 762, the magnet characteristics measuring unit 205 is replaced with a magnet characteristics measuring unit 763, and the control unit 211 is replaced with a control unit 767. In this checking device 761, the magnet characteristics measuring unit 763 includes a magnetic moment measuring unit 766 in place of the magnetic moment measuring unit 213 of the sixth embodiment. The magnetic moment measuring unit 766 includes: a magnetic torque measuring unit 764 that measures the magnetic torque generated when a magnetic field is applied to the capsule medical device 202; and a magnetic moment calculating unit 765 that calculates the magnetic moment of the magnet 227 inside the capsule medical device 202, based on the result of the measurement carried out by the magnetic torque measuring unit 764. A magnetically guiding system in accordance with the tenth embodiment of the present invention is the same as the magnetically guiding system 301 of the sixth embodiment (see FIG. 20), except that the checking device 201 is replaced with the checking device 761. The other configurations of this embodiment are the same as those of the sixth embodiment, and the same components as those of the sixth embodiment are denoted by the same reference numerals as those used in the sixth embodiment.

The housing unit 762 functions as the supporting unit that supports the capsule medical device 202 to be checked. More specifically, the housing unit 762 defines the direction of the package 203, and has a concave portion that has such a shape as to be engaged with the external shape of the package 203. The housing unit 762 has a supporting unit 762a formed on one of the two wall portions through which the central axis CL1 of the package 203 engaged with the concave portion extends. The supporting unit 762a can be put in and out by a spring or the like. A through hole that is parallel to the central axis CL1 is formed on the other one of the two wall portions. A measuring device 764a of the magnetic torque measuring unit 764 is rotatably inserted through the through hole of the housing unit 762. The housing unit 762 rotatably supports the package engaged with the concave portion, with the use of the supporting unit 762a and a bearing structure or the like. In this manner, the housing unit 762 rotatably supports and houses the capsule medical device 202 via the package 203.

The magnet characteristics measuring unit 763 measures the characteristics of the magnet 227 provided inside the capsule medical device 202. More specifically, the magnet characteristics measuring unit 763 measures the magnetic moment as an example of the characteristics of the magnet 227. As shown in FIG. 29, the magnet characteristics measuring unit 763 includes: the magnetization direction control unit 214 that applies the guiding magnetic field M1 to the capsule medical device 202; and the magnetic moment measuring unit 766 that measures the magnetic moment of the magnet 227, based on the magnetic torque of the magnet 227 inside the capsule medical device 202 generated by applying the guiding magnetic field M1.

The magnetic moment measuring unit 766 measures the magnetic moment of the magnet 227 by measuring the magnetic torque of the magnet 227 inside the capsule medical device 202. The magnetic moment measuring unit 766 includes: the magnetic torque measuring unit 764 that measures the magnetic torque of the magnet 227 generated by the action of the guiding magnetic field M1 applied by the magnetization direction control unit 214; and the magnetic moment calculating unit 765 that calculates the magnetic moment of the magnet 227, based on the result of the measurement carried out by the magnetic torque measuring unit 764.

The magnetic torque measuring unit 764 includes the measuring device 764a inserted through the through hole of the housing unit 762, and uses the measuring device 764a to measure the magnetic torque of the magnet 227 inside the capsule medical device 202. More specifically, the measuring device 764a is rotatably inserted through the through hole of the housing unit 762, and is detachably fitted and inserted into a concave portion at an end portion of the package 203. In this manner, the measuring unit 764a is relatively fixed to the package 203. The magnetic torque measuring unit 764 rotatably supports the measuring device 764a, and measures the torque of the package 203 rotating around the central axis CL1 together with the capsule medical device 202 by virtue of the effect of the guiding magnetic field M1 of the magnetization direction control unit 214. The capsule medical device 202 is relatively fixed to the package 203. Accordingly, the torque of the package 203 measured by the magnetic torque measuring unit 764 is the torque of the capsule medical device 202 rotating by virtue of the effect of the guiding magnetic field M1 of the magnetization direction control unit 214, and is equivalent to the magnetic torque of the magnet 227 inside the capsule medical device 202. The magnetic torque measuring unit 764 transmits the magnetic torque of the magnet 227 to the magnetic moment calculating unit 765.

The magnetic moment calculating unit 765 calculates the magnetic moment of the magnet 227, based on the result of the measurement carried out by the magnetic torque measuring unit 764. More specifically, the magnetic moment calculating unit 765 obtains the value of the magnetic torque of the magnet 227 inside the capsule medical device 202, from the magnetic torque measuring unit 764. The magnetic moment calculating unit 765 also obtains the field intensity observed when the magnetic torque of the magnet 227 is measured, from the control unit 767. The field intensity observed when the magnetic torque is measured is the field intensity of the guiding magnetic field M1 the magnetization direction control unit 214 applies to the capsule medical device 202 when the magnetic torque measuring unit 764 measures the magnetic torque of the magnet 227. The magnetic moment calculating unit 765 divides the value of the magnetic torque of the magnet 227 by the field intensity observed at the time of the magnetic torque measurement. By doing so, the magnetic moment calculating unit 765 calculates the magnetic moment of the magnet 227. The magnetic moment calculating unit 765 then transmits the calculated value of the magnetic moment as the measured value of the magnetic moment of the magnet 227 to the control unit 767.

In the magnet characteristics measuring unit 763, the magnetization direction control unit 214 generates the guiding magnetic field M1 that is a rotating magnetic field of predetermined field intensity, under the control of the control unit 767. The magnetization direction control unit 214 applies the guiding magnetic field M1 to the capsule medical device 202. In this case, the guiding magnetic field M1 as a rotating magnetic field acts on the magnet 227 inside the capsule medical device 202, and causes the package 203 to rotate together with the capsule medical device 202 around the central axis CL1. In this manner, the magnetic torque of the package 203, which is the magnetic torque of the magnet 227 inside the capsule medical device 202, is generated.

The control unit 767 controls the magnetization direction control unit 214 (to be specific, the signal generating unit 214b) to generate the rotating magnetic field (the guiding magnetic field M1) of the predetermined magnetic intensity that can rotate the package 203 together with the capsule medical device 202 around the central axis CL1. The control unit 767 then controls the magnetic torque measuring unit 764 to measure the magnetic torque of the magnet 227 inside the capsule medical device 202 that is generated by virtue of the effect of the guiding magnetic field M1. The control unit 767 also controls the magnetic moment calculating unit 765 to calculate the magnetic moment of the magnet 227, based on the result of the measurement carried out by the magnetic torque measuring unit 764. By doing so, the control unit 767 obtains the measured value of the magnetic moment of the magnet 227 from the magnetic moment calculating unit 765. Except for the functions to control the magnetization direction control unit 214, the magnetic torque measuring unit 764, and the magnetic moment calculating unit 765, the control unit 767 has the same functions as those of the control unit 211 of the checking device 201 of the sixth embodiment.

As well as the value of the magnetic moment of the magnet 227 measured by the magnetic moment measuring unit 766, the control unit 767 may obtain the result of the measurement carried out by the magnetic torque measuring unit 764 as an aspect of the characteristics of the magnet 227. The result of the measurement carried out by the magnetic torque measuring unit 764 is the value of the magnetic torque of the magnet 227 inside the capsule medical device 202 measured when the rotating magnetic field of the predetermined field intensity is applied. The value of the measured magnetic torque may be used as the parameter in the operation by the field intensity calculating unit 212a to calculate the field intensity, or may be transmitted from the output unit 209 as the reference parameter in the magnetic guiding of the capsule medical device 202 to the magnetically guiding device 304.

As described above, in the tenth embodiment of the present invention, the magnetization direction control unit applies a rotating magnetic field of predetermined field intensity to the capsule medical device to be checked. The magnetic torque measuring unit measures the magnetic torque of the magnet inside the capsule medical device that is generated by virtue of the effect of the rotating magnetic field. The magnetic moment calculating unit calculates the magnetic moment of the magnet inside the capsule medical device, based on the result of the measurement calculated by the magnetic torque measuring unit. The other configurations of this embodiment are the same as those of the sixth embodiment. Accordingly, the same effects as those of the sixth embodiment can be achieved, and it is possible to form a checking device that can further measure the magnetic torque of the capsule medical device generated when the rotating magnetic field of the predetermined field intensity is applied, with the characteristics of the magnet inside the capsule medical device being the magnetic torque.

In each of the sixth through tenth embodiments, the capsule medical device housed in a package is checked. However, the present invention is not limited to that, and the capsule medical device may be taken out of the package, and is housed in a housing unit. The capsule medical device supported directly by the housing unit may be checked.

In each of the sixth through tenth embodiments, the operating condition information such as the field intensity condition and the frequency condition that are set by the operating condition setting unit is transmitted to the magnetically guiding device and the position detecting device via the output unit. The magnetically guiding device and the position detecting device then set the initial operating conditions. However, the present invention is not limited to that arrangement. The operating conditions that are set for the magnetically guiding device by the operating condition setting unit may be displayed on the display unit, and a user may input the information displayed on the display unit into the magnetically guiding device, so as to set the initial operating conditions in the magnetically guiding device. Also, the operating conditions that are set for the position detecting device by the operating condition setting unit may be displayed on the display unit, and a user may input the information displayed on the display unit into the position detecting device, so as to set the initial operating conditions in the position detecting device.

In each of the seventh through ninth embodiments, the flux density measuring unit 434a measures the residual flux density of the magnet 227 inside the capsule medical device 202 via the measuring device 434b that is rotatively moved around the capsule medical device 202 by the drive system 435. However, the present invention is not limited to that arrangement. The rotating magnetic field of the magnetization direction control unit 214 may be applied to the magnet 227 inside the capsule medical device 202, so as to rotate the capsule medical device 202 at least once, instead of rotatively moving the measuring device 434b of the flux density measuring unit 434a. The flux density measuring unit of the checking device of the present invention may sequentially measure flux densities of the magnet 227 inside the capsule medical device 202 in such a rotating state, and may set the largest value of the flux densities as the residual flux density of the magnet 227.

In each of the sixth through tenth embodiments, the capsule medical device 202 having the magnet 227 inside the capsule-like casing 220 in such a manner that the radial direction of the capsule-like casing 220 is coincident with the magnetization direction is described as an example of the subject to be tested by the checking device of the present invention. However, the present invention is not limited to that arrangement, and the capsule medical device to be checked by the checking device of the present invention may be a capsule medical device that has a magnet provided therein in such a manner that the magnetization direction is coincident with a desired comparative direction with respect to the capsule-like casings such as the longitudinal direction of the capsule-like casing. In such a case, the center of the rotation of the capsule medical device to be checked is not limited to the longitudinal axis of the capsule-like casing, and may be the magnetization direction of the internal magnet.

In each of the seventh through ninth embodiments, the measuring device 434b of the flux density measuring unit 434a is rotatively moved about the central axis CL1 of the package 203. However, the present invention is not limited to that arrangement, and the measuring device 434b of the flux density measuring unit 434a may be rotatively moved about a desired axis that is a pathway passing through a position in the magnetization direction of the magnet 227 inside the capsule medical device 202 to be checked.

In each of the sixth through tenth embodiments, the capsule medical device 202 that captures in-vivo images of a test subject is described as an example of the capsule medical device to be checked by the checking device of the present invention. However, the present invention is not limited to that arrangement, and the capsule medical device to be checked may be any kind of medical device, as long as it has at least one magnet (magnetic material) for allowing the magnetic guiding by the magnetically guiding device. For example, the capsule medical device to be checked may be a capsule-type pH measuring device that measures the pH value in a living body, or may be a capsule-type medication device that has the function to disperse or inject medicine into a living body. Alternatively, the capsule medical device to be checked may be a capsule-type collecting device that collects a substance from a living body. Further, the capsule medical device to be checked by the checking device of any of the sixth, seventh, and tenth embodiments may not include the image capturing function.

In each of the sixth and eighth through tenth embodiments, the magnetization direction of the magnet 227 inside the capsule medical device 202 is controlled by the magnetization direction control unit 214 including the magnetic field generating coil 214a that generates a magnetic field through a power supply. However, the present invention is not limited to that arrangement. A permanent magnet may be placed in the vicinity of the magnet 227 inside the capsule medical device 202 to be checked, and the magnetization direction of the magnet 227 may be controlled by the magnetic field of the permanent magnet.

In the eighth embodiment, the angle measuring unit 545 calculates the angle between the reference image and the comparative image obtained by the image acquiring unit 544 from the capsule medical device 202, and measures the angle difference between the reference direction of the image capturing unit 222 and the magnetization direction of the magnet 227 inside the capsule medical device 202. However, the present invention is not limited to that arrangement. The storage unit 210 stores beforehand the reference image data that is the data about an image that is captured by the image capturing unit 222 when the reference direction of the image capturing unit 222 is coincident with the reference direction of the image member 542*a*. The angle measuring unit 545 obtains the reference image data in the storage unit 210 from the control unit 547. The angle measuring unit 545 obtains the data about the comparative data from the image acquiring unit 544, and calculates the angle between the data obtained from the image acquiring unit 544 (the data about the image captured by the image capturing unit 222) and the preset reference image data. By doing so, the angle measuring unit 545 may measure the angle difference between the reference direction of the image capturing unit 222 and the magnetization direction of the magnet 227 inside the capsule medical device 202.

In the tenth embodiment, the magnetic moment of the magnet 227 is measured based on the measured value of the magnetic torque of the magnet 227. However, the angle difference between the reference direction of the image capturing unit 222 and the magnetization direction of the magnet 227 inside the capsule medical device 202 may also be measured, as described in the eighth and ninth embodiments. In other words, the checking device of the eighth or ninth embodiment may be combined with the checking device of the tenth embodiment. In such a case, the checking device 761 of the tenth embodiment may include the image member 542*a*, the image acquiring unit 544, the angle measuring unit 545, the operating condition setting unit 546, and the likes, like the checking device of the eighth embodiment. Alternatively, the checking device 761 of the tenth embodiment may include the image member 542*a*, the image acquiring unit 544, the operating condition setting unit 656, and the likes, like the checking device of the ninth embodiment.

Additional advantages and modifications will readily occur to those skilled in the art. Therefore, the invention in its broader aspects is not limited to the specific details and representative embodiments shown and described herein. Accordingly, various modifications may be made without departing from the scope of the general inventive concept as defined by the appended claims and their equivalents.

What is claimed is:

1. A magnetically guiding system comprising:
a capsule medical device that has a magnet;
an information acquiring device that acquires physical information about magnetic guiding of the capsule medical device;
a magnetic field generating unit that generates a magnetic field for magnetically guiding the capsule medical device;
a control unit that sets a magnetic field condition based on the physical information acquired by the information acquiring device and controls the magnetic field generating unit to generate the magnetic field corresponding to the magnetic field condition;
a container that has the capsule medical device and a liquid introduced thereinto;
a liquid temperature adjusting unit that adjusts temperature of the liquid inside the container;
a temperature measuring unit that measures the temperature of the liquid adjusted by the liquid temperature adjusting unit; and
a receiving unit that receives an image captured by the capsule medical device,
wherein the information acquiring device determines timing when the capsule medical device starts floating up or sinking down in the liquid, based on the image received by the receiving unit, and obtains the physical information, based on the temperature of the liquid measured by the temperature measuring unit at the timing.

2. The magnetically guiding system according to claim 1, further comprising
a receiving unit that receives a transmission signal from the capsule medical device, the transmission signal containing an image captured by the capsule medical device and the physical information,
wherein the capsule medical device stores the physical information in advance and transmits the image together with the stored physical information, and
the information acquiring device extracts the physical information from the transmission signal received by the receiving unit from the capsule medical device.

3. The magnetically guiding system according to claim 1, wherein the information acquiring device includes a magnetic moment measuring unit that measures magnetic moment of the magnet.

4. The magnetically guiding system according to claim 1, further comprising
an image member that has a reference direction and has an image drawn thereon,
wherein
the capsule medical device includes:
an image capturing unit that captures an image of the image member in such a manner that the reference direction of the image member is coincident with a magnetization direction of the magnet, the image capturing unit having a reference direction; and
a transmission unit that radio-transmits the image captured by the image capturing unit,
the information acquiring device acquires image data of the image of the image member captured by the image capturing unit when the reference direction of the image member is coincident with the magnetization direction of the magnet, and
the information acquiring device calculates an angle between the reference direction of the image capturing unit and the magnetization direction of the magnet, based on the image data and reference image data of an image captured when the reference direction of the image capturing unit is coincident with the reference direction of the image member.

5. The magnetically guiding system according to claim 1, further comprising
an image member that has a reference direction and has an image drawn thereon,
wherein
the magnetic field generating unit generates a magnetic field that causes the capsule medical device to rotate in such a manner that a reference direction of an image acquired by the information acquiring device is coincident with the reference direction of the image member,
the capsule medical device includes:
an image capturing unit that captures an image of the image member; and
a transmission unit that radio-transmits the image captured by the image capturing unit, and the information acquiring device calculates an angle between a magnetization direction of the magnet and the reference direction of the image member, based on a direction of the magnetic field generated from the magnetic field generating unit.

6. The magnetically guiding system according to claim 1, wherein the capsule medical device further includes a resonance circuit, and the magnetically guiding system further comprises a resonance characteristics measuring unit that measures resonance characteristics of the capsule medical device by detecting an induced magnetic field generated from the resonance circuit.

7. The magnetically guiding system according to claim 1, wherein the information acquiring device includes a supporting unit that supports the capsule medical device.

8. The magnetically guiding system according to claim 7, wherein the capsule medical device is housed in a package, and the supporting unit supports the medical device via the package.

* * * * *